(12) United States Patent
Welch et al.

(10) Patent No.: US 8,126,653 B2
(45) Date of Patent: *Feb. 28, 2012

(54) SYNTHETIC NUCLEIC ACIDS FOR EXPRESSION OF ENCODED PROTEINS

(75) Inventors: Mark Welch, Fremont, CA (US); Claes Gustafsson, Belmont, CA (US)

(73) Assignee: DNA Twopointo, Inc., Menlo Park, CA (US)

( * ) Notice: Subject to any disclaimer, the term of this patent is extended or adjusted under 35 U.S.C. 154(b) by 730 days.

This patent is subject to a terminal disclaimer.

(21) Appl. No.: 12/184,230

(22) Filed: Jul. 31, 2008

(65) Prior Publication Data

US 2010/0029493 A1    Feb. 4, 2010

(51) Int. Cl.
*G01N 33/48* (2006.01)
*C12Q 1/68* (2006.01)
*G06G 7/58* (2006.01)
(52) U.S. Cl. .................. 702/19; 435/6; 702/20; 703/11
(58) Field of Classification Search ........................ None
See application file for complete search history.

(56) References Cited

U.S. PATENT DOCUMENTS

| | | | |
|---|---|---|---|
| 5,254,463 A | 10/1993 | de Boer et al. | |
| 5,500,365 A | 3/1996 | Fischhoff et al. | |
| 5,689,052 A | 11/1997 | Brown et al. | |
| 5,786,464 A | 7/1998 | Seed | |
| 5,795,737 A | 8/1998 | Seed et al. | |
| 5,965,726 A | 10/1999 | Pavlakis et al. | |
| 6,114,148 A | 9/2000 | Seed et al. | |
| 6,291,664 B1 | 9/2001 | Pavlakis et al. | |
| 6,414,132 B1 | 7/2002 | Pavlakis et al. | |
| 6,733,994 B2 | 5/2004 | Weiner et al. | |
| 6,794,498 B2 | 9/2004 | Pavlakis et al. | |
| 6,924,365 B1 | 8/2005 | Miller et al. | |
| 7,132,262 B2 | 11/2006 | Ertl et al. | |
| RE39,649 E | 5/2007 | Lehmann | |
| 2003/0213010 A1 | 11/2003 | Weaver et al. | |
| 2006/0136184 A1 | 6/2006 | Gustafsson et al. | |
| 2007/0028321 A1 | 2/2007 | Manjunath et al. | |
| 2007/0238657 A1 | 10/2007 | Itoh et al. | |

FOREIGN PATENT DOCUMENTS

WO    WO 2005/013090 A2    2/2005
WO    WO 2008/075911 A1    6/2008

OTHER PUBLICATIONS

PCT Invitation to Pay Additional Fees and, Where Applicable, Protest Fee dated Sep. 28, 2009 for PCT/US09/03412.
Gustafsson, et al, "Condon bias and heterologous protein expression," Trends in Biotechnology, vol. 22, No. 7, Jul. 2004, pp. 346-353.
Angellotti et al., 2007, "CodonO: codon usage bias analysis within and across genomes", Nucleic Acids Research, 35, Web Server issue doi:10.1093/nar/gkm392, W132-W136.
Duret et al., 2000, "Determinants of Substitution Rates in Mammalian Genes: Expression Pattern Affects Selection Intensity but Not Mutation Rate", Mol. Biol. Evol. 17, pp. 68-74.
Gribskov et al., 1984, "The codon preference plot: graphic analysis of protein coding sequences and prediction of gene expression", Nucleic Acids Research, 12, pp. 539-549.
Grote et al., 2005, "JCat: a novel tool to adapt codon usage of a target gene to its potential expression host", Nucleic Acids Research, 33, Web Server issue doi:10.1093/nar/gki376, W526-W531.
Ko et al., 2005, "Optimization of Codon Usage Enhances the Immunogenicity of a DNA Vaccine Encoding Mycobacterial Antigen Ag85B", Infection and Immunity, 73, pp. 5666-5674.
McLachlan et al., 1984, "A method for measuring the non-random bias of a codon usage table", Nucleic Acids Research, 12, pp. 9567-9575.
Narum et al., 2001, "Codon Optimization of Gene Fragments Encoding *Plasmodium falciparum* Merzoite Proteins Enhances DNA Vaccine Protein Expression and Immunogenicity in Mice", Infection and Immunity, 69, pp. 7250-7253.
Sharp et al., 1987, "The codon adaptation index—a measure of directional synonymous codon usage bias, and its potential applications", Nucleic Acids Research, 15, pp. 1281-1295.
Shields et al., 1987, "Synonymous codon usage in *Bacillus subtilis* reflects both translational selection and mutational biases", Nucleic Acids Research, 15, pp. 8023-8040.
Smith et al., 2001, "Synonymous Codon Bias Is Not Caused by Mutation Bias in G+C-Rich Genes in Humans", Mol. Biol. Evol. 18, pp. 982-986.
Zeeberg, 2008, "Shannon Information Theoretic Computation of Synonymous Codon Usage Biases in Coding Regions of Human and Mouse Genomes", Cold Spring Harbor Laboratory Press, 12, pp. 944-955, downloaded from www.genome.org/cgi/doi/10.1101/gr. 213402.
Zhao et al., 2005, "Gene Codon Composition Determines Differentiation-Dependent Expression of a Viral Capsid Gene in Keratinocytes in Vitro and in Vivo", Molecular and Cellular Biology, 25, pp. 8643-8655.

*Primary Examiner* — Shubo Zhou
(74) *Attorney, Agent, or Firm* — Morgan, Lewis & Bockius LLP

(57) ABSTRACT

A method of determining a property that affects expression of polynucleotides in an expression system. A plurality of polynucleotides, each encoding a polypeptide sequence, is constructed. An amino acid is encoded a plurality of times in both a first and second polynucleotide in the plurality. The amino acid is encodable by a plurality of synonymous codons including a first codon. The first codon is in the first polynucleotide at a first frequency relative to other synonymous codons, and is in the second polynucleotide at a second frequency relative to other synonymous codons. The first and second frequencies are different. Each polynucleotide is individually expressed in the expression system to measure an expression property value of the polynucleotides, thereby determining a property that affects expression of polynucleotides. The property is an effect that a frequency of use of one or more codons has on expression of polynucleotides in the expression system.

63 Claims, 20 Drawing Sheets

(SEQ ID NO: 4)

dG = 30.4 ntA

| Phi29 Pol. Variant | Codon bias table | Threshold | CAI | RNA @147 | 5' RNA | 5' AT Wobble | GC6 | GC7 | WT ID | Expression |
|---|---|---|---|---|---|---|---|---|---|---|
| 1 | E. coli | 23% | 0.809 | -21.4 | -25.2 | 0.000 | 14 | 5 | 0.777 | 22 ± 7 |
| 2 | E. coli | 2% | 0.561 | -4.9 | -30.4 | 0.000 | 10 | 7 | 0.773 | ND |
| 3 | E. coli II | 27% | 0.945 | -21.4 | -20.9 | 0.733 | 11 | 4 | 0.765 | 4 ± 3 |
| 4 | E. coli | 28% | 0.803 | -7.8 | -21.4 | 0.600 | 16 | 4 | 0.773 | 32 ± 6 |
| 5 | E. coli II | 4% | 0.748 | -21.4 | -20.6 | 0.800 | 5 | 0 | 0.770 | 20 ± 4 |
| 6 | E. coli II | 2% | 0.727 | -7.4 | -28.3 | 0.067 | 9 | 5 | 0.770 | 120 ± 15 |
| 7 | E. coli | 2% | 0.529 | -21.2 | -20.6 | 0.800 | 11 | 0 | 0.774 | 51 ± 12 |
| 8 | E. coli II | 25% | 0.889 | -10.9 | -25.6 | 0.200 | 4 | 1 | 0.761 | 55 ± 19 |
| 9 | E. coli II | 10% | 0.792 | -9.2 | -23.3 | 0.400 | 4 | 0 | 0.772 | 76 ± 8 |
| 10 | E. coli II | 10% | 0.801 | -15.2 | -26.8 | 0.400 | 3 | 0 | 0.771 | 68 ± 3 |
| 11 | E. coli II | 10% | 0.789 | -15.2 | -24.2 | 0.467 | 7 | 0 | 0.773 | ND |
| 12 | E. coli II | 27% | 0.906 | -9.5 | -26.9 | 0.400 | 8 | 3 | 0.762 | 83 ± 5 |
| 13 | E. coli II | 2% | 0.711 | -10.6 | -31.4 | 0.400 | 12 | 3 | 0.759 | 23 ± 3 |
| 15 | E. coli II | 27% | 0.891 | -8.8 | -20.1 | 0.600 | 10 | 5 | 0.838 | 20 ± 4 |
| 16 | E. coli II | 2% | 0.485 | -7.8 | -24.2 | 0.467 | 5 | 3 | 0.963 | ND |
| 17 | E. coli | 2% | 0.314 | -5.8 | -23 | 0.467 | 5 | 3 | 0.996 | ND |
| 18 | E. coli II | 21% | 0.788 | -21.9 | -26.9 | 0.333 | 12 | 3 | 0.654 | 103 ± 12 |
| 19 | E. coli II | 2% | 0.64 | -7.4 | -23 | 0.333 | 10 | 3 | 0.624 | 301 ± 65 |
| 20 | E. coli | 2% | 0.526 | -10.9 | -23.8 | 0.333 | 1 | 0 | 0.630 | 235 ± 32 |
| 21 | E. coli II | 15% | 0.816 | -6.6 | -22.5 | 0.400 | 4 | 2 | 0.773 | 68 ± 7 |
| WT | WT | NA | 0.313 | -7 | -23 | 0.470 | 3 | 3 | 1.000 | ND |

Figure 2

|  | 1: 2-AAG | 2: 2-AAA | 3: 3-CAC | 4: 3-CAT | 5: 5-CCG | 6: 5-CCA |
|---|---|---|---|---|---|---|
| 1:1 | 1 | 0 | 1 | 0 | 1 | 0 |
| 2:2 | 1 | 0 | 1 | 0 | 1 | 0 |
| 3:3 | 0 | 1 | 0 | 1 | 1 | 0 |
| 4:4 | 0 | 1 | 0 | 1 | 1 | 0 |
| 5:5 | 0 | 1 | 1 | 0 | 0 | 1 |
| 6:6 | 1 | 0 | 1 | 1 | 1 | 0 |
| 7:7 | 0 | 1 | 0 | 1 | 0 | 1 |
| 8:8 | 0 | 1 | 1 | 0 | 1 | 0 |

Figure 5

```
                            SEQUENCE LISTING

<160> NUMBER OF SEQ ID NOS: 4

<210> SEQ ID NO 1
<211> LENGTH: 5071
<212> TYPE: DNA
<213> ORGANISM: Artificial Sequence
<220> FEATURE:
<223> OTHER INFORMATION: 5 prime CONSTANT SEQUENCE of phage phi29 VECTOR

<400> SEQUENCE: 1
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt      300 ctttaatagt ggactcttgt tccaaactgg aacaacactc aaccctatct cggtctattc     360
ttttgattta taggggattt tgccgatttc ggcctattgg ttaaaaaatg agctgattta     420
acaaaaattt aacgcgaatt ttaacaaaat attaacgttt acaatttcag gtggcactttt    480 tcggggaaat gtgcgcggaa cccctatttg tttattttc taaatacatt caaatatgta      540
tccgctcatg aattaattct tagaaaaact catcgagcat caaatgaaac tgcaattttat    600 tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttcttttcc    840 agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
```

```
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca gggtagcc agcagcatcc    2940 tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
```

```
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttttt tcccgcgttt    4500 tcgcagaaac gtggctggcc tggttcacca cgcgggaaac ggtctgataa agacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatattac c                                  5071
```

<210> SEQ ID NO 2
<211> LENGTH: 271
<212> TYPE: DNA
<213> ORGANISM: Artificial Sequence
<220> FEATURE:
<223> OTHER INFORMATION: 3 prime CONSTANT SEQUENCE of phage phi29 VECTOR

<400> SEQUENCE: 2

```
tgataaagtg gctccaacac ttcctactag cataacccct tggggcctct aaacgggtct      60 tgagggggttt tttggaattc gagctccgtc gacaagcttg cggccgcact cgagcaccac    120
caccaccacc actgagatcc ggctgctaac aaagcccgaa aggaagctga gttggctgct    180
gccaccgctg agcaataact agcataaccc cttggggcct ctaaacgggt cttgaggggt    240 ttttgctga aggaggaac tatatccgga t                                    271
```

<210> SEQ ID NO 3
<211> LENGTH: 50
<212> TYPE: DNA
<213> ORGANISM: Artificial Sequence

```
-continued

<220> FEATURE:
<223> OTHER INFORMATION: UNAFold-calculated phi29 polymerase gene mRNA
      structures (translated region)

<400> SEQUENCE: 3
gtgggttctg aaagtgcagg cggatctgta ctttcacaac ctgaaattcg            50

<210> SEQ ID NO 4
<211> LENGTH: 121
<212> TYPE: DNA
<213> ORGANISM: Artificial Sequence
<220> FEATURE:
<223> OTHER INFORMATION: UNAFold-calculated phi29 polymerase gene mRNA
      structures (5 prime untranslated region)

<400> SEQUENCE: 4
ggggaattgt gagcggataa caattcccct ctagaaataa ttttgtttaa ctttaagaag     60
gagatattac catgaagcac atgccgcgga agatgtactc ctgcgacttc gagacgacca   120
c                                                                  121
```

SYNTHETIC NUCLEIC ACIDS FOR EXPRESSION OF ENCODED PROTEINS

STATEMENT AS TO RIGHTS TO INVENTIONS MADE UNDER FEDERALLY SPONSORED RESEARCH AND DEVELOPMENT

The research described in this application was funded in part by NSF SBIR grant 0638333.

CROSS REFERENCE TO RELATED APPLICATION

This application claims priority under 35 U.S.C. §119(e) of U.S. Provisional Application No. 61/131,238, filed Jun. 6, 2008. This application also claims priority under 35 U.S.C. §119(e) of U.S. Provisional Application No. 61/132,892, filed on Jun. 24, 2008.

1. FIELD OF THE INVENTION

This invention relates to methods for designing nucleic acids with desired properties, particularly for the expression of encoded proteins.

2. BACKGROUND OF THE INVENTION

It is frequently desirable to express proteins encoded by nucleic acids, for example for production of the protein to be used in a therapeutic or biocatalytic application, or for the protein to perform a function within the cell in which it is expressed. Due to the degeneracy of the genetic code, there are numerous different nucleotide sequences that can all encode the same protein. Redesigning a naturally occurring gene sequence by choosing different codons without necessarily altering the encoded amino acid sequence often dramatically increases protein expression levels (Gustafsson et al., 2004, "Codon bias and heterologous protein expression," Journal/Trends Biotechnol 22, 346-53).

The inspiration for most codon optimization algorithms comes from assessing coding sequence characteristics present in naturally derived genomic sequences as a proxy for synthetic genes. The assumption guiding this method is that synthetic genes will express well if the gene sequence mimic the nucleotide sequence characteristics of the host genome. Variables such as codon adaptation index (CAI), mRNA secondary structures, cis-regulatory sequences, GC content and many other similar variables have been shown to somewhat correlate with protein expression levels (Villalobos et al., 2006, "Gene Designer: a synthetic biology tool for constructing artificial DNA segments," Journal/BMC Bioinformatics 7, 285). A problem with these correlations is that protein expression is generally believed to be controlled at the level of initiation of transcription and translation, not translational velocity. These factors are controlled by promoter strength and the strength of the ribosome binding site, which are different for every natural protein, and which are not taken into account in such blunt analyses as the most common codon for a particular amino acid in every protein in an organism's genome. The sequence characteristics of the coding sequences may reflect other factors such as evolutionary constraints involved in facilitating DNA replication, mutational bias, intrinsic metabolic regulation, transposon resistance, ancestral origin etc. rather than serving as a useful guide to design principles with which to obtain high levels expression of recombinant protein (Moura et al., 2005, "Comparative context analysis of codon pairs on an ORFeome scale," Journal/Genome Biol. 6, R28).

To date, there has been no systematic study of the effect of codon choices on protein expression, while keeping other expression control elements, such as promoters and ribosome binding sequences, constant. Thus there is currently no reliable strategy for selecting the codons in a synthetic gene to obtain high protein expression levels, nor is there currently a reliable algorithm with which to assess the likely level of protein expressed from a synthetic gene. There is thus a need in the art for both of these.

3. SUMMARY OF THE INVENTION

The systems and methods described here apply computational biology and data mining techniques to important molecular design problems. In particular, novel ways to map codon sequence space for polynucleotide sequences that encode polypeptides are described. Such maps are used to direct modifications of polynucleotide sequences in order to obtain desired expression characteristics of encoded polypeptides.

Methods are disclosed for biological engineering using the design and synthesis of plurality of polynucleotides containing designed codon substitutions that are representative of a codon space (the "codon variant set"). The codon space for a polypeptide is defined by the sequence of that polypeptide. The set of all polynucleotides that encode a single defined polypeptide sequence define the codon space for that polypeptide sequence. Because there are sometimes slight variations in the genetic code in different organisms, the codon space for a polypeptide sequence also depends upon the expression system to be used.

The information used to create the codon substitutions that define a codon variant set can be derived from one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. The systematic design and synthesis of codon variants is an aspect of the present invention.

After synthesis, the plurality of polynucleotides containing designed codon substitutions is characterized functionally to measure a property of interest, for example an expression property. Examples of expression properties, include but are not limited to, expression of a polypeptide, expression of a polypeptide in soluble form, or expression of a polypeptide in biologically or chemically active form.

An optional additional step in this method is to model a sequence-expression relationship between (i) one or more variables that are characteristics of the polynucleotide sequences themselves (a "polynucleotide sequence property", including but not limited to the codon bias, the relative or absolute frequency with which specific sequence elements, including but not limited to codons, are used, GC content of the polynucleotide, predicted mRNA secondary structure) and (ii) the property measured for all or the portion of the variants in the variant set (an "expression property" including but not limited to the expression of polypeptide by translation of the polynucleotide in an expression system, the expression of soluble polypeptide by translation of the polynucleotide in an expression system or the expression of biologically or chemically active polypeptide by translation of the polynucleotide in an expression system). The codon variant set may then optionally be redefined to comprise new variants that are designed to have modified values for one or more polynucleotide sequence properties, which values are selected based on a function of the modeled sequence-expression relationship.

In some embodiments, the method further comprises repeating the measuring, modeling, and, optionally, the redefining, until a variant in the codon variant set exhibits a value for the expression property that exceeds a predetermined value.

In some embodiments, the method further comprises repeating the measuring, modeling, and, optionally, the redefining, until a variant in the codon variant set exhibits a value for the expression property that is less than a predetermined value.

In some embodiments, the method further comprises repeating the measuring, modeling, and, optionally, the redefining, a predetermined number of times (e.g., two, three, four, or five times).

In some embodiments, the modeled sequence-expression relationship comprises a plurality of values and each value in the plurality of values describes a relationship between (i) a polynucleotide sequence property and an expression property, (ii) a plurality of polynucleotide sequence properties and an expression property, or (iii) a plurality of polynucleotide sequence properties and a plurality of expression properties.

In some embodiments, the modeling comprises linear regression, non-linear regression, logistic regression, multivariate data analysis, or partial least squares projection to latent variables.

In some embodiments, the modeling comprises computation of a neural network, computation of a Bayesian model, a generalized additive model, a support vector machine, or classification using a regression tree. In some embodiments, the modeling comprises boosting or adaptive boosting (See, for example, Hastie, 2003, *The Elements of Statistical Learning*, Springer, New York).

In some embodiments, the redefining further comprises (i) computing a predicted score for a population of variants of the polynucleotide of interest using the modeled sequence-expression relationship, where each variant in the population of variants includes a codon substitution at one or more codons in the polynucleotide of interest and (ii) selecting the codon variant set from among the population of variants as a function of the predicted score received by each variant in the set of codon variants.

In some embodiments, the modeling further comprises modeling a plurality of relationships between one or more polynucleotide sequence properties and one or more expression properties. Each respective relationship in the plurality of relationships describes the relationship between (i) one or more polynucleotide sequence properties and (ii) one or more expression properties measured for all or the portion of the variants in the codon variant set. Furthermore, the step of redefining the codon variant set (e) comprises redefining the codon variant set to comprise variants that include polynucleotide sequence properties that are selected based on a combination of the plurality of sequence-expression relationships.

In some embodiments, the codon variant set consists of between 5 and 200 variants of the polynucleotide of interest or between 15 and 50 variants of the polynucleotide of interest.

In some embodiments of the invention the expression property is measured in one of the following expression systems: bacterial expression systems including *Escherichia coli*, *Salmonella* species, *Bacillus* species, *Streptomyces* species, *Pseudomonas* species, *Ralstonia eutropha*, *Chlamydomonas* species; yeast expression systems including *Saccharomyces*, *Pichia*, *Klebsiella* and *Candida* species, *Saccaromyces cerevisiae*, *Pichia pastoris*, *Pichia methanolica*, *Klebsiella lactis*; fungal expression systems including *Cryptosporidium* and *Trichoderma* species, filamentous fungal protein production systems, protozoan expression systems including *Plasmodium falciparum* (the causative agent of malaria), *Leishmania* model organisms including *Caenorhabditis elegans*, *Drosophila melanogaster*, *Xenopus laevis*; plants including soybean, bushbean, maize, cotton, tobacco, *Arabidopsis*, tissue culture expression systems including COS cells, Chinese Hamster Ovary cells and fibroblasts including 3T3 cells, cell lines infected with adenovirus, insect cell lines such as those derived from *Spodptera* species for growing baculovirus; model organisms for the study of disease and tests of the efficacies of DNA vaccines such as macaques, mice, rats, guinea pigs, sheep, goats and rabbits; in vitro expression systems prepared from extracts of living cells including *E. coli* extracts, wheat germ extracts, rabbit reticulocyte lysates; in vitro expression systems prepared by assembly of purified individual components.

In some embodiments, the sequence-expression relationship has the form:

$$Y=f(w_1x_1,w_2x_2,\ldots w_ix_i)$$

where,
Y is a quantitative measure of the expression property;
$x_i$ is a descriptor of a polynucleotide sequence property;
$w_i$ is a weight applied to descriptor $x_i$; and
f( ) is a mathematical function.

In some embodiments, the modeling comprises regressing:

$$Y=f(w_1x_1,w_2x_2,\ldots w_ix_i).$$

In some instances this regressing comprises linear regression, non-linear regression, logistic regressing, or partial least squares projection to latent variables.

A sequence-expression relationship derived from the expression properties of a codon variant set of polynucleotides encoding one polypeptide may be used to design polynucleotides to encode a second polypeptide with a different amino acid sequence. The use of a sequence-expression relationship to design polynucleotides for the expression of a polypeptide of interest, where the sequence-expression relationship was derived from polynucleotides encoding polypeptides that are not the polypeptide of interest is an aspect of the invention.

In some embodiments of the invention the modeled sequence-expression relationship is used to elucidate design principles for expression of polynucleotides in specific expression systems.

4. BRIEF DESCRIPTION OF THE FIGURES

FIG. 1 illustrates UNAFold-calculated phi29 polymerase gene mRNA structures. Examples of mRNA structures possible in a 50 nucleotide mRNA window at position 147 (1A) or in the 5' leader (1B) are shown. The Shine-Dalgarno (SD) sequence and the codon for serine at position 10 are indicated. Lowercase letters indicate untranslated nucleotides.

FIG. 2 illustrates the gene design parameter matrix for phi29 polymerase test variants. Columns are as follows: Codon bias table indicates whether the codon bias for all *E. coli.* genes (*E. coli.*) or *E. coli.* class II genes (Henaut and Danchin, 1996, "Analysis and predictions from *Escherichia coli* sequences," *Escherichia Coli and Salmonella Typhimurium Cellular and Molecular Biology* 2, 2047-2066) (*E. coli.* II) was used. Threshold indicates the codon frequency a codon has to exceed in order to be used in the design. CAI is the codon adaptation index, which was not used directly as a design parameter, but was monitored. RNA@147 is the value for the predicted lowest free energy mRNA secondary structure for nucleotides 147-196 of the coding sequence. 5' RNA is the value for the predicted lowest free energy mRNA secondary structure for nucleotides the first 121 nucleotides of the mRNA. 5' AT wobble is the fraction of the first 15 codons using A or T in the third position. GC6 and GC7 refer to the number of runs of consecutive G and/or C nucleotides of length at least 6 or 7, respectively. WT ID is the fraction sequence identity to the wild-type sequence. Expression is the mean and standard deviation of expression relative to the reference clone, multiplied by 100.

FIG. 3 illustrates the expression of five phi29 polymerase variants in *E. coli* strain BL21(DE3) pLysS. Triplicate expression analyses for the indicated variants are shown. The arrow indicates the position of full-length phi29 polymerase. M, molecular weight standards. C, non-induced control expression. "Ref." indicates replicates of the reference variant. Numbers indicate amount in ng for BSA standards.

FIG. 4 illustrates results from PLS fitting of phi29 polymerase variant expression data. All variants listed in FIG. 2 except the wild-type gene are included. Nine variables from FIG. 2 shown to contribute significantly to the model are shown. (Part A) Plot of measured expression levels versus those predicted by the PLS model using 2 latent variables. (Part B) Loading of the variables for LV1, which captures 65% of the expression variance. RNA structure variables are included as the absolute value of the folding free energies listed in FIG. 2. Thus a positive loading indicates preference for stronger structure.

FIG. 5 shows the encoding of variables for sequence-expression modeling when the variables are the possible codons used at the polynucleotide sequence corresponding to each amino acid position. Variant numbers are given in the left hand column. The top row lists the variable number, the amino acid position and then codon. For example the second column is headed "1: 2-AAG", meaning variable 1 is whether the polynucleotide variant uses the codon AAG to encode the second amino acid of the polypeptide. Variants 1, 2 and 6 use the codon AAG at the second position, and therefore have a 1 in this column. The third column, headed "2: 2-AAA" indicates that variable 2 is whether the polynucleotide variant uses the codon AAA to encode the second amino acid of the polypeptide. Variants 3, 4, 5, 7 and 8 use the codon AAA at the second position, and therefore have a 1 in this column.

FIG. 6 shows information from a PLS model correlating the level of phi29 protein expression in *E. coli* with the codons used to encode the protein at each position in the polypeptide. Part A shows the fit between predicted and measured expression levels for a Partial Least Squares (PLS) model of the expression and sequence of the 21 variants described in FIG. 2. Part B shows the positions in the polynucleotide sequence that were identified in this model as possible expression determining positions or regions.

FIG. 7 compares the codon usage of phi29 variants 15 (solid bars) and 19 (striped bars) with the highly expressed genes *E. coli* class II bias (white bars) (Henaut and Danchin, 1996, "Analysis and predictions from *Escherichia coli* sequences," Journal/*Escherichia coli* and *Salmonella typhimurium* cellular and molecular biology 2, 2047-2066). The number of instances of each codon within the gene is shown. Letters indicate codon groups by amino acid where multiple possible codings exist.

FIG. 8 illustrates PLS modeling of phi29 DNA polymerase expression as a function of the frequency of each of the 59 variable codons. The graph shows correlation between measured and predicted values.

FIG. 9 illustrates the expression of six ScFv variants in *E. coli* strain BL21(DE3) pLysS. Triplicate expression analyses for the indicated variants are shown. The arrow indicates the position of full-length phi29 polymerase. M, molecular weight standards. C, non-induced control expression. Numbers indicate amount in ng for BSA standards.

FIG. 10 illustrates results from PLS fitting of scFv variant expression data. Six variables that contribute significantly to the model are shown. (10A) Plot of measured expression levels versus those predicted by the PLS model using 2 latent variables. (10B) Loading of the variables for LV1, which captures 44% of the expression variance. RNA structure variables are included as the absolute value of the folding free energies.

Figure 16:
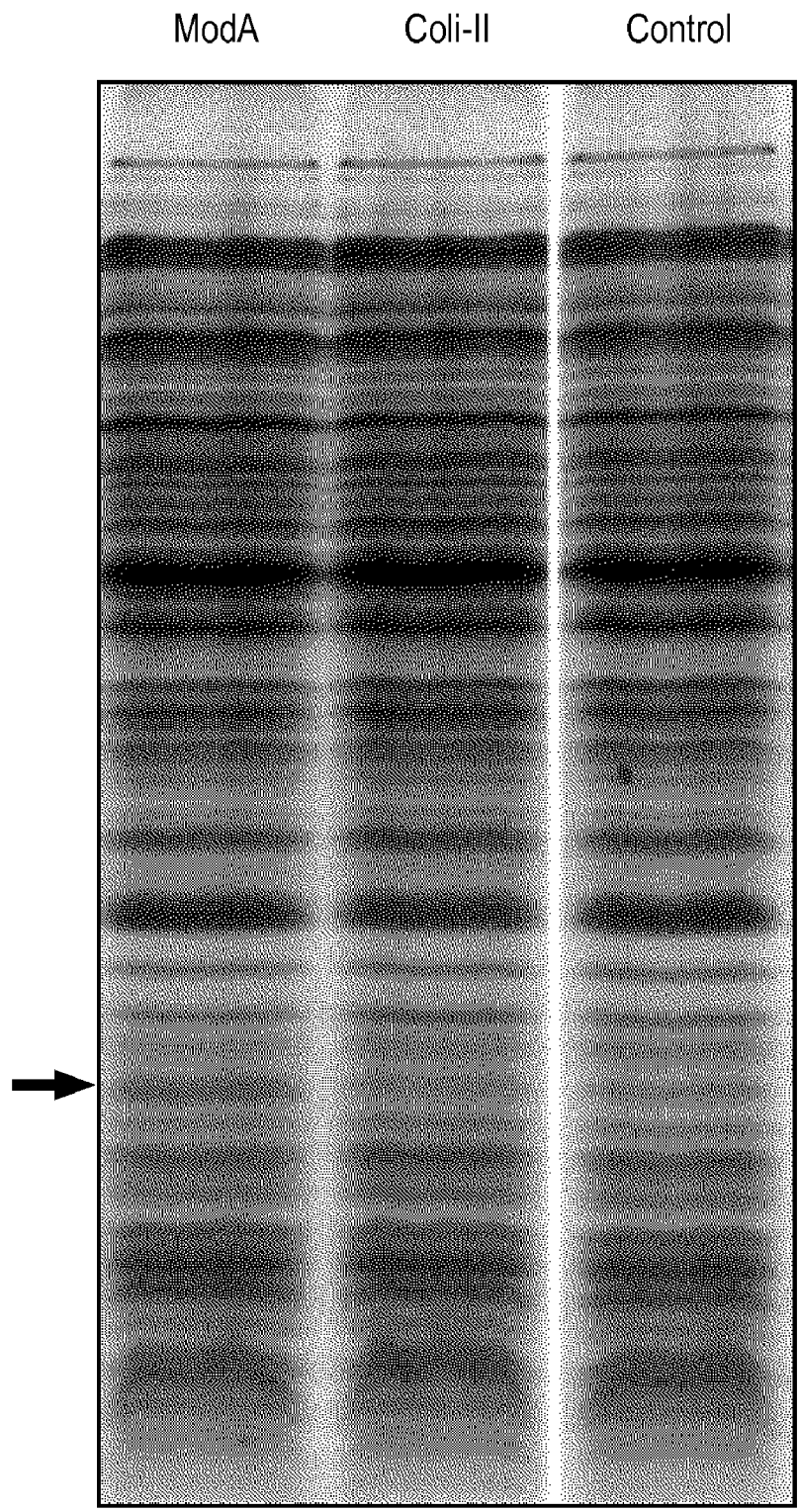

FIG. 16 shows expression of CenpA genes with altered codon bias. PAGE analysis of total expressed protein from *E. coli* strains harboring two different genes for cenpA is shown. The lane labeled "ModA" shows expression from a gene using codon usage derived from a model for expression (see text). The lane labeled "Coli-II" shows expression from a gene designed to match the codon bias of 27 naturally highly expressed genes in *E. coli*. "Control" shows expression from the same host but lacking a CenpA gene. The arrow indicates the position of the full-length CenpA protein.

5. DETAILED DESCRIPTION OF THE INVENTION

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

5.1 DEFINITIONS

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton et al., 1994, *Dictionary of Microbiology and Molecular Biology*, 2nd Ed., John Wiley and Sons, New York, and Hale & Marham, 1991, *The Harper Collins Dictionary of Biology*, Harper Perennial, New York, provide one of skill with a general dictionary of many of the terms used in this invention. Although any methods and materials similar or equivalent to those described herein can be used in the practice or testing of the present invention, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkyl-phosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides that can perform that function or which can be modified (e.g., reverse transcribed) to perform that function are used. Where the polynucleotides are to be used in a scheme that requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., where one or more of the hydroxyl groups are replaced with halogen, aliphatic groups, or is functionalized as ethers, amines, or the like.

Standard A-T and G-C base pairs form under conditions which allow the formation of hydrogen bonds between the N3-H and C4-oxy of thymidine and the N1 and C6-$NH_2$, respectively, of adenosine and between the C2-oxy, N3 and C4-$NH_2$, of cytidine and the C2-$NH_2$, N'—H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other normatural base pairs may be synthesized by the method described in Piccirilli et al., 1990, Nature 343:33-37, hereby incorporated by reference in it entirety, for the synthesis of 2,6-diaminopyrimidine and its complement (1-methylpyrazolo-[4,3]pyrimidine-5,7-(4H, 6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs.

The term "protein" refers to contiguous "amino acids" or amino acid "residues." Typically, proteins have a function. However, proteins also encompass polypeptides and smaller contiguous amino acid sequences that do not have a functional activity. The functional proteins of this invention include, but are not limited to, esterases, dehydrogenases, hydrolases, oxidoreductases, transferases, lyases, ligases, receptors, receptor ligands, cytokines, antibodies, immunomodulatory molecules, signalling molecules, fluorescent proteins and proteins with insecticidal or biocidal activities. Useful general classes of enzymes include, but are not limited to, proteases, cellulases, lipases, hemicellulases, laccases, amylases, glucoamylases, esterases, lactases, polygalacturonases, galactosidases, ligninases, oxidases, peroxidases, glucose isomerases, nitrilases, hydroxylases, polymerases and depolymerases. In addition to enzymes, the encoded proteins which can be used in this invention include, but are not limited to, transcription factors, antibodies, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic or veterinary setting. All of these proteins are well defined in the literature and are so defined herein. Also included are deletion mutants of such proteins, individual domains of such proteins, fusion proteins made from such proteins, and mixtures of such proteins; particularly useful are those which have increased half-lives and/or increased activity.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing in co- and/or post-translational modifications of the polypeptide made in vivo or in vitro, for example, glycosylations, acetylations, phosphorylations, PEGylations and sulphations. In addition, protein fragments, analogs (including amino acids not encoded by the genetic code, e.g. homocysteine, ornithine, p-acetylphenylalanine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "codon bias" or "relative codon frequency" refers to the relative frequencies of use of codons that encode the same amino acid ("synonymous codons"). The bias may be naturally occurring, for example the codon bias in an organism's genome reflects the relative overall use of synonymous codons within all the genes in that organism. The bias may also be used in a computational algorithm, where for example it may be used to determine the relative frequency with which different synonymous codons are selected for use in designing a polynucleotide sequence. Similarly the "relative" frequency of any sequence element used to encode a polypeptide within a polynucleotide is the frequency with which that sequence element is used to encode a feature of the polypeptide, divided by the number of occurrences within the polypeptide in a given reading frame of features that could be encoded by that sequence element.

The terms "codon usage table" or "codon bias table" or "codon frequency lookup table" are used interchangeably to describe a table which correlates each codon that may be used to encode a particular amino acid, with the frequencies with which each codon is used to encode that amino acid in a specific organism, or within a specified class of genes within that organism, or within one or more synthetic polynucleotides. A "hybrid codon usage table" or "hybrid codon bias table" can also be constructed by combining two or more codon usage tables according to a variety of possible rules, some of which will be enumerated in more detail elsewhere herein.

The term "absolute codon frequency" refers to the frequency with which a codon appears relative to the total number of codons (e.g. both synonymous and non-synonymous codons) within a polynucleotide or set of polynucleotides in a given reading frame (e.g., the reading frame that is used to encode a protein). Similarly the "absolute" frequency of any sequence element used to encode a polypeptide within a polynucleotide is the frequency with which that sequence element is used to encode a feature (e.g., amino acid, amino acid pair, etc.) of the polypeptide, divided by the number of occurrences within the polypeptide of features of the same size as those that could be encoded by that sequence element.

The terms "threshold" or "cutoff" are used interchangeably to refer to the minimum allowable frequency in using a codon frequency lookup table. For example if a threshold or cutoff of 10% is set for an algorithm to use with a sequence element frequency lookup table, then no sequence elements with a value of less than 10% in that lookup table are accepted by the algorithm for subsequent polynucleotide design and synthesis. Thresholds may be expressed as percentages (e.g., the percentage of time that an organism or class of genes within an organism uses a specified codon to encode an amino acid)

or as frequencies (0.1 would be the frequency of codon usage that could also be expressed as 10%).

The term "splice variant" or "splicing variant" refers to the different possible RNA products that may be produced by a cell that transcribes a segment of DNA to produce an RNA molecule. These different products result from the action of the RNA splicing and transportation machinery, whose specificity of function differs from cell to cell, causing different signals within an RNA sequence to be recognized as intron donor and acceptor sites, and leading to different RNA products.

The term "expression system" refers to any in vivo or in vitro biological system that is used to produce one or more proteins encoded by a polynucleotide. Examples of expression systems include, but are not limited to E. coli, baculovirus, mammalian tissue culture, and plants such as maize or soybean.

The term "annealing temperature" or "melting temperature" or "transition temperature" refers to the temperature at which a pair of nucleic acids is in a state intermediate between being fully annealed and fully melted. The term refers to the behavior of a population of nucleic acids: the "annealing temperature" or "melting temperature" or "transition temperature" is the temperature at which 50% of the molecules are annealed and 50% are separate. Annealing temperatures can be determined experimentally. There are also methods well know in the art for calculating these temperatures.

The terms "codon space" and "codon sequence space" refer to all of the possible polynucleotide sequences that can be used to encode a specific polypeptide, by using different codons (nucleotide triplets) to encode each amino acid within the polypeptide.

The term "codon substitution" refers to a process of altering a polynucleotide sequence by changing one or more of the codons encoding one or more amino acids within a polypeptide, though without altering the sequence of the encoded polypeptide.

The term "codon variant set" refers to a set of polynucleotide sequences, each of which preferably encodes the same polypeptide or less preferably a set of highly similar polypeptides sharing at least 99% or 98% or 97% or 96% or 95% or 94% or 93% or 92% or 91% or 90% amino acid sequence identity to at least one other polypeptide in the set, but which use different codons at one or more positions within the sequence.

The term "polynucleotide sequence property" is used to describe a property that is a direct characteristic of a polynucleotide. Polynucleotide sequence properties include but are not limited to codon bias, the frequency with which specific codons are used, the GC content of all or a portion of the polynucleotide, the predicted secondary structure of the polynucleotide or its transcription product.

The term "expression property" is used to describe a property of a polynucleotide in an in vivo or in vitro expression system. Expression properties include but are not limited to the amount of RNA or protein produced and the amount of soluble or otherwise functional protein produced.

The term "codon expression relationship" is used to describe a relationship between one or more polynucleotide sequence properties and one or more expression properties.

The term "translation" refers to the process by which a polypeptide is synthesized by a ribosome 'reading' the sequence of a polynucleotide.

5.2 FACTORS AFFECTING PROTEIN EXPRESSION

Because of the degeneracy of the genetic code, one polypeptide sequence may be encoded by many different polynucleotides. Some of these polynucleotides will be easier to synthesize in a high fidelity process, while others will be more difficult. When a polynucleotide is being designed and/or synthesized to encode a polypeptide, a polynucleotide sequence may therefore be chosen that facilitates the high fidelity synthesis of that polynucleotide, in addition to ensuring that the polynucleotide will possess the desired expression properties. Methods for choosing a polynucleotide sequence that fulfills functional as well as ease-of-synthesis criteria may be accomplished using computer programs (e.g., software). The methods and the software for performing the methods are nonlimiting aspects of some embodiments of the present disclosure.

Factors that affect protein expression, the expression of soluble protein or the expression of active protein encoded by the polynucleotide fall into several classes, all of which can be influenced by the codons chosen to encode the amino acids of the polypeptide. First there are those that affect mRNA levels within the expression system. These include factors affecting the rate of production of mRNA including the RNA polymerase type used for transcription, the RNA polymerase level present in the expression system and the transcription promoter sequence used. The mRNA levels are also affected by the mRNA degradation rate, which are in turn influenced by mRNA destabilizing motifs, RNAse recognition sequences and polyA addition signals. The mRNA levels may also be affected by mRNA structures at the translational initiation site, at the ribosome binding site, at the start codon, around the initial 10-50 codons or elsewhere within of following the open reading frame, transcriptional termination motifs present before or within the open reading frame, signals within the transcribed sequence such as those that direct, alter or modify mRNA splicing and nuclear export. Second there are factors that affect the translational initiation rate. These include the sequence of the ribosome binding site, sequences upstream of the ribosome binding site, sequences around the start codon (for example Kozak consensus sequences), the presence, relative location and sequence of internal ribosome entry sites, the sequence and distance between the ribosome entry site or the ribosome binding site or the 5' end of the mRNA and the start codon, the mRNA structures at the translational initiation site, at the ribosome binding site, at the start codon, around the initial 10-50 codons, the sequence of the initial 10-20 codons, the GC bias of the initial 10-20 codons, the codon used at the codon adjacent to the start codon, the sequence of the start codon (AUG, WUG, or GUG), the ribosome concentration, the growth conditions before induction of expression, the growth conditions during expression, the temperature prior to induction of expression and the temperature during expression. Third there are factors that affect the rate of translational elongation. These include the level of charged tRNAs (Elf et al., 2003, "Selective charging of tRNA isoacceptors explains patterns of codon usage," Science 300, 1718-1722), which depend upon tRNA concentrations, tRNA charging rates and amino acid availability. They also include the rate of ribosomal tRNA selection (decoding rate) which depends upon the strength of the codon-anticodon interaction, the preceding codon (P-site codon), the wobble base of the preceding codon and the wobble base of the codon being read. Fourth are factors that affect ribosomal fidelity including those that influence ribosomal frameshifts such as homopolymer stretches, G/C islands, A/T islands and homopolymer stretches near pause sites. Fifth are peptides that are hindered in the ribosomal exit channel, which depend in part upon the amino acid sequence of the initial 10-20 amino acids.

Particularly useful methods for designing polynucleotides are those that integrate functional constraints such as the selection of codons that will express well in one or more chosen host systems, the elimination of unwanted restriction sites and the inclusion of desired restriction sites, with synthesis constraints such as the elimination of repeated sequence elements and the balancing of GC content throughout the sequence.

5.3 DESIGNING POLYNUCLEOTIDES USING FREQUENCY LOOKUP TABLES

Most organisms use the same genetic code, that is, in general the same triplet of nucleotides (codon) specifies the same amino acid. Different organisms use these codons with different frequencies within their genes, however. For example different codon biases are found in humans, human viruses such as hepatitis A, hepatitis B, hepatitis C, human immunodeficiency virus (HIV), human papilloma virus (HPV), influenza, flaviviruses, lentiviruses, papovaviruses, human pathogens such as *Mycobacteria, Chlamydomonas, Candida, Plasmodium falciparum* (the causative agent of malaria), *Cryptosporidium, Leishmania* and other protozoa, model organisms such as Tetrahymena, *Arabidopsis, Xenopus, Ralstonia, Drosophila, Caenorhabditis elegans,* and commonly used expression systems such as baculovirus, *Escherichia coli, Bacillus, Pseudomonas species, Salmonella species, Streptomyces* species, filamentous fungi, mammalian cell lines including COS cells, Chinese Hamster Ovary cells and fibroblasts including 3T3 cells, insect cell lines such as those derived from *Spodptera* species, yeasts including *Saccharomyces, Pichia, Klebsiella* and *Candida* species, plants including maize, soybean and cotton and model organisms for the study of disease and tests of the efficacies of DNA vaccines such as macaques, mice, rats, guinea pigs, sheep, goats and rabbits, in vitro expression systems prepared from extracts of living cells, in vitro expression systems prepared by assembly of purified individual components.

In the systems and methods disclosed herein, frequency lookup tables are constructed to represent the distribution of codons within a set of synthetically designed genes that may share one or more properties such as the level of expressed protein, the level of expressed soluble protein or the level of expressed active protein. For example, a set of synthetically designed and constructed genes may be experimentally tested in an expression host, and the genes may then be categorized according to one or more functional properties. The frequencies with which different codons are used to encode each amino acid may be calculated for the synthetic genes that perform the best, for example those that express the most protein, or those that express the most soluble protein, or those that express the most active protein. These frequencies can then be used directly in the design of polynucleotides, or they may be incorporated into lookup tables that can then be used in the design of polynucleotides.

In some embodiments, codons that are very rarely used in a specific host are eliminated from a frequency lookup table. For example Arg is encoded by six possible codons: CGG, CGA, CGT, CGC, AGG and AGA. Of these, codons CGG, CGA, AGA and AGG each occur only about 1% of the time in highly expressed *E. coli* genes, while CGT occurs 64% of the time and CGC 33% of the time. It may be advantageous to eliminate the four rarely used codons from the synthetic polynucleotide entirely. In this case only CGT and CGC would be used to encode Arg in the synthetic polynucleotide.

Threshold values for codons may be selected such that a codon that appears less frequently in a frequency lookup table than that threshold value are not used in a polynucleotide for expression in that host. Threshold values of 0.1 (10%), 0.09 (9%), 0.08 (8%), 0.07 (7%), 0.06 (6%), 0.05 (5%) and 0.04 (4%) can all be useful, where such threshold values represent the minimum frequency value for a codon in a frequency lookup table that allows the respective codon to be used in designing a synthetic polynucleotide. Threshold values can be set using a method in which codons are selected probabilistically based upon a frequency lookup table, then codons whose frequency is below the threshold are discarded and another codon is chosen, again probabilistically. Alternatively a codon frequency lookup table may be pre-calculated with the frequency for a codon that appears below the threshold frequency being set to zero so that it is never selected by a probabilistic selection method.

Hybrid frequency lookup tables may be constructed for designing a polynucleotide encoding a polypeptide to be expressed in more than one expression system. One method of constructing such hybrid frequency lookup tables is to combine two or more starting frequency lookup tables from one or more organism. In one combination method, a threshold frequency is selected and any codons that fall below the threshold are eliminated from all of the starting frequency lookup tables (where the threshold frequency refers to the minimum frequency value for a codon in a frequency lookup table that allows the respective codon to be used in designing a synthetic polynucleotide). For the remaining codons there are several possible methods of processing the frequencies. An average of the frequency ranges in the starting frequency lookup tables may be obtained. Alternatively the higher of the frequency ranges may be selected for each of the codons. Another possibility is to select the lower of the frequency ranges for each of the codons. In all cases, such combined lookup frequency lookup tables should be used in such a way that the sum of the frequencies for all codons that encode one amino acid are equal to 1. By avoiding low frequency codons for multiple organisms, expression in all of those organisms may be improved, thereby increasing the general usefulness of the synthetic polynucleotide. As used herein, a frequency range refers to a continuous set of values (e.g., frequency of occurrence of a codon, frequency of occurrence of a sequence element) bounded by a maximum percent occurrence and a minimum percent occurrence. In other words, a frequency range refers to any and all values (e.g., frequency of occurrence of a codon, frequency of occurrence of a sequence element) that fall between a maximum percent occurrence and a minimum percent occurrence, in addition to the maximum percent occurrence and a minimum percent occurrence.

Because codon biases from conventional studies contain average values compiled from information from more than one gene, the codon distribution for any one gene may not precisely match the values found in the conventional studies, even if the codon distribution in a gene was in part used to calculate the codon biases. Conversely the codon bias within a polynucleotide may not precisely match the codon preferences from conventional studies, even if the codon biases from such studies were used to design the polynucleotide, for example if the codon biases from a study were used to guide a probabilistic choice of codons to represent each amino acid. For example, in designing a polynucleotide to encode a polypeptide with an *E. coli* codon bias, each time a Tyr is encountered, a selection method or computer program may be used that has a 35 percent chance of selecting TAT and a 65 percent chance of selecting TAC. On average, many polynucleotides designed by such a method would contain TAT and TAC in the ratio of 0.35 to 0.65, although any individual polynucleotide may vary from this ratio. Similar methods may be used to select codons to encode the other amino acids from the polypeptide.

It is possible to make the codon distribution in a polynucleotide very closely match the frequencies in a frequency lookup table (whether derived from natural sequences or from synthetic sequences). One way in which this can be done is to select an initial polynucleotide sequence, and then to calculate the codon distribution within this initial polynucleotide sequence. Codons in the polynucleotide sequence can then be changed until the codon distributions within it are as close as desired to a specified frequency lookup table. There are many ways to achieve this kind of iterative sequence optimization. For example, codons can be selected at random, a change can be proposed at random and the change can be accepted if it produces a codon distribution that is closer to the one desired. Codons may also be selected in a directed way. For example, codons in a specific part of the polynucleotide, codons encoding specific amino acids, codons with a specific GC bias, codons with a specified wobble base may be preferentially selected for replacement or may be preferentially withheld from replacement.

This kind of Monte Carlo algorithm may generally be used to modify any other quantifiable (including binary or Boolean) polynucleotide sequence property or combination of properties. The inventive steps are (1) select an initial codon sequence to encode a polypeptide; (2) quantify the one or more polynucleotide sequence properties of interest; (3) identify a possible change to the codon sequence that does not change the encoded polypeptide; (4) quantify the one or more polynucleotide sequence properties of interest for the polynucleotide sequence after the change in codon sequence; (5) accept or reject the change based on a function of the difference in values for the one or more polynucleotide properties of interest for the original and the unchanged codon sequences; and (6) repeat this process until a desired value for the one or more polynucleotide sequence properties of interest is obtained. Searches for codon sequences that have defined values for one or more quantifiable polynucleotide sequence properties can also be performed by evolving the sequence using genetic algorithms or genetic algorithms in combination with monte carlo algorithms, or other stochastic searches such as simulated annealing, Boltzmann learning, etc. See for example Duda et al., 2001, *Pattern Classification*, Second Edition, John Wiley & Sons, Inc., New York, which is hereby incorporated by reference herein for such purpose.

In preferred embodiments of the invention, the design of polynucleotide sequences with one or more quantifiable polynucleotide sequence property is performed using a computer program.

5.4 DESIGN OF CODON VARIANT SETS

The methods disclosed herein may be used to determine at least one property that affects an expression property value of polynucleotides in an expression system. There are many factors that may affect the levels of expression of a polypeptide by translation of a polynucleotide, or the levels of expression of soluble polypeptide by translation of a polynucleotide, or the levels of expression of active polypeptide by translation of a polynucleotide. Some of these factors can be significantly influenced by the choice of codons used to encode the polypeptide, so that the final level of polypeptide expressed, or soluble polypeptide expressed, or active polypeptide expressed can be increased 2-fold, or 5-fold or 10-fold or 100-fold by modifying the codons used to encode a polypeptide. It may not be possible to deduce which codons will result in improved performance of a polynucleotide by considering the biochemistry of the translation process, or of other cellular or biochemical processes that affect translation. Furthermore, different expression systems may differ in the precise details of translation (the concentrations of different tRNAs present in a cell, or the rate at which each tRNA is charged with the appropriate amino acid, for example), so that the codons that may result in high levels of polypeptide expression in one expression system may not do so when used in another expression system.

In cases where it is not possible to assign values to different codons in an expression system of interest based on a mechanistic understanding of the process, it is possible to elucidate the effect of codon choices by constructing a plurality of polynucleotides, where the plurality of polynucleotides comprises, for example, five or more polynucleotides, ten or more polynucleotides, twenty or more polynucleotides, fifty or more polynucleotides, 100 or more polynucleotides, between ten and 250 polynucleotides, or more than 1000 polynucleotides. In some embodiments, each polynucleotide in the plurality of polynucleotides encodes a polypeptide sequence that is at least seventy-five percent identical, at least eighty percent identical, at least eighty-five percent identical, at least ninety percent identical, or at least ninety-five percent identical to at least one other polypeptide sequence encoded by a different polynucleotide in the plurality of polynucleotides.

In some embodiments, for each respective amino acid in a plurality of amino acids comprising five or more amino acids, a relative frequency of each of a plurality of synonymous codons for the respective amino acid is varied in a region of each of two or more of the polynucleotides in the plurality of polynucleotides that encodes a polypeptide sequence that is at least ninety-five percent identical to the polypeptide sequence encoded by a first polynucleotide. In some embodiments, for each respective amino acid in a plurality of amino acids comprising five or more amino acids, a relative frequency of each of a plurality of synonymous codons for the respective amino acid is varied in a region of each of two or more of the polynucleotides in the plurality of polynucleotides that encodes a polypeptide sequence that is at least ninety-five percent identical to at least one other polypeptide sequence encoded by a different polynucleotide in the plurality of polynucleotides.

In some embodiments, for each respective amino acid in a plurality of amino acids comprising two or more amino acids, a relative frequency of each of a plurality of synonymous codons for the respective amino acid is varied in a region of each of five or more of the polynucleotides in the plurality of polynucleotides that encodes a polypeptide sequence that is at least ninety-five percent identical to the polypeptide sequence encoded by a first polynucleotide. In some embodiments, for each respective amino acid in a plurality of amino acids comprising two or more amino acids, a relative frequency of each of a plurality of synonymous codons for the respective amino acid is varied in a region of each of five or more of the polynucleotides in the plurality of polynucleotides that encodes a polypeptide sequence that is at least ninety-five percent identical to at least one other polypeptide sequence encoded by a different polynucleotide in the plurality of polynucleotides.

In some embodiments, for each respective amino acid in a plurality of amino acids comprising between two and fifteen amino acids, a relative frequency of each of a plurality of synonymous codons for the respective amino acid is varied in a region of each of five or more of the polynucleotides in the plurality of polynucleotides that encodes a polypeptide sequence that is at least eighty, at least eighty-five, at least ninety, at least ninety-five, at least ninety-eight, or at least ninety-nine percent identical to the polypeptide sequence encoded by a first polynucleotide. In some embodiments, for each respective amino acid in a plurality of amino acids comprising between two and fifteen amino acids, a relative frequency of each of a plurality of synonymous codons for the respective amino acid is varied in a region of each of five or more of the polynucleotides in the plurality of polynucleotides that encodes a polypeptide sequence that is at least eighty, at least eighty-five, at least ninety, at least ninety-five, at least ninety-eight, or at least ninety-nine percent identical to at least one other polypeptide sequence encoded by a different polynucleotide in the plurality of polynucleotides.

In some embodiments, for each respective amino acid in a plurality of amino acids comprising five or more amino acids, a relative frequency of each of a plurality of synonymous codons for a respective amino acid is varied in a region of each of five or more of the polynucleotides in the plurality of polynucleotides that encodes a polypeptide sequence that is at least ninety-five percent identical to the polypeptide sequence encoded by a first polynucleotide. In some embodiments, for each respective amino acid in a plurality of amino acids comprising five or more amino acids, a relative frequency of each of a plurality of synonymous codons for a respective amino acid is varied in a region of each of five or more of the polynucleotides in the plurality of polynucleotides that encodes a polypeptide sequence that is at least ninety-five percent identical to at least one other polypeptide sequence encoded by a different polynucleotide in the plurality of polynucleotides.

As used, herein, computation of percent identity takes full weight of any insertions in two sequences for which percent identity is computed. To compute percent identity between two sequences, they are aligned and any necessary insertions in either sequence being compared are then made in accordance with sequence alignment algorithms known in the art. Then, the percent identity is computed, where each insertion in either sequence necessary to make the optimal alignment between the two sequences is counted as a mismatch.

In a preferred embodiment, a first amino acid is encoded a first plurality of times (e.g., two or more times, three or more times, four or more times, more than ten times, or between two and one hundred times) in both the first polynucleotide and in a second polynucleotide in the plurality of polynucleotides. For example, the first amino acid may be alanine, or any other naturally occurring amino acid that are encoded by a plurality of synonymous codons including a first codon. In some embodiments, the plurality of synonymous codons is two or more codons, three or more codons, four or more codons, five or more codons, or six codons. In some embodiments, this first codon is present in the first polynucleotide with a first frequency relative to all other codons in the plurality of synonymous codons in the first polynucleotide. For example, consider the case where there are four synonymous codons for the first amino acid, where the four synonymous codons include the first codon. In some embodiments, the first frequency refers to the percentage of time the first codon is used in a polynucleotide (e.g., the first polynucleotide) relative to the percentage of the time all other codons in the set of four synonymous codons are used in the same polynucleotide in the reading frame that encodes the polypeptide sequence. Thus, if the first amino acid appears ten times in the first polynucleotide in the reading frame that encodes the polypeptide sequence under study, and the first codon is used to encode three instances of the first amino acid in the polypeptide sequence, the relative frequency of the first codon in the first polynucleotide is 0.30.

The first codon is also present in the second polynucleotide with a second frequency relative to all other codons in the plurality of synonymous codons in the second polynucleotide. Further still, the first frequency is different than the second frequency. Thus, if the relative frequency of the first codon in the first polynucleotide is 0.30, then the relative frequency of the first codon in the second polynucleotide must be some value other than 0.30.

In some embodiments, the plurality of nucleotides is constructed using frequency lookup tables. Such frequency lookup tables specify the allowed frequency range (e.g., on an absolute basis relative to the total number of codons in the coding reading frame or on a relative basis with respect to the number of synonymous codons in the coding reading frame) for each of a plurality of codons. In fact, in some embodiments, two or more frequency lookup tables can be used to construct the plurality of nucleotides. In one exemplary embodiment, the first polynucleotide described above is constructed using a first frequency lookup table, where the first frequency lookup table specifies a first target frequency range for the use of the first codon relative to all other codons in the plurality of synonymous codons in a polynucleotide and where the first frequency described above is within the first target frequency range. Further, the second polynucleotide described above is encoded using a second frequency lookup table, where the second frequency lookup table specifies a second target frequency range for the use of the first codon relative to all other codons in the plurality of synonymous codons in a polynucleotide and where the second frequency described above is within the second target frequency range. In this embodiment, the first target frequency range is different from the second target frequency target range. For instance, the first target frequency range may be 0.25 to 0.75 whereas the second target frequency range may be 0.45 to 0.90. Two frequency ranges are considered different herein if they have at least one different maximum or at least one different minimum. In some embodiments, more than two frequency lookup tables are used to construct the plurality of polynucleotides. For instance, referring to the example above where two different codon frequency tables were used, in some embodiments a third frequency lookup table specifies a third target frequency range for the use of the first codon relative to all other codons in the plurality of synonymous codons in a third polynucleotide in the plurality of polynucleotides.

In another exemplary aspect of the invention, an embodiment of the constructing step provides a first frequency lookup table that specifies a corresponding respective target frequency range for each codon in a first plurality of codons, each corresponding respective target frequency range specifying a target frequency range for a codon in the first plurality of codons to be used to encode a corresponding amino acid in an amino acid sequence relative to all other codons that are capable of encoding the corresponding amino acid, and where, for each respective codon in the first codon frequency table, the constructing step discussed above further comprises choosing a respective frequency that the respective codon is to be used to encode the amino acid encodable by the respective codon throughout an amino acid sequence encoded by the first polynucleotide in the plurality of polynucleotides relative to all other codons capable of encoding the amino acid, where the respective frequency is within the frequency range specified in the first frequency lookup table for the respective codon. A second frequency lookup table specifies a corresponding respective target frequency range for each codon in a second plurality of codons, each corresponding respective target frequency range specifying a target frequency range for a codon in the second plurality of codons to be used to encode a corresponding amino acid in an amino acid sequence relative to all other codons that are capable of encoding the corresponding amino acid and where, for each respective codon in the second frequency lookup table, the constructing step discussed above further comprises choosing a respective frequency that the respective codon is to be used to encode the amino acid encodable by the respective codon throughout an amino acid sequence encoded by the second polynucleotide in the plurality of polynucleotides relative to all other codons capable of encoding the amino acid, where the respective frequency is within the frequency range specified in the second frequency lookup table for the respective codon. In this exemplary embodiment, the first frequency used to encode the first codon in the first polynucleotide is within a frequency range specified for the first amino acid by the first frequency lookup table and the second frequency used to encode the first codon in the second polynucleotide is within a frequency range specified for the first amino acid by the second frequency lookup table. In some embodiments the first plurality of codons of the first frequency lookup table includes codons that are not present in the second plurality of codons of the second frequency lookup table. In some embodiments, the first plurality of codons of the first frequency lookup table is identical to the second plurality of codons of the second frequency lookup table.

In some embodiments, two or more different frequency lookup tables can be used to construct a polynucleotide in the plurality of polynucleotides. For example, in some embodiments, two different frequency lookup tables are used to construct the first polynucleotide described above. In such embodiments, a first set of positions in the first polynucleotide are encoded using a first frequency lookup table, where the first frequency lookup table specifies a first target frequency range for the use of a predetermined codon, relative to all other codons that are synonymous to the predetermined codon, in the first set of positions in the first polynucleotide that encode a predetermined amino acid. Furthermore in these exemplary embodiments, a second set of positions in the first polynucleotide are encoded using a second frequency lookup table, where the second frequency lookup table specifies a second target frequency range for the use of the predetermined codon, relative to all other codons that are synonymous to the predetermined codon, in the second set of positions in the first polynucleotide that encode the predetermined amino acid. Further, the first set of positions does not include positions in the second set of positions and the second set of positions does not include positions in the first set of positions. An example of a first set of positions are all positions in the reading frame of the polynucleotide that code for an alanine in the N-terminal half of the encoded polypeptide sequence. An example of a second set of positions are all positions in the reading frame of the polynucleotide that code for an alanine in the C-terminal half of the encoded polypeptide sequence. In some instances in accordance with such embodiments, the predetermined amino acid can be encoded by two or more synonymous codons, three or more synonymous codons, four or more synonymous codons, five or more synonymous codons, or six synonymous codons.

In some embodiments, multiple codon frequency tables are used and each such codon frequency table provides a target frequency range for each of a plurality of codons (e.g., two or more codons, three or more codons, four or more codons, five or more codons, ten or more codons, fifteen or more codons, or twenty or more codons). For example, in one example, a first frequency lookup table specifies a corresponding respective first target frequency range for each codon in a first plurality of codons (e.g., two or more codons, three or more codons, four or more codons, five or more codons, ten or more codons, fifteen or more codons, or twenty or more codons), each corresponding respective first target frequency range specifying a first target frequency range for a codon in the first plurality of codons to be used to encode a corresponding amino acid in an amino acid sequence relative to all other codons that are capable of encoding the corresponding amino acid, and where for each respective codon in the first frequency lookup table, the constructing discussed above further comprises choosing a respective first frequency that the respective codon is to be used to encode the amino acid encodable by the respective codon in a predetermined first set of positions in the amino acid sequence encoded by the first polynucleotide in the plurality of polynucleotides relative to all other codons capable of encoding the amino acid, where the respective first frequency is within the first target frequency range specified in the first frequency lookup table for the respective codon. Further, a second frequency lookup table specifies a corresponding respective second target frequency range for each codon in a second plurality of codons, each corresponding respective second target frequency range specifying a second target frequency range for a codon in the second plurality of codons to be used to encode a corresponding amino acid in an amino acid sequence relative to all other codons that are capable of encoding the corresponding amino acid and where, for each respective codon in the second frequency lookup table, the constructing discussed above further comprises choosing a respective second frequency that the respective codon is to be used to encode the amino acid encodable by the respective codon in a predetermined second set of positions in the amino acid sequence encoded by the first polynucleotide in the plurality of polynucleotides relative to all other codons capable of encoding the amino acid, where the respective second frequency is within the second target frequency range specified in the second frequency lookup table for the respective codon. In some embodiments the first plurality of codons of the first frequency lookup table includes codons that are not present in the second plurality of codons of the second frequency lookup table. In some embodiments, the first plurality of codons of the first frequency lookup table is identical to the second plurality of codons of the second frequency lookup table.

In some embodiments, multiple codon frequency tables are used and each such codon frequency table provides a target frequency range for each of a plurality of codons (e.g., two or more codons, three or more codons, four or more codons, five or more codons, ten or more codons, fifteen or more codons, or twenty or more codons), where the frequency range for a given codon is relative to all other expressed codons in the reading frame of a polynucleotide, not just synonymous codons. For example, one embodiment provides a first frequency lookup table that specifies a corresponding respective first target frequency range for each codon in a first plurality of codons, each corresponding respective first target frequency range specifying a first target frequency range for a codon in the first plurality of codons to be used to encode a corresponding amino acid in an amino acid sequence relative to all other expressed codons in the polynucleotide, and where for each respective codon in the first codon frequency table, the constructing step described above further comprises choosing a respective first frequency that the respective codon is to be used to encode the amino acid encodable by the respective codon throughout the amino acid sequence encoded by the first polynucleotide in the plurality of polynucleotides relative to all other expressed codons in the first polynucleotide, where the respective first frequency is within the first target frequency range specified in the first frequency lookup table for the respective codon Furthermore, a second frequency lookup table specifies a corresponding respective second target frequency range for each codon in a second plurality of codons, each corresponding respective second target frequency range specifying a second target frequency range for a codon in the second plurality of codons to be used to encode a corresponding amino acid in an amino acid sequence relative to all other expressed codons in the polynucleotide, and where for each respective codon in the second frequency lookup table, the constructing discussed above further comprises choosing a respective second frequency that the respective codon is to be used to encode the amino acid encodable by the respective codon throughout the amino acid sequence encoded by said second polynucleotide in the plurality of polynucleotides relative to all other expressed codons in the second polynucleotide, where the second respective frequency is within the second target frequency range specified in the second frequency lookup table for the respective codon. In this embodiment the first frequency used to encode a first codon in the first polynucleotide is within a first target frequency range specified for the first amino acid by the first frequency lookup table. Furthermore, the second frequency used to encode the first codon present in the second polynucleotide is within a second target frequency range specified for the first amino acid by the second frequency lookup table.

In the inventive methods, each respective polynucleotide in the plurality of polynucleotides is expressed individually in an expression system. In some embodiments, this involves synthesizing each of the polynucleotides in the plurality of polynucleotides, inserting each polynucleotide into a separate expression vector, and expressing the polynucleotide in the expression vector separately in the expression system. Examples of expression systems that can be used have been given above and include, for example, *E. coli* and baculovirus and yeast and mammalian tissue culture and plants such as maize or soybean.

Next, an expression property value of each respective polynucleotide in the plurality of polynucleotides in the expression system is measured, thereby determining at least one property that affects an expression property of polynucleotides in the expression system, where the at least one property is an effect that a frequency of use of one or more codons in a plurality of naturally occurring codons has on the expression property values of polynucleotides in the expression system.

Standard techniques may be utilized to measure the expression property value of each respective polynucleotide in the plurality of polynucleotides. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine an expression property value of a respective polynucleotide (e.g., an amount of a protein encoded by the respective polynucleotide) in the plurality of polynucleotides present in an expression system. Other methods for detection of specific polypeptides include mass spectroscopy and mass spectroscopy of protein samples that have been treated with one or more site specific proteases to produce polypeptide fragments which can be uniquely identified by mass spectroscopy. One exemplary agent for detecting a protein of interest is an antibody capable of specifically binding to a protein of interest, preferably an antibody detectably labeled, either directly or indirectly.

For such detection methods, if desired, a protein from the expression system to be analyzed can easily be isolated using techniques which are well known to those of skill in the art. Protein isolation methods can, for example, be such as those described in Harlow and Lane, 1988, *Antibodies: A Laboratory Manual*, Cold Spring Harbor Laboratory Press (Cold Spring Harbor, N.Y.), which is incorporated by reference herein in its entirety.

In certain embodiments, methods of detection of the protein expressed from a respective polynucleotide in the plurality of polynucleotides in the expression system involve detection via interaction with a protein-specific antibody. For example, antibodies directed to a protein of interest (e.g., a protein expressed from a respective polynucleotide in the plurality of polynucleotides). Antibodies can be generated utilizing standard techniques well known to those of skill in the art. In specific embodiments, antibodies can be polyclonal, or more preferably, monoclonal. An intact antibody, or an antibody fragment (e.g., scFv, Fab or $F(ab')_2$) can, for example, be used.

For example, antibodies, or fragments of antibodies, specific for a protein of interest can be used to quantitatively or qualitatively detect the presence of a protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by applying to an expression system (used to express a protein from a respective polynucleotide in the plurality of polynucleotides) a labeled antibody that is directed to the protein. The antibody (or fragment) is preferably applied by overlaying the antibody (or fragment) onto the expression system.

Immunoassays for a protein of interest typically comprise incubating an expression system with a detectably labeled antibody capable of identifying a protein of interest, and detecting the bound antibody by any of a number of techniques well-known in the art. The term "labeled" can refer to direct labeling of the antibody via, e.g., coupling (e.g., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The expression system in which a respective polynucleotide in the plurality of polynucleotides is expressed can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod.

Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio (ed.), 1980, *Enzyme Immunoassay*, CRC Press, Boca Raton, Fla.; Ishikawa et al., (eds.), 1981, *Enzyme Immunoassay*, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, 1986, *Principles of Radioimmunoassays*, Seventh Training Course on Radioligand Assay Techniques, The Endocrine Society, which is hereby incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In some embodiments, a protein chip assay (e.g., THE PROTEINCHIP® Biomarker System, Ciphergen, Fremont, Calif.) is used to measure an expression property value of a respective polynucleotide in the expression system. See also, for example, Lin, 2004, Modern Pathology, 1-9; Li, 2004, Journal of Urology 171, 1782-1787; Wadsworth, 2004, Clinical Cancer Research, 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, each of which is hereby incorporated by reference in its entirety. Protein chip assays (protein microarrays) are commercially available. For example, Ciphergen (Fremont, Calif.) markets the PROTEINCHIP® System Series 4000 for quantifying proteins in a sample. Furthermore, Sigma-Aldrich (Saint Lewis, Mo.) sells a number of protein microarrays including the PANORAMA™ Human Cancer v1 Protein Array, the PANORAMA™ Human Kinase v1 Protein Array, the PANORAMA™ Signal Transduction Functional Protein Array, the PANORAMA™ AB Microarray—Cell Signaling Kit, the PANORAMA™ AB Microarray—MAPK and PKC Pathways kit, the PANORAMA™ AB Microarray—Gene Regulation I Kit, and the PANORAMA™ AB Microarray—p53 pathways kit. Further, TeleChem International, Inc. (Sunnyvale, Calif.) markets a Colorimetric Protein Microarray Platform that can perform a variety of micro multiplexed protein microarray assays including microarray based multiplex ELISA assays. See also, MacBeath and Schreiber, 2000, "Printing Proteins as Microarrays for High-Throughput Function Determination," Science 289, 1760-1763, which is hereby incorporated by reference herein in its entirety.

In some embodiments, a bead assay is used to measure an expression property value of a respective polynucleotide in the expression system. One such bead assay is the Becton Dickinson Cytometric Bead Array (CBA). CBA employs a series of particles with discrete fluorescence intensities to simultaneously detect multiple soluble analytes. CBA is combined with flow cytometry to create a multiplexed assay. The Becton Dickinson CBA system, as embodied for example in the Becton Dickinson Human Inflammation Kit, uses the sensitivity of amplified fluorescence detection by flow cytometry to measure soluble analytes in a particle-based immunoassay. Each bead in a CBA provides a capture surface for a specific protein and is analogous to an individually coated well in an ELISA plate. The BD CBA capture bead mixture is in suspension to allow for the detection of multiple analytes in a small volume sample.

In some embodiments the multiplex analysis method described in U.S. Pat. No. 5,981,180, herein incorporated by reference in its entirety, and in particular for its teachings of the general methodology, bead technology, system hardware and antibody detection, is used to measure an expression property value of a respective polynucleotide in the expression system. For this analysis, a matrix of microparticles is synthesized, where the matrix consists of different sets of microparticles. Each set of microparticles can have thousands of molecules of a distinct antibody capture reagent immobilized on the microparticle surface and can be color-coded by incorporation of varying amounts of two fluorescent dyes. The ratio of the two fluorescent dyes provides a distinct emission spectrum for each set of microparticles, allowing the identification of a microparticle a set following the pooling of the various sets of microparticles. U.S. Pat. Nos. 6,268,222 and 6,599,331 also are incorporated herein by reference in their entirety, and in particular for their teachings of various methods of labeling microparticles for multiplex analysis.

In some embodiments an assay that distinguishes between soluble and insoluble polypeptides is used to measure an expression property value of a respective polynucleotide in the expression system. Such assays may incorporate centrifugation or filtration or chromatographic steps to separate soluble polypeptides encoded by a polynucleotide from insoluble polypeptides encoded by a polynucleotide.

In some embodiments, the frequency of use of one or more codons is the relative frequency of use of the one or more codons with respect to the use of synonymous codons in the reading frame of each of the polynucleotides in the plurality of polynucleotides that encode the polypeptide sequence under study. For example, consider the case where the one or more codons is in fact, a single codon. In this case, the frequency of use of the one codon refers to the relative frequency with which the one codon is used to encode all instances of the amino acid corresponding to the one codon in the reading frame of each of polynucleotides that encodes the polypeptide under study, relative to the use of all other synonymous codons in the reading frame of each of polynucleotides that encodes the polypeptide under study.

In some embodiments, the frequency of use of one or more codons is the absolute frequency of use of the one or more codons with respect to the total number of codons in the reading frame of each of the polynucleotides in the plurality of polynucleotides that encode the polypeptide sequence under study. For example, consider the case where the one or more codons is in fact, a single codon. In this case, the absolute frequency of use of the one codon refers to the frequency with which the one codon is used in the reading frame of each of polynucleotides that encodes the polypeptide under study, relative to the total number of all codons in the reading frame of each of polynucleotides that encodes the polypeptide under study.

In some embodiments the expression property value of the respective polynucleotide in the plurality of polynucleotides in the expression system is a total amount of protein encoded by the respective polynucleotide that is expressed in the expression system in a predetermined period of time. In some embodiments, the expression property value of the respective polynucleotide in the expression system is a total amount of active protein encoded by the respective polynucleotide that is expressed in the expression system in a predetermined period of time. In some embodiments, the expression property of the respective polynucleotide in the expression system is a total amount of soluble protein encoded by the respective polynucleotide that is expressed in the expression system in a predetermined period of time. As used here, the predetermined period of time is application dependent and generally refers to a period of time after the polynucleotide has been introduced into the expression system (e.g., by transfection of an expression vector). For example, as used here, the predetermined period of time can be five minutes or more, twenty minutes or more, one hour or more, four hours or more, or less than two days after the respective polynucleotide has been introduced into the expression system and the expression system has been put under conditions that permit protein expression.

Another aspect provides a method of determining at least one property that affects an expression property value of polynucleotides in an expression system, the method comprising constructing a plurality of polynucleotides, wherein the plurality of polynucleotides comprises five or more polynucleotides, ten or more polynucleotides, twenty or more polynucleotides, between five and one hundred polynucleotides, or more than one thousand polynucleotides, each polynucleotide in the plurality of polynucleotides encoding a polypeptide sequence that is at least ninety-five percent identical to at least one other polypeptide sequence encoded by a different polynucleotide in the plurality of polynucleotides where (i) a first amino acid is encoded a first plurality of times in both the first polynucleotide and in a second polynucleotide in the plurality of polynucleotides, (ii) the first amino acid is encodable by a plurality of synonymous codons including a first codon, (iii) the first codon is present in the first polynucleotide with a first frequency, (iv) the first codon is present in the second polynucleotide with a second frequency, and (v) the first frequency is different than the second frequency. Further in the method, each respective polynucleotide in the plurality of polynucleotides is expressed individually in the expression system. Further in the method, an expression property value of each respective polynucleotide in the plurality of polynucleotides in the expression system is measured thereby determining at least one property that affects an expression property value of polynucleotides in the expression system, where the at least one property is an effect that a frequency of use of one or more codons in a plurality of naturally occurring codons has on the expression property values of polynucleotides in the expression system, where a first frequency lookup table specifies a corresponding respective first target frequency range for each codon in a first plurality of codons, each corresponding respective first target frequency range specifying a first target frequency range for a codon in the first plurality of codons to be used to encode a corresponding amino acid in an amino acid sequence relative to all other expressed codons in the polynucleotide, and wherein for each respective codon in the first frequency lookup table, the constructing further comprises choosing a respective first frequency that the respective codon is to be used to encode the amino acid encodable by the respective codon throughout the amino acid sequence encoded by said first polynucleotide in the plurality of polynucleotides relative to all other expressed codons in the first polynucleotide, wherein the respective first frequency is within the first target frequency range specified in the first frequency lookup table for the respective codon; and a second frequency lookup table specifies a corresponding respective second target frequency range for each codon in a second plurality of codons, each corresponding respective second target frequency range specifying a second target frequency range for a codon in the second plurality of codons to be used to encode a corresponding amino acid in an amino acid sequence relative to all other expressed codons in the polynucleotide, and wherein for each respective codon in the second frequency lookup table, the constructing further comprises choosing a respective second frequency that the respective codon is to be used to encode the amino acid encodable by the respective codon throughout the amino acid sequence encoded by said second polynucleotide in the plurality of polynucleotides relative to all other expressed codons in the second polynucleotide, where the second respective frequency is within the second target frequency range specified in the second frequency lookup table for the respective codon. In some embodiments, for each respective amino acid in a plurality of amino acids comprising five or more amino acids, a relative frequency of each of a plurality of synonymous codons for a respective amino acid is varied in a region of each of five or more of the polynucleotides in the plurality of polynucleotides that encodes a polypeptide sequence that is at least ninety-five percent identical to at least one other polypeptide sequence encoded by a different polynucleotide in the plurality of polynucleotides The plurality of polynucleotides, in which each polynucleotide encodes the same polypeptide sequence (or variants thereof having the requisite percent identity as described above) but differ in the codons used to encode that polypeptide sequence at one or more positions within the polynucleotide is referred to herein as a codon variant set. The sequences of the polynucleotides comprising the codon variant set, or one or more of the polynucleotide sequence properties of the polynucleotide sequences in the codon variant set (properties including but not limited to the codon bias, the relative or absolute frequency with which specific codons are used, the GC content of the polynucleotide, the predicted mRNA secondary structure of the polynucleotide) can then be correlated with one or more properties (e.g., expression properties) of the polynucleotide such as the levels of expression of a polypeptide by translation of the polynucleotide in an expression system, or the levels of expression of soluble polypeptide by translation of the polynucleotide in an expression system, or the levels of expression of a biologically or chemically active polypeptide by translation of the polynucleotide in an expression system. Such correlation can be achieved manually. For example, an expression property of each of the polynucleotides in the plurality of polynucleotides can be compared to the codon usage in each of the polynucleotides in order to ascertain a relationship between codon usage (e.g., codon frequency) and the expression property. Such correlation can also be achieved using pattern classification methods or statistical methods. Examples of pattern classification methods or statistical methods include, but are not limited to linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification*, Second Edition, John Wiley & Sons, Inc., New York; Hastie, 2003, *The Elements of Statistical Learning*, Springer, New York; and Agresti 1996, *An Introduction to Categorical Data Analysis*, John Wiley & Sons, New York, each of which is hereby incorporated by reference herein for such purpose. Such modeling or correlation can then be used to assign values for the different codons in the expression system of interest. The design and synthesis of a codon variant set and measurement of an expression property of the polynucleotides within a codon variant set for the purpose of evaluating different codon choices within an expression system is an aspect of the present invention.

The method of systematic variation of codon usage and analysis of expression is conceptually quite different from previous methods described in the art, and is an aspect of the present invention. These previous methods have used weak correlations between the codon biases found in and the expression levels observed for natural genes to derive rules for heterologous gene design. Such data from natural genes are very unlikely to provide a basis from which to accurately model the effects of codon choices within the open reading frame upon expression. This is because there is no systematic variation of codon use in natural genes, and because natural genes also include many other differences in sequence elements that have important effects upon expression, such as differences in promoter sequences for initiation of transcription, differences in sequences at and near the initiation codon including ribosome binding sites, internal ribosome entry sites and Kozak consensus sequences, differences in RNA-stabilizing or destabilizing motifs outside the open reading frame. In contrast the method of the present invention can be performed without assumptions regarding the natural codon preferences of the expression host, or the underlying mechanism of such preference. Instead, the expression system is interrogated with systematically varied sets of sequences and measurements of the expression properties of interest to determine the codon biases that result in desired expression properties. This method may be applied to any expression system as well as to identify an optimal bias for high expression in multiple systems if a polynucleotide is to be expressed in different systems.

5.4.1 Constructing Codon Frequency Lookup Tables for Design of Polynucleotides in Codon Variant Sets A plurality of polynucleotide sequences for sequence-expression modeling may be obtained by varying one or more design parameters during the design of each polynucleotide within the plurality of polynucleotide sequences.

In one preferred embodiment, polynucleotide sequences for sequence-expression modeling may be designed using a set of different variant design codon frequency lookup tables. One variant design codon frequency lookup table can be used for designing each polynucleotide sequence in the codon variant set (plurality of polynucleotide sequences), for example by probabilistically selecting codons according to the frequency in the variant design codon frequency lookup table, or by using genetic algorithms or monte carlo algorithms to produce a polynucleotide sequence that conforms to the variant design codon frequency lookup table.

In a preferred embodiment of the invention, selection of the relative synonymous codon frequencies for an amino acid in a variant design codon frequency lookup table can be performed as a function of the codon biases for that amino acid within an initial codon bias matrix. An initial codon bias matrix is a table comprising one or more codon biases for each amino acid. There may be more different codon biases for one amino acid than another. Values for codon bias in an initial codon bias matrix may be drawn from codon bias tables derived from natural gene sequences, or calculated in other ways, for example they may be calculated based upon known biochemical processes such as the rate of recharging (amino acylation) of tRNAs, or they may be calculated based upon the GC content of the codon, or they may be calculated based upon experimentally determined codon preferences for an expression system of interest.

For example, consider using the codon bias values from the genomic sequences of *Saccharomyces cerevisiae* open reading frames and those from highly expressed *E. coli* genes for the initial codon bias matrix. The codon bias for Tyr in the *E. coli* codon bias table is TAC 0.65 and TAT 0.35. The codon bias for Tyr in the *Saccharomyces cerevisiae* codon bias table is TAC 0.44 and TAT 0.56. The function by which a codon bias for Tyr may be calculated for a variant design codon frequency lookup table has many possible forms. In one form, the new bias for Tyr could simply be selected from one of the original biases, in this case either the *E. coli* bias or the S cerevisiae bias. In another form, the new bias for Tyr could be selected probabilistically based on a distribution between the two biases in the initial codon bias matrix. In another form, the new bias for Tyr could use exclusively the codon that is used most on average (in this case TAC) or exclusively the codon which is used least on average (in this case TAT). In another form, one or more additional codon biases for Tyr may be calculated as intermediates between the codon biases from the initial codon bias matrix and the new bias for Tyr selected from one of these. In another form, an additional codon bias for Tyr may be calculated as each codon represented equally; this "flat" codon bias may be used in combination with any of the other forms of the codon bias calculation function. One skilled in the art will readily appreciate that there are many ways to calculate a new codon bias using two or more initial codon biases. Any of these methods may be used to calculate the codon bias for each amino acid to be used in constructing a variant design codon frequency lookup table. Further, the codon bias in a variant design codon frequency lookup table can be selected in the same way for each amino acid, or it may be selected differently for different amino acids.

The aim when designing a plurality of polynucleotides to interrogate a codon space is to obtain codon usages that are distributed in such a way that a large amount of information can subsequently be extracted from sequence-expression relationships. In this respect, the design of codon variant sets has common elements with the design of experimental datasets from a diverse range of other disciplines including agriculture and engineering. Methods to optimize experimental datasets (experimental design or design of experiment: DOE) are described by Sir R. A. Fisher in 1920 (Fisher, The Design of Experiments, MacMillan Publishing Company; 9th edition, 1971). Plackett and Burman developed the idea further with the introduction of screening designs (e.g., Plackett et al., 1946, Biometrika 33: 305-325), and Taguchi subsequently introduced the orthogonal matrix (Taguchi, 1986, *Introduction to Quality Engineering*, Asian Productivity Organization, Distributed by American Supplier Institute Inc., Dearborn, Mich.).

In a preferred embodiment, one or more values for initial codon biases for each amino acid are selected into an initial codon bias matrix. One amino acid may have more discrete values for initial codon biases than another amino acid. Variant design codon frequency lookup tables are then constructed using experimental design techniques to select the codon bias for each amino acid in a way that maximizes the information content of the set of variant design codon frequency lookup tables. These experimental design methods include, but are not limited to, complete factorial design, $2^k$ factorial design, $2^k$ fractional factorial design, central composite, latin squares, greco-latin squares, Plackett-Burmann designs, Taguchi design, and combinations thereof. See, for example, Box et al, 1978, *Statistics for Experimenters*. New York, Wiley, for examples of such techniques that can be used to construct a designed codon variant set from the initial set of variant design codon frequency lookup tables selected to test a maximum number of codon biases in a minimal number of codon variants.

A variation of the above method is to require (i) that for each amino acid, each possible codon bias for that amino acid in the initial codon bias matrix be used an approximately equal number of times in the variant design codon frequency lookup table set, and (ii) that as many different combinations of codon biases for different amino acids (e.g. codon bias pairs) as possible be tested. The solution to such a problem of finding variants with the constraints mentioned here is known as a coverage problem. The coverage problem is NP-hard. Therefore greedy and other forms of approximate solutions are used to solve the NP-hard problems in the present invention. For instance, in some embodiments, the algorithms described in Gandhi et al., 2001, Lecture Notes in Computer Science 2076: 225 are used.

As an example, in some embodiments, the desired set of sequences can be evolved using monte carlo algorithms and/or genetic algorithms to maximize the number of pairs in the plurality of nucleotides. Genetic algorithms are described in Section 7.5.1 of Duda et al., 2001, *Pattern Classification*, Second Edition, John Wiley & Sons, Inc., New York, which is hereby incorporated by reference. Further, similar algorithms can be used to expand the coverage problem to maximize the number of triplets, quadruplets and so on.

An exemplary code for maximizing the codon bias pairs using an evolutionary coverage algorithm is shown below:

Let n be the number of variant design codon frequency lookup tables to be constructed.
  First, create n variant design codon frequency lookup tables, for each amino acid codon bias in each variant design codon frequency lookup table randomly select an initial codon bias for that amino acid drawn from the initial codon bias matrix.
  To obtain a set of variant design codon frequency lookup tables where the codon bias for each amino acid is approximately equally distributed between the possibilities contained in the codon bias matrix, and where the number of codon bias pairs are maximized; first
    for 10000 iterations
    {
      i. Calculate the frequency with which the codon bias for each individual amino acid appearing in the variant design codon frequency lookup tables are drawn from each possible value in the initial codon bias matrix;
      ii. Randomly choose one variant design codon frequency lookup table;
      iii. Randomly choose one individual amino acid;
      iv. Randomly change the codon bias in the selected variant design codon frequency lookup tables for the selected individual amino acid to a different codon bias for this amino acid drawn from the initial codon bias matrix;
      v. Calculate the frequency with which the codon bias for each individual amino acid appearing in the new set of variant design codon frequency lookup tables are drawn from each initial codon frequency lookup table;
      vi. If the frequencies from v) are more even than the frequencies from i), accept the changes from step iv), else, dismiss the changes and retain original values.
    }

```
Output an evolved set of variant design codon frequency lookup tables, then
    for 10000 iterations
    {
                vii.    Count the number of distinct codon bias pairs seen within
                        the set of variant design codon frequency lookup tables;
                viii.   Randomly choose two variant design codon frequency
                        lookup tables;
                ix.     Randomly choose one individual amino acid;
                x.      Randomly swap the codon biases for the one individual
                        amino acid between the two selected variant design codon
                        frequency lookup tables;
                xi.     Count the number of distinct codon bias pairs seen within
                        the new set of variant design codon frequency lookup
                        tables;
                xii.    If the count from xi) is greater than count from vii), accept
                        the changes to the variants from step x), else, dismiss the
                        changes and retain original values.
    }
```

In other embodiments the required distributions may be different, for example the constraint could be that for each amino acid, each possible codon bias for that amino acid in the initial codon bias matrix be used in a distribution other than an approximately equal number of times in the variant design codon frequency lookup table set. In another example, the constraint could be that that as many different combinations of codon biases for only a subset of the different amino acids (e.g. codon bias pairs) as possible be tested. One skilled in the art will appreciate that evolutionary algorithms can be used to design a set of variant design codon frequency lookup tables when these constraints are varied. It is also possible to create codon variant sets where the codon bias for one amino acid is optimized by systematic variation of the codons for that amino acid without varying codon biases for the other amino acids.

5.4.2 Other Methods for Designing Polynucleotides for Codon Variant Sets

Codon variant sets may be constructed to explore other parameters within the open reading frame that may affect expression properties of a polynucleotide. In a preferred embodiment this can be done by a simple modification of the method described for constructing variant design codon frequency lookup tables. Instead of codon frequency lookup tables, tables can be constructed that describe target values for any quantifiable polynucleotide sequence properties, including but not limited to the frequency of any sequence element, (a sequence element can optionally be defined in terms of both a sequence and a reading frame relative to the reading frame of the encoded polypeptide), which includes codons (as described above). Particularly useful sequence elements include a nucleotide triplet in the +3 reading frame, which encodes the "wobble" or third base of one codon and the first two bases of the following codon, and a nucleotide hexamer in the +1 reading frame, which encodes an adjacent pair of codons (a "codon pair"). Other quantifiable sequence properties include GC content, mRNA secondary structures in particular regions of an mRNA produced by the polynucleotide for example covering the start codon, the degree of sequence identity to a reference sequence, the presence of ribosome binding sites, polyadenylation signals, polynucleotide splice signals, the annealing temperature for a subsequence of predetermined length within the polynucleotide for any other sub-sequence within the polynucleotide, repeated sequence elements or homopolymer stretches. Variation in GC %, either of the entire codon or simply at one position (e.g., the more variable 3' terminal nucleotide) is a useful way to vary overall bias and can add diversity in design. These variant design polynucleotide sequence property tables can be used in a similar way to variant design codon frequency lookup tables: a polynucleotide can be designed such that it conforms to the values for quantifiable sequence properties described in one of the polynucleotide sequence property tables.

This may be achieved for example using an evolutionary algorithm that performs the following: (1) select an initial polynucleotide sequence to encode a polypeptide; (2) quantify the one or more polynucleotide sequence properties of interest; (3) identify a possible change to the polynucleotide sequence that does not change the encoded polypeptide; (4) quantify the one or more polynucleotide sequence properties of interest for the polynucleotide sequence after the change in polynucleotide sequence; (5) accept or reject the change based on a function of the difference in values for the one or more polynucleotide properties of interest for the original and the unchanged codon sequences; and (6) repeat this process until a desired value for the one or more polynucleotide sequence properties of interest is obtained. It is also possible to combine designs for polynucleotides in which a specific codon frequency can be combined with one or more other desired polynucleotide sequence properties. One example of how this may be done is:

```
First, select a polynucleotide sequence encoding the target polypeptide,
then for 10000 iterations
{
            i.      calculate the codon bias for each amino acid in the
                    polynucleotide;
            ii.     compare the codon bias for each amino acid in the
                    polynucleotide with the codon bias in the variant design
                    codon frequency lookup table;
            iii.    randomly choose one codon in the polynucleotide;
            iv.     randomly change the selected codon for a different codon
                    encoding the same amino acid;
            v.      calculate the codon bias for each amino acid in the
                    modified polynucleotide;
            vi.     compare the codon bias for each amino acid in the
                    polynucleotide with the codon bias in the variant design
                    codon frequency lookup table;
            vii.    if the match between the variant design codon frequency
                    lookup table and the codon bias in the modified
                    polynucleotide calculated in vii) is better than the match
                    between the variant design codon frequency lookup table
                    and the codon bias in the original polynucleotide
                    calculated in iii), accept the changes from step v), else,
                    dismiss the changes and retain original values.
```

-continued

```
}
Output an evolved sequence, then
for 10000 iterations
{
    viii.  calculate a value for each of the quantifiable
           polynucleotide properties of interest for the
           polynucleotide;
      ix.  compare the values calculated in viii) with the values for
           the properties described in the polynucleotide sequence
           property table;
       x.  randomly choose two codons for the same amino acid
           within the polynucleotide;
      xi.  exchange the two codons;
     xii.  calculate a value for each of the quantifiable
           polynucleotide properties of interest for the modified
           polynucleotide;
    xiii.  compare the values calculated in xii) with the values for
           the properties described in the polynucleotide sequence
           property table;
     xiv.  if the match between the values in the polynucleotide
           sequence property table and those calculated for the
           modified polynucleotide calculated in xii) is better than the
           match between the polynucleotide sequence property table
           and those calculated for the original polynucleotide
           calculated in ix), accept the changes from step x), else,
           dismiss the changes and retain original values.
}
```

Codons may be replaced more generally with any sequence element, for example by using an evolutionary algorithm that performs the following: (1) select an initial polynucleotide sequence to encode a polypeptide; (2) quantify the one or more polynucleotide sequence properties of interest; (3) identify a possible change to the polynucleotide sequence that does not change the encoded polypeptide; (4) quantify the one or more polynucleotide sequence properties of interest for the polynucleotide sequence after the change in polynucleotide sequence; (5) accept or reject the change based on a function of the difference in values for the one or more polynucleotide properties of interest for the original and the unchanged codon sequences; and (6) repeat this process until a desired value for the one or more polynucleotide sequence properties of interest is obtained. It is also possible to combine designs for polynucleotides in which a specific codon frequency can be combined with one or more other desired polynucleotide sequence properties. One example of how this may be done is:

```
First, select a polynucleotide sequence encoding the target polypeptide,
then for 10000 iterations
{
      i.  obtain a sequence element frequency lookup table
          corresponding to an expression system, where the
          frequency lookup table comprises a plurality of sequence
          elements and a plurality of frequency ranges, each
          frequency range in the plurality of frequency ranges is for
          a corresponding sequence element in the plurality of
          sequence elements, each respective frequency range in the
          plurality of frequency ranges specifies a range of
          frequencies that the sequence element corresponding to the
          respective frequency range can occur in a polynucleotide
          that is to be expressed in the expression system, and each
          sequence element in the plurality of sequence elements is
          optionally associated with a frame designation in the
          frequency lookup table
     ii.  calculate the frequency with which each sequence element
          is present in its designated frame (if any) in the
          polynucleotide;
    iii.  compare the frequencies for each sequence element in the
          polynucleotide with the frequencies in the variant design
          sequence element frequency lookup table;
     iv.  randomly choose one codon in the polynucleotide;
      v.  randomly change the selected codon for a different codon
          encoding the same amino acid;
     vi.  calculate the frequency with which each sequence element
          is present in its designated frame (if any) in the modified
          polynucleotide;
    vii.  compare the frequencies for each sequence element in the
          polynucleotide with the frequencies in the variant design
          sequence element frequency lookup table;
   viii.  if the match between the variant design sequence element
          frequency lookup table and the sequence element
          frequencies in the modified polynucleotide calculated in
          vii) is better than the match between the variant design
          sequence element frequency lookup table and the sequence
          element frequencies in the original polynucleotide
          calculated in iii), accept the changes from step v), else,
          dismiss the changes and retain original values.
}
Output an evolved sequence, then optionally
for 10000 iterations
{
     ix.  calculate a value for each of the quantifiable
          polynucleotide properties of interest for the
          polynucleotide;
      x.  compare the values calculated in viii) with the values for
          the properties described in the polynucleotide sequence
          property table;
     xi.  randomly choose two sequence elements from the
          sequence element frequency lookup table that encode the
          same polypeptide features within the polynucleotide;
    xii.  exchange the two sequence elements;
   xiii.  calculate a value for each of the quantifiable
          polynucleotide properties of interest for the modified
          polynucleotide;
    xiv.  compare the values calculated in xii) with the values for
          the properties described in the polynucleotide sequence
          property table;
     xv.  if the match between the values in the polynucleotide
          sequence property table and those calculated for the
          modified polynucleotide calculated in xii) is better than the
          match between the polynucleotide sequence property table
          and those calculated for the original polynucleotide
          calculated in ix), accept the changes from step x), else,
          dismiss the changes and retain original values.
}
```

There is evidence that in some expression systems under some conditions the rate of decoding of some codons can depend upon the sequence of adjacent codons. There are some biases in codon usage dependent on neighboring codons found in the genomes of several organisms. For example there can be a high correlation between the 3' terminal nucleotide of a codon and the first two nucleotides of the next codon. Thus, one quantifiable polynucleotide property is the bias of the triplets defined by these three nucleotides (e.g., the triplets in the −1 frame register).

Decoding rate can depend highly on tRNA availability. As multiple codons are often read by a single tRNA and multiple tRNAs can read a particular codon, in some embodiments of the invention it can be advantageous to cluster codons according to tRNA assignments and create polynucleotide variant sets varied by tRNA usage rather than independently varying codons.

Some genes contain sequence elements that affect expression at the transcription or translation level. Making the genes less similar to the original natural sequence increases the likelihood of eliminating such elements. Varying similarity to the natural sequence also provides an additional means to globally alter codon usage. The natural sequence represents a particular codon frequency bias and increasing dissimilarity will generally alter bias in a way that can differ from other methods. Any gene sequence, not only a naturally occurring sequence, may be used as a reference for such a purpose. For example, one may wish to use a known poorly expressed variant as a reference to vary similarity to.

In some cases it has been shown to be advantageous to eliminate the use of codons in a gene that are very rarely used in the host organism. However, it can also be detrimental to reduce codon usage to only the most frequently used codons in the genome of the host. In order to find an optimal balance between eliminating slow codons maximizing the usage of the available tRNA pool, it is useful to vary the frequency cutoff for codons to be allowed in the gene design.

In some embodiments of the invention it may be useful to further modify the codon bias in the variant set:

(i) Codon bias optimization. Results from a codon variant set (plurality of polynucleotides) that has been synthesized and tested for one or more expression property can be analyzed for correlation of actual codon bias, by amino acid, to predict new bias directions that might better correlate with expression, for testing in a subsequent codon variant set.

(ii) Focused codon usage tables. It may be advantageous to synthesize variant sets where only particular codons or codon sets for particular amino acids are varied.

(iii) Specific tRNA usage. Multiple codons may be read by a single tRNA and multiple tRNAs may read the same codon in some cases. As tRNA availability may be a critical factor in determining expression level, varying genes based on tRNA usage rather than codon usage can sometimes be informative and yield predictive models that complement codon usage variable sets.

(iv) 5' codon usage. In addition to overall codon bias, the first 100 bases, or the first 80 bases or the first 60 bases or the first 40 bases of the open reading frame of a polynucleotide may contain variables that correlate with expression properties of the polynucleotide.

(v) Codon diversity. A measure of the overall diversity of codons used for each amino acid throughout a gene may be relevant to expression.

By measuring one or more expression property of polynucleotides in a codon variant set it is possible to identify the individual polynucleotide with the best expression properties in that set. Such design of a codon variant set and selection of the best expressing variant is an aspect of the invention. This may be sufficient for a desired application.

5.5 ANALYSIS OF EXPRESSION IN CODON VARIANT SETS

It may be desirable to analyze expression data and correlate it with the codon frequencies of the designed polynucleotides. Such analyses can be used to identify frequencies or ranges of frequencies for codons within a polynucleotide that result in superior expression properties. The results of this analysis can be formulated as a frequency lookup table to be used in the design of polynucleotide sequences, or directly as a new polynucleotide sequence. The analysis of expression data from codon variant sets to provide design rules for new polynucleotides is an aspect of the invention.

5.5.1 Models from Multivariate Regression

In one embodiment, expression data for each of the polynucleotides in a codon variant set is analyzed by determining the correlation of sequence variables with at least one property that affects an expression property of polynucleotides in the codon variant set using multivariate regression. The independent variables input for regression may be, for example, individual codon frequencies used in the plurality of polynucleotides in the codon variant set, estimates of tRNA usage frequencies used, frequencies or strengths of mRNA structures, occurrence of defined sequence motifs, or summary sequence statistics, such as GC percentage, Codon Adaptiveness Index, or total length.

Several methods exist for regression of multivariate data, where predictive relationships between some or all of the independent variables and expression level are determined. Examples of such methods are Partial Least Squares (PLS) and Principal Components Regression (PCR) (Wold et al., 1993, "DNA and peptide sequences and chemical processes multivariately modeled by principal component analysis and partial least-squares projections to latent structures," Analytica Chimica Acta 277, 239-253). PLS algorithms, for example, seek to maximize the correlation of the X-data (e.g., codon frequencies) and expression while simultaneously maximizing the X-data variance captured in the model. In doing so, the algorithm determines new orthogonal variables, called latent variables, which are linear combinations of the original variables that best capture the X-data and explain Y variation.

More generally, assessment of the contributions of relative or absolute codon frequencies to one or more expression property can be performed by deriving a sequence-expression relationship. Such a relationship can be expressed very generally, for example as shown in Equation A $$Y = f(x_{AAA}, x_{AAC}, \ldots x_{NNN}) \qquad (\text{Eq A})$$

where,

Y is a quantitative measure of an expression property (e.g., level of protein expressed, level of soluble protein expressed or level of active protein expressed), $x_{NNN}$ is the relative or absolute frequency of codon NNN, and f( ) is a mathematical function that can take any of several different forms.

In a simple embodiment of the invention, the function f can be a linear combination of $x_i$:

$$Y = w_{AAA} x_{AAA} + w_{AAC} x_{AAC} + \ldots w_{NNN} x_{NNN} \qquad (\text{Eq. b})$$

where, $w_{NNN}$ is a weight (or coefficient of $x_{NNN}$).

In some embodiments, to derive a sequence-expression relationship, a set of descriptors ($x_{NNN}$) that can describe the frequencies of some or all of the codons within the codon variant set is identified. Values of Y for each member of the codon variant set are measured. Values for each weight ($w_{NNN}$) are then calculated such that the differences between values predicted for each value of Y by Equation A and those observed experimentally are minimized for the codon variant set, or for a selected subset of such codon variants.

The minimization step above can also use weights for different expression property predictions and, in general, can use a loss function. In one embodiment this loss function can be squared error loss, where weights that minimize the sum of squares of the differences between predicted and measured values for the dataset are computed.

In some embodiments statistical regression methods are used to identify relationships between dependent ($x_{NNN}$) and independent (Y) variables. Such techniques include, but are not limited to, linear regression, non-linear regression, logistic regression, multivariate data analysis, and partial least squares regression. See, for example, Hastie, *The Elements of Statistical Learning*, 2001, Springer, New York; Smith, *Statistical Reasoning*, 1985, Allyn and Bacon, Boston. In one embodiment, regression techniques like the PLS (Partial Least Square) can be used to solve for the weights ($w_{NNN}$) in the equation X. Partial Least Squares (PLS) is a tool for modeling linear relationships between descriptors. The method is used to compress the data matrix composed of descriptors(variables) of variant sequences being modeled into a set of latent variables called factors. The number of latent variables is much smaller than the number of variables (descriptors) in the input sequence data. For example, if the number of input variables is 100, the number of latent variables can be less than 10. In some embodiments, the factors are determined using the nonlinear iterative partial least squares algorithm. The orthogonal factor scores are used to fit a set of activities to the dependent variables. Even when the predictors are highly collinear or linearly dependent, the method finds a good model. Alternative PLS algorithms like the SIMPLS can also be used for regression. In such methods, the contribution to the activities from every variable can be deconvoluted to study the effect of sequence on the function of the protein.

In some embodiments, modeling techniques are used to derive sequence-expression relationships. Such modeling techniques include linear and non-linear approaches. Linear and non-linear approaches are differentiated from each other based on the algebraic relationships used between variables and responses in such approaches. In the system being modeled, the input data (e.g., variables that serve as descriptors of the biopolymer sequence), in turn, can be linearly related to the variables provided or non-linear combinations of the variables. It is therefore possible to perform different combinations of models and data-types: linear input variables can be incorporated into a linear model, non-linear input variables can be incorporated into a linear model and non-linear variables can be incorporated into a non-linear models.

Many functional forms of f( ) (Eqn. A) can be used and the functional form can be combined using weights defined for analysis. For example, Function f( ) can assume a non-linear form. An example of non-linear functional form is:

$$Y = w_{12} * x_1 * x_2 + w_{13} * x_1 * x_3 + \ldots w_{nn} * x_n * x_n$$

Non-linear functions can also be derived using modeling techniques such as machine learning methods. For example, the codon($x_{NNN}$)-expression(Y) data to predict the activities of any sequence given the descriptors for a sequence can be determined using neural networks, Bayesian models, generalized additive models, support vector machines and classification using regression trees.

In some embodiments, supervised learning techniques are used to identify relationships between relative or absolute codon frequencies in the designed set and measured expression properties. Such supervised learning techniques include, but are not limited to, Bayesian modeling, nonparametric techniques (e.g., Parzen windows, $k_n$-Nearest-Neighbor algorithms, and fuzzy classification), neural networks (e.g., hopfield network, multilayer neural networks and support vector machines), and machine learning algorithms (e.g., algorithm-independent machine learning). See, for example, Duda et al., *Pattern Classification*, $2^{nd}$ edition, 2001, John Wiley & Sons, Inc. New York; and Pearl, *Probabilistic Reasoning in Intelligent Systems: Networks of Plausible Inference*, Revised Second Printing, 1988, Morgan Kaufmann, San Francisco. For example, the codon ($x_{NNN}$)-expression (Y) data can be used to predict the expression property of any sequence given the codon descriptors for a sequence using a neural network. The input for the network is the descriptors and the output is the predicted value of Y. The weights and the activation function can be trained using supervised decision based learning rules. The learning is performed on a subset of variants called the training set and performance of the network is evaluated on a test set.

In some embodiments, unsupervised learning techniques are used to identify relationships between relative or absolute codon frequencies in the designed set and measured expression properties. Such unsupervised learning techniques include, but are not limited to stochastic searches (e.g., simulated annealing, Boltzmann learning, evolutionary methods, principal component analysis, and clustering methods). See, for example, Duda et al., *Pattern Classification*, $2^{nd}$ edition, 2001, John Wiley & Sons, Inc. New York. For example, the weights in equation B can be adjusted by using monte carlo and genetic algorithms. The optimization of weights for non-linear functions can be complicated and no simple analytical method can provide a good solution in closed form. Genetic algorithms have been successfully used in search spaces of such magnitude. Genetic algorithms and genetic programming techniques can also be used to optimize the function form to best fit the data. For instance, many recombinations of functional forms applied on descriptors of the sequence variants can be applied.

In some embodiments, boosting techniques are used to construct and/or improve models developed using any of the other techniques described herein. A model of the sequence-expression relationship can be described as a functional form whose parameters have been trained for the input data (Y and $x_{NNN}$). Many algorithms/techniques to build models have been described. Algorithms applied on a specific dataset can be weak in that the predictions can be less accurate or "weak" (yielding poor models). Models can be improved using boosting techniques. See, for example, Hastie et al., *The Elements of Statistical Learning*, 2001, Springer, New York. The purpose of boosting is to combine the outputs of many "weak" predictors into a powerful "committee." In one embodiment of the invention, boosting is applied using the AdaBoost algorithm. Here, the prediction algorithm is sequentially applied to repeatedly modified versions of the data thereby producing a sequence of models. The predictions from all of these models are combined through a weighted majority vote to produce the final prediction. The data modification at each step consists of applying weights ($W^b_i$) to each of the i training observations. Initially weights are set to 1/N, where N is the number of training observation (sequence-activity data). The weights are modified individually in each successive iteration. Training observations that were predicted poorly by a particular model have their weights increased and training observations that were predicted more accurately have their weights decreased. This forces each successive model to concentrate on those training observations that are issued by the previous model. The step of combining the models to produce a "committee" assigns a weight to each model based on the overall prediction error of that model.

The various modeling techniques and algorithms described herein can be adapted to derive relationships between one or more expression properties or functions of a nucleic acid sequence of polynucleotide and therefore to make multiple predictions from the same model. Modeling techniques that have been adapted to derive sequence-expression relationships for polynucleotides are within the scope of the present invention. Some of these methods derive linear relationships (for example partial least squares projection to latent structures) and others derive non-linear relationships (for example neural networks). Algorithms that are specialized for mining associations in the data are also useful for designing sequences to be used in the next iteration of sequence space exploration. These modeling techniques can robustly deal with experimental noise in the activity measured for each variant. Often experiments are performed in replicates and for each variant there will be multiple measurement of the same activity. These multiple measurements (replicate values) can be averaged and treated as a single number for every variant while modeling the sequence-expression relationship. The average can be a simple mean or another form of an average such as a geometric or a harmonic mean. In the case of multiple measurements, outliers can be eliminated. In addition, the error estimation for a model derived using any algorithm disclosed herein can incorporate the multiple measurements through calculating the standard deviation of the measurement and comparing the predicted activity from the model with the average and estimate the confidence interval within which the prediction lies. Weights for observations to be used in models can also be derived from the accuracy of measurement, for example, through estimating standard deviation and confidence intervals. This procedure can put less emphasis on variants whose measurements are not accurate. Alternatively, these replicate values can be treated independently. This will result in duplicating the sequences in the dataset. For example, if sequence variant, represented by descriptor values $\{x_j\}^{i1}$, has been measured in triplicates ($Y_{i1}$, $Y_{i2}$, $Y_{i3}$), the training set for modeling will include descriptor value $\{x_j\}^{i2}$ with activity $Y_{i2}$ and $\{x_j\}^{i3}$ with activity $Y_{i3}$ in addition to $\{x_j\}^{i1}$ with activity $Y_{i1}$, where $\{x_j\}^{i1}=\{x_j\}^{i2}=\{x_j\}^{i3}$.

A representative modeling routine in accordance with one embodiment of the invention comprises the following steps.

Step 302. Relevant descriptors of the sequence are identified. These descriptors can convey absolute or relative frequencies of sequence elements including codons. They can also contain information about the location of the sequence element within the polynucleotide, or the distribution of the sequence element throughout the polynucleotide.

In some embodiments, it is advantageous to identify absolute or relative codon frequencies based on factors including, but not limited to absolute and relative positions within the polynucleotide. For example, a weight of a can be assigned for variables in domain A of the polynucleotide and a weight of b can be assigned for variables in domain B of the polynucleotide. This weighting can also incorporate constraints and other functional considerations that may or may not be measured in experiments, but which can be fully or partially be predicted using computational techniques.

Step 304. In step 304 the parameters for the functional form of the sequence-activity relationship are optimized to obtain a model by minimizing the difference between the predicted values and real (measured) values of the expression property of the polynucleotide. Such optimization adjusts the individual weights for each descriptor identified in preceding steps using a refinement algorithm such as least squares regression techniques. Other methods that use alternative loss functions for minimization can be used to analyze any particular dataset. For example, in some polynucleotide sequence-expression data sets, the expression properties may not be distributed evenly throughout the measured range. This will skew the model towards data points in the activity space that are clustered. This can be disadvantageous because datasets often contain more data for polynucleotide variants with low levels of activity, so the model or map will be biased towards accuracy for these polynucleotides which are of lower interest. This skewed distribution can be compensated for by modeling using a probability factor or a cost function based on expert knowledge. This function can be modeled for the activity value or can be used to assign weights to data points based on their activity. As an example, for a set of activities in the range of 0 to 10, transforming the data with a sigmoidal function centered at five will give more weight to sequences with activity above five. Such a function can optionally also be altered with subsequent iterations, thereby focusing the modeling on the part of the dataset with the most desired functional characteristics. This approach can also be coupled with exploring techniques like a Tabu search, where undesired space is explored with lower probabilities.

In some embodiments, algorithms that optimizes the sequence-expression model for the dataset by randomly starting with a solution (e.g., randomly assigning weights $w_{NNN}$) and using methods like hill-descent and/or monte-carlo and/or genetic algorithm approaches to identify optimal solutions.

In embodiments directed to codon optimization, robustness of the models used is a significant criterion. Thus, obtaining several sub-optimal solutions from various initial conditions and looking at all the models for common features can be a desirable methodology for ensuring the robustness of the solution. Another way to obtain robust solutions is to create bootstrap data sets based on the input data, than estimate a p-value or confidence on the various coefficients of the model. In addition boosting techniques like AdaBoost can be used to obtain a "committee" based solution.

Step 306. Many mathematical modeling techniques for deriving a sequence-expression correlation are evaluated. Preferred mathematical modeling techniques used to identify and capture the sequence-activity correlation handle (i) very large numbers of variables (e.g 20 or more) and correlations between variables, (ii) linear and non-linear interactions between variables, and (iii) are able to extract the variables responsible for a given functional perturbation for subsequent testing of the mathematical model (e.g., models should be easily de-convoluted to assign the effect of variables describing the amino acids substitution with activities).

Step 308. In step 308 the coefficients (parameters) of the model(s) are deconvoluted to see which codon frequencies (variables/descriptors of the variants) influence the expression properties of the polynucleotide. It can be important to identify which descriptor(s) of the polynucleotide are important for the activity of interest. Some of the techniques, such as partial least squares regression (SIMPLS) that uses projection to latent structures (compression of data matrix into orthogonal factors) may be good at directly addressing this point because contributions of variables to any particular latent factors can be directly calculated. See, for example, Bucht et al., 1999, Biochim Biophys Acta. 1431:471-82; and Norinder et al., 1997, J Pept Res 49: 155-62. Other methods such as neural networks can learn from the data very well and make predictions about the activity of entire polynucleotides, but it may be difficult to extract information, such as individual contributing features of the polynucleotide from the model. Modeling techniques/methods that directly correlate the codon frequency variations to the expression property are preferred because they can be used to derive the sequence-expression map (relationship) to construct new polynucleotides or codon bias tables not in dataset that have preferentially higher activities. These methods can be adapted to provide a direct answer and output in desired forms.

Step 310. In step 310 the models developed using various algorithms and methods in the previous step can be evaluated by cross validation methods. For example, by randomly leaving data out to build a model and making predictions of data not incorporated into the model is a standard technique for cross validation. In some instances of polynucleotide expression engineering, data may be generated over a period of months. The data can be added incrementally to the modeling procedure as and when such data becomes available. This can allow for validation of the model with partial or additional datasets, as well as predictions for the properties of biopolymer sequences for which activities are still not available. This information may then be used to validate the model.

In one embodiment of the present invention, average values and standard deviations for weight functions can be obtained by omitting a part of the available data. Either individual sequences and their associated expression activities or individual codons can be left out. A sequence-expression relationship can then be constructed from this partial data. This process can be repeated many times, each time the data to leave out is selected randomly. Finally an average and range of values for each weight function is calculated. The weight functions can then also be ranked in order of their importance to activity. The range of values for each weight can provide a measure of the confidence with which the weight is assigned. It can also provide a measure of the importance of the variable in determining the expression property. For example in some instances, the larger the standard deviation for a variable weight, the larger the range of values for that variable that are associated with desirable expression properties.

To assess the probability that a codon frequency is associated with an activity by random chance, the same weight function calculations can be performed when the sequences and activities are randomly associated. In this case there should be no relationship between codon frequencies and expression property, so weight functions arise only by chance. A measure of the confidence for the weight function can then be calculated. It is related to the number of standard deviations by which the value calculated when sequences and activities are correctly associated exceeds the value calculated when they are randomly associated. The above methods on model assessment, model inference and averaging are discussed in detail by Hastie et al., 2001, Springer Verlag, series in statistics.

Step 312. In step 312 new polynucleotide sequences or codon biases that are predicted to possess one or more desired property are derived. Alternatively it can be desirable to rank order the input variables for detailed sequence-expression correlation measures. The model can be used to propose codon biases that have high probabilities of being improved. Polynucleotides designed to conform to such codon biases can then optionally be synthesized and tested. In one embodiment, this can be achieved if the effects of various sequence features of the polynucleotides on their functions are known based on the modeling. Alternatively, for methods like neural networks, $10^3$ or $10^6$ or $10^9$ or $10^{12}$ or $10^{15}$ or $10^{18}$ or as many as $10^{80}$ sequences can be evaluated in silico. Then those predicted by the model to possess one or more desired properties are selected.

Step 314. The statistical quality of the model fit to the input data is evaluated in step 314. Validation of sequence-expression correlation can be internal, using cross-validation of the data, or preferably external, by forecasting the functional perturbation of a set of new sequences derived from the model. Sequences with predicted values of their functional perturbations are then physically made and tested in the same experimental system used to quantify the training set. If the sequence-expression relationship of the dataset is satisfactorily quantified using internal and external validation, the model can be applied to a) predict the functional value of other related sequences not present in the training set, and b) design new sequences within the described space that are likely to have a function value that is outside or within the range of function given by the training set.

The initial set of data can be small, so models built from it can be inaccurate. Improving the modeled relationship further depends upon obtaining better values for weights whose confidence scores are low. To obtain this data, additional variants designed will provide additional data useful in establishing more precise sequence-expression relationships.

The output from each method for modeling a sequence-activity relationship can be one or more of: (i) a regression coefficient, weight or other value describing the relative or absolute contribution of each codon frequency or combination of codon frequencies to one or more expression activity of the polynucleotide, (ii) a standard deviation, variance or other measure of the confidence with which the value describing the contribution of the codon frequency or combination of codon frequencies to one or more expression activity of the polynucleotide can be assigned, (iii) a rank order of preferred codons, (iv) the additive & non-additive components of each codon frequency or combination of codon frequencies, (v) a mathematical model that can be used for analysis and prediction of the functions of in silico generated sequences. Such output can be used to generate a frequency lookup table. For example, codons that are assigned more significant weights in the modeling described above can be assigned frequency ranges in the frequency lookup table that contain higher frequencies than codons that are assigned less significant weights.

5.5.2 Codon Frequency Data

One preferred way to define independent variables for sequence variants is as individual codon frequencies. As one example, the mean-centered frequency occurrence of each of the 61 sense codons for a set of N genes is input as the independent variable matrix (N×61 X-data matrix) and the N absolute or relative expression levels are input as the dependent variables. PLS modeling is used to define useful latent variables from the codon frequencies for prediction of expression. The number of latent variables to include in the regression is chosen such that a maximum capture of the codon and expression data is achieved without over fitting. This is achieved using cross-validation methods to assess the ability of models based on subsets of the data to predict expression of the excluded sets. Latent variables are included only if they significantly reduce the cross-validation error. The regression returns several statistics that express the relationship of the codon frequencies to the latent variables (e.g., the variable loadings on the latent variables) and to the expression levels (e.g., the regression vectors for the Y data). The regression vector for Y is a matrix of values for each of the codon frequencies that expresses the relative contribution of each codon to the predicted expression level, according to $$Y_M = R(X_M)$$

where R is the regression vector, $Y_M$ is the predicted mean centered expression level, and $X_M$ is the N×1 mean centered codon frequency matrix for a given gene. Thus the regression vector matrix, R, may be used to predict expression of any given gene based on the codons frequencies used for that gene.

5.5.3 Variable Selection Methods

Additional analyses of the data may be used to further refine models and to indicate the relative significance of the codon frequencies to the expression model. One useful statistic is the Variable Importance in the Projection (VIP) which is a measure of the dependence of the model fit on inclusion of a variable. VIP values greater than one are generally considered significant. Analysis of the VIP can be used to pick which codons are most likely important for influencing expression. Another method of variable selection involves the use of a Genetic Algorithm (GA). In a typical GA run for codon frequency analysis, 100 random subsets, or "samples", of 15-25 of the 61 sense codons are generated and evaluated for their ability to explain the data in PLS modeling. The error of the PLS fit of the data in cross validation (RMSECV) is used to distinguish the subsets. Those that yield lower than median RMSECV are retained. The codon sets used by random pairs of these selected samples are then recombined at two random crossover points to create new progeny samples. The resulting samples, the original selected and their progeny, are then analyzed for fit as before and the best half are used to create the next sample generation. At each generation, mutation (substituting one codon variable in a sample for another) is allowed to prevent the model from prematurely eliminating or fixing under- or overrepresented variables, respectively. The entire process is repeated until there is convergence in makeup and performance of the selected population. The final samples will have codon sets that better fit the expression data.

For variable selection it is useful to analyze the frequency of inclusion of codons used in the sample population as the GA iterates. Codons that are most enriched by the GA are taken as most likely significant for expression. One may also use the best sample codon sets generated by the GA as refined, potentially more precise, sets for modeling expression. The codons whose frequencies have most effect on expression can also be determined using other combinations of analytical method such as dimension-compressing techniques including partial least squares regression and principal component analysis, with stochastic search methods including genetic algorithms, monte carlo algorithms or simulated annealing algorithms.

5.5.4 Additional Methods for Determining an Expression Property of Polynucleotides in an Expression System Another aspect provides a method of determining at least one property that affects an expression property of polynucleotides in an expression system. The method comprises constructing a first plurality of polynucleotides. The first plurality of polynucleotides comprises five or more polynucleotides, ten or more polynucleotides, twenty or more polynucleotides, thirty or more polynucleotides, or more than 50 polynucleotides. Each polynucleotide in the first plurality of polynucleotides encodes a predetermined polypeptide sequence. A frequency with which a first sequence element is used in a first polynucleotide in the first plurality of polynucleotides is different than a frequency with which the first sequence element is used in a second polynucleotide in the first plurality of polynucleotides. Each respective polynucleotide in the first plurality of polynucleotides is expressed individually in the expression system. An expression property value of each respective polynucleotide in the first plurality of polynucleotides in the expression system is measured, thereby constructing a dataset. The dataset comprises, for each respective polynucleotide in the first plurality of polynucleotides, a representation of sequence element occurrence in the respective polynucleotide and the measured expression property value of the respective polynucleotide.

A sequence element is a defined sequence of nucleotides and may also include a reading frame designation relative to the reading frame of a polypeptide encoded by a polynucleotide. Sequence elements include but are not limited to codons, nucleotide triplets in the +3 reading frame (encoding the "wobble" or third base of one codon and the first two bases of the following codon) and nucleotide hexamers in the +1 reading frame (encoding an adjacent pair of codons or "codon pair"). Other quantifiable sequence properties include GC content, mRNA secondary structures in particular regions of an mRNA produced by the polynucleotide for example covering the start codon, the degree of sequence identity to a reference sequence, the presence of ribosome binding sites, polyadenylation signals, polynucleotide splice signals, the annealing temperature for a sub-sequence of predetermined length within the polynucleotide for any other sub-sequence within the polynucleotide, repeated sequence elements or homopolymer stretches. Variation in GC %, either of the entire codon or simply at one position (e.g., the more variable 3' terminal nucleotide) is a useful way to vary overall bias and can add diversity in design. These properties can be tabulated in variant design polynucleotide sequence property lookup tables that can be used in a similar way to sequence element frequency lookup tables: a polynucleotide can be designed such that it conforms to the values for quantifiable sequence properties described in one of the polynucleotide sequence property tables.

In the method a final model is computed. The final model comprises (i) a plurality of variables, each variable in the plurality of variables describing a frequency of occurrence of one or more sequence elements in the first plurality of polynucleotides, or another quantifiable sequence property and (ii) a plurality of weights, each weight in the plurality of weights corresponding to one or more variables in the plurality of variables. In some embodiments, the plurality of variables is three or more variables, four or more variables, five or more variables, six or more variables, between five and twenty-five variables, between four and sixty variables, or less than forty variables. In some embodiments, the plurality of weights is three or more weights, four or more weights, five or more weights, six or more weights, between five and twenty-five weights, between four and sixty weights, or less than forty weights. In some embodiments, there is one-to-one correspondence between each variable in the plurality of variables and each weight in the plurality of weights. In some embodiments the final model describes a variation in the measured expression property values of the first plurality of polynucleotides from the measuring as a function of the plurality of variables and their corresponding weights.

From the final model at least one property that affects an expression property of polynucleotides in the expression system is determined. The at least one property is an effect that the frequency of occurrence of one or more sequence elements has on the expression property of polynucleotides in the expression system.

In some embodiments, computation of the final model comprises searching a multivariate space using a global optimization algorithm thereby computing the final model. This multivariate space comprises the plurality of variables. In other words, this multivariate space comprises all possible combinations of all possible values for each variable in the plurality of variables. For instance, consider the hypothetical case where the plurality of variables consists of variables A and B, and that each variable can have the value 1 or 2. In this case, the multivariate space that comprises the plurality of variables is {(A1, B1), (A1, B2), (A2, B1}, and (A2, B2)), wherein (A1, B1) means that variable A has value 1 and variable B has value 1, and so forth. In fact, there are typically many variables (e.g., between five and fifty variables) in the plurality of variables and each variable can adopt any of several different values. Further, each variable is weighted by one or more weights. Thus, the multivariate space is very large. Because of the large size of the multivariate space, a global optimization algorithm is used in some embodiments to help find the final model in the multivariate space. In many embodiments, there is no guarantee that the final model is the absolute best model for the dataset. It is simply the best model found by the global optimization algorithm given the input dataset.

The global optimization algorithm assigns a respective score to each respective test model in a plurality of test models in order to find the final model. Each of these test models is some combination of the plurality of variables and the plurality of weights. For example, if the plurality of variables consists of fifty variables, a given test model may consist of fifteen variables and fifteen corresponding weights, where each respective weight is for a corresponding variable. Thus, there is no requirement that each test model include each variable in the plurality of variables. In fact, in the case where variables represent codon frequency, it is desirable to limit the number of variables so that the test model imposes the fewest possible restrictions on codon choice.

Models that use fewer variables to explain the variance in measured expression properties of the plurality of polynucleotides are preferred because they impose less restrictions on codon choice relative to models that include more variables representing codon choice. For example, consider a first test model that includes forty variables, where each of the variables represents a different codon in the set of naturally occurring codons, and explains seventy percent of the variation in the measured expression property of the plurality of polynucleotides and a second test model that includes twenty variables, where each of the variables represents a different codon in the set of naturally occurring codons, and explains sixty-nine percent of the variation in the measured expression property of the plurality of polynucleotides. In this case, the second test model is preferred to the first test model because the second test model imposes restrictions on only twenty different codons whereas the first model imposes restrictions on forty different codons. Thus, if the first model were used to design a polynucleotide sequence, there would be limitations on the frequency with which forty different codons could be used in the polynucleotide. This would reduce the number of possible locations where other sequence elements, such as restrictions sites, could be located in the designed polynucleotide sequence.

The global optimization algorithm assigns a respective score to each respective test model in a plurality of test models in order to find the final model. Each respective score is a quantification of an agreement between (i) expression property values calculated for each respective polynucleotide in the first plurality of polynucleotides by a test model in the plurality of test models and (ii) expression property values measured for each respective polynucleotide in the first plurality of polynucleotides by the measuring described above. In some embodiments, this agreement is a correlation or some other similarity metric. In some embodiments, each test model in the plurality of test models comprises a number of variables in the plurality of variables and a corresponding number of weights in the plurality of weights.

In some embodiments, the plurality of test models is ten or more models, one hundred or more models, one thousand or more models, ten thousand or more models, or one hundred thousand or more models.

In some embodiments, the one or more sequence elements are each codons that are in the same reading frame with respect to the predetermined polypeptide sequence encoded by a polynucleotide in the plurality of polynucleotides. In some embodiments, a sequence element in the one or more sequence elements is a codon pair that is in the same reading frame with respect to the predetermined polypeptide sequence encoded by a polynucleotide in the first plurality of polynucleotides. In some embodiments, a sequence element in the one or more sequence elements is a nucleotide triplet in the +3 reading frame (encoding the "wobble" or third base of one codon and the first two bases of the following codon).

In some embodiments, the computation of the final model further comprises computing a confidence of each respective test model in the plurality of test models and using the respective score for a respective test model in the plurality of test models and the confidence for the respective test model to determine whether to accept or reject the respective test model as the final model.

In some embodiments, the global optimization algorithm is a heuristic search comprising a plurality of steps where, at each step in the plurality of steps, the global optimization algorithm comprises (i) determining a respective score for each respective test model in a subset of the plurality of test models, (ii) enriching the plurality of test models by removing a portion of the subset of the plurality of test models from the plurality of test models based on respective scores assigned to the test models in the subset of test models, and (iii) enriching the plurality of test models by adding a new subset of test models to the plurality of test models, where each test model in the new subset of test models is derived from values for weights in one or more test models already in the plurality of test models. An example of how such an embodiment can be carried out is a genetic algorithm. First, in step (i) a respective score for each respective test model in a subset of the plurality of test models is computed. For example, one thousand models are computed. Each respective model in the one thousand test models is scored for an agreement between (i) expression properties calculated for each respective polynucleotide in the first plurality of polynucleotides by the test model and (ii) expression properties measured for each respective polynucleotide in the first plurality of polynucleotides for which measurement data is available. Next, in (ii) some of the test modes are removed from the plurality (from the set of 1000 test models in this example) of test models. Next, in (iii) the plurality of test models is enriched by adding more test models. The test models added in (iii) are derived from the test models that were not thrown out in (ii). A test model can be derived from other models by taking some of the variables and weights from the other models to form a new combination in the manner known in genetic algorithms. In this way, the global optimization algorithm can efficiently converge on a suitable final model.

In some embodiments, the global optimization algorithm refines a test model in the plurality of test models, before assigning a score to the test model, by principal component analysis in which the variables in the test model are reduced to two or more latent variables that account for all or a portion of a variation in the measured expression property values of the first plurality of polynucleotides. Principal component analysis is described in Hastie, 2003, *The Elements of Statistical Learning*, Springer, New York, pp. 485-493 which is hereby incorporated by reference herein for such purpose. In some embodiments, the global optimization algorithm is a heuristic search. Examples of heuristic searches include, but are not limited to, an evolutionary algorithm, a swarm-based optimization algorithm, a memetic algorithm, or a differential evolution algorithm.

In some embodiments, each of the one or more sequence elements in the final model is defined by a sequence of nucleotides and a reading frame relative to the predetermined polypeptide sequence encoded by a polynucleotide in the plurality of polynucleotides.

In some embodiments, the global optimization algorithm is a stochastic search. Examples of stochastic searches include, but are not limited to, a simulated annealing algorithm, a directed monte-carlo sampling algorithm, a stochastic tunneling algorithm, a parallel tempering algorithm, a monte-carlo with minimization algorithm or a continuation method. See for example, Horst et al., 2000, *Introduction to Global Optimization*, Second Edition, Kluwer Academic Publishers; Neumaier, 2004, Complete Search in Continuous Global Optimization and Constraint Satisfaction, pp. 271-369 in: *Acta Numerica* 2004 (A. Iserles, ed.), Cambridge University Press; Mongeau et al., 2000, Optimization Methods & Software 13(3), pp. 203-226; Kirkpatrick et al., 1983, Science 220:671-680, Hamacher, 2006, Europhys. Lett. 74(6):944, 2006; Hamacher and Wenzel, 1999, Landscape. Phys. Rev. E, 59(1):938-941; Wenzel and Hamacher, 1999, Phys. Rev. Lett., 82(15):3003-3007; Hansmann, 1997, Chem. Phys. Lett., 281:140; Zhijun, November 1996, "The effective energy transformation scheme as a special continuation approach to global optimization with application to molecular conformation," Technical Report, Argonne National Lab., IL (United States), November 1996, each of which is hereby incorporated by reference herein in its entirety.

In some embodiments, the expression property value of a respective polynucleotide in the first plurality of polynucleotides in the expression system is (i) a total amount of protein encoded by the respective polynucleotide that is expressed in the expression system in a defined time, (ii) a total amount of active protein encoded by the respective polynucleotide that is expressed in the expression system in a defined time, or (iii) a total amount of soluble protein encoded by the respective polynucleotide that is expressed in the expression system in a defined time.

In some embodiments, the relative frequency of each respective synonymous codon in a plurality of synonymous codons for each of two or more, three or more, four or more, five or more, six or more, seven or more, eight or more, nine or more, or ten or more amino acids encoded by a reading frame of two or more, three or more, four or more, five or more, six or more, seven or more, eight or more, nine or more, ten or more, twenty or more or one hundred or more polynucleotides in the plurality of polynucleotides is varied in the two or more, three or more, four or more, five or more, six or more, seven or more, eight or more, nine or more, ten or more, twenty or more or one hundred or more polynucleotides.

In some embodiments, the constructing comprises encoding a first polynucleotide in the first plurality of polynucleotides using a first frequency lookup table, where the first frequency lookup table specifies a first target frequency range for the use of a first sequence element in a polynucleotide and where a first frequency that the first sequence element is used in the first polynucleotide is within the first target frequency range Further, in such embodiments, the constructing comprises encoding a second polynucleotide in the first plurality of polynucleotides using a second frequency lookup table, where the second frequency lookup table specifies a second target frequency range for the use of the first sequence element in a polynucleotide and where a second frequency that the first codon is used in the second polynucleotide is within the second target frequency range. Here, the first frequency range is different than the second frequency range.

In some embodiments, each test model in a first subset of test models in the plurality of test models each consist of a first number of variables in the plurality of variables, each test model in a second subset of test models in the plurality of test models each consist of a second number of variables in the plurality of variables and the first number is different than the second number.

In some embodiments, the plurality of variables comprises a variable for each of two or more, three or more, four or more, five or more, six or more, seven or more, eight or more, nine or more, or ten or more naturally occurring codons. In some embodiments, each polynucleotide in the first plurality of polynucleotides encodes the same amino acid sequence.

In some embodiments, the first plurality of polynucleotides comprises a plurality of subsets of polynucleotides and each respective subset of polynucleotides in the plurality of subsets polynucleotides encodes a different amino acid sequence, and each polynucleotide in a subset of polynucleotides in the plurality of polynucleotides encodes the same amino acid sequence.

In some embodiments, the method further comprises constructing a second plurality of polynucleotides, where a frequency that a sequence element is used in the second plurality of polynucleotides is determined by the at least one property from the determining.

In some embodiments, the method further comprises constructing a frequency lookup table for the expression system from the final model, where the frequency lookup table provides a sequence element frequency range for each of two or more sequence elements, three or more sequence elements, four or more sequence elements, five or more sequence elements, six or more sequence elements, or seven or more sequence elements.

5.5.5 Use of Principal Component Analysis for Determining an Expression Property of Polynucleotides in an Expression System In some embodiments, principal component analysis is used to determine a property that affects an expression property of polynucleotides in an expression system. Such an approach is advantageous because it prevents overfitting of the measured expression data using too many variables.

One aspect provides a method of constructing a frequency lookup table for an expression system, where the frequency lookup table comprises a plurality of codons. In some embodiments, the plurality of codons is five or more codons, ten or more codons, fifteen or more codons, twenty or more codons, twenty-five or more codons, between five and ten codons, or less than fifty codons. The method comprises constructing a plurality of polynucleotides, each polynucleotide in the plurality of polynucleotides encoding a predetermined polypeptide sequence, where a frequency with which a first codon is used in a first polynucleotide in the plurality of polynucleotides, relative to the frequency with which all other codons in the plurality of codons that are synonymous to the first codon are used in the first polynucleotide, is different than a frequency with which the first codon is used in a second polynucleotide in the plurality of polynucleotides, relative to the frequency with which all other codons in the plurality of codons that are synonymous to the first codon are used in the second polynucleotide. In some embodiments, the plurality of nucleotides comprises five or more polynucleotides, ten or more polynucleotides, twenty or more polynucleotides, or one hundred or more polynucleotides.

In the method, each respective polynucleotide in the plurality of polynucleotides is expressed individually in an expression system. For example, if the expression system is *E. Coli*, each respective polynucleotide is introduced into a sample of *E. Coli* (e.g., in an expression vector that is transfected into the sample of *E. Coli*) and expressed. Then, an expression property value of each respective polynucleotide in the plurality of polynucleotides in the expression system is measured thereby constructing a dataset. The dataset comprises, for each respective polynucleotide in the plurality of polynucleotides, a representation of codon occurrence in the respective polynucleotide and the measured expression property value of the respective polynucleotide. In some embodiments, the representation of codon occurrence is relative to other synonymous codons in the polynucleotide. For example, consider the case where there are two synonymous codons, termed codon A and codon B. The representation of codon occurrence in the dataset would comprise the relative frequency that codon A is used relative to codon B. In some embodiments, the representation of codon occurrence is relative to all other codons in the polynucleotide. For example, consider the case where there are thirteen different codons used in the polynucleotide. The representation of codon occurrence for any one of these codons would be relative to the collective codon occurrence of all thirteen codons, which would be the same as the number of times the codon was used divided by the total number of amino acids in the encoded polypeptide sequence. Other representations of codon occurrence are possible. For example, the number of times a codon was used in the polynucleotide could be stored in the dataset.

Next in the method a model is computed. The model comprises (i) a plurality of variables, each variable in the plurality of variables describing a frequency of occurrence of one or more codons in the first plurality of polynucleotides and (ii) a plurality of weights, each weight in the plurality of weights corresponding to one or more variables in the plurality of variables. In some embodiments, the plurality of variables consists of two or more variables, three or more variables, four or more variables, five or more variables, six or more variables, ten or more variables, twenty or more variables, between five and one hundred variables, or less then forty variables. In some embodiments, the plurality of weights consists of two or more weights, three or more weights, four or more weights, five or more weights, six or more weights, ten or more weights, twenty or more weights, between five and one hundred weights, or less then forty weights. The model describes a variation in the measured expression property values of the plurality of polynucleotides from the measuring as a function of the plurality of variables and their corresponding weights. In some embodiments, each variable is for the occurrence of a particular codon in the set of naturally occurring codons used in a polynucleotide and a weight for the variable is a significance on this codon on determining an expression property of the polynucleotide. In some embodiments, each weight in the plurality of weights is for a codon in the plurality of codons.

The method further includes refining the model by principal component analysis in which the plurality of variables in the model are reduced to a plurality of latent variables, including a first latent variable, where the plurality of latent variables collectively account for all or a portion of a variation in the measured expression property values of the plurality of polynucleotides from the measuring, and where each codon in the plurality of codons has a corresponding load in the first latent variable.

The method further includes constructing the frequency lookup table for the expression system from the final model, where the frequency lookup table provides a corresponding codon frequency range for each of two or more codons in the plurality of codons, and where the codon frequency range for a codon in the frequency lookup table is determined by the corresponding load of the codon in the first latent variable.

The method further comprises outputting the frequency lookup table to a user interface device, a tangible computer readable storage medium; or displaying the frequency lookup table in user readable form.

In some embodiments, each frequency in a frequency range for a respective codon in the frequency lookup table is a frequency that the respective codon can be incorporated into a polynucleotide relative to the frequencies of all other naturally occurring codons that are synonymous to the respective codon. In some embodiments, each frequency in a frequency range for a respective codon in the frequency lookup table is a frequency that the respective codon can be incorporated into a polynucleotide relative to the total number of amino acids in the encoded polypeptide. In some embodiments, each frequency in a frequency range for a respective codon in the frequency lookup table is a frequency that the respective codon can be incorporated into a polynucleotide relative to all other codons in the plurality of codons.

Another method in accordance with this aspect of the invention can be used for designing a test polynucleotide for expression of a polypeptide in an expression system using a frequency table, where the frequency lookup table comprises a plurality of codons. The method comprises (A) constructing a plurality of polynucleotides, each polynucleotide in the plurality of polynucleotides encoding a predetermined polypeptide sequence, where a frequency with which a first codon is used in a first polynucleotide in the plurality of polynucleotides, relative to the frequency with which all other codons in the plurality of codons that are synonymous to the first codon are used in the first polynucleotide, is different than a frequency with which the first codon is used in a second polynucleotide in the plurality of polynucleotides, relative to the frequency with which all other codons in the plurality of codons that are synonymous to the first codon are used in the second polynucleotide. The method further comprises (B) expressing each respective polynucleotide in the plurality of polynucleotides individually in the expression system. The method further comprises (C) measuring an expression property value of each respective polynucleotide in the plurality of polynucleotides in the expression system thereby constructing a dataset, where the dataset comprises, for each respective polynucleotide in the plurality of polynucleotides, a representation of codon occurrence in the respective polynucleotide and the measured expression property value of the respective polynucleotide. The method further comprises (D) computing a model comprising (i) a plurality of variables, each variable in the plurality of variables describing a frequency of occurrence of one or more codons in the first plurality of polynucleotides, and (ii) a plurality of weights, each weight in the plurality of weights corresponding to one or more variables in the plurality of variables, and where the model describes a variation in the measured expression property values of the plurality of polynucleotides from the measuring (C) as a function of the plurality of variables and their corresponding weights. The method further comprises (E) refining the model by principal component analysis in which the plurality of variables in the model are reduced to a plurality of latent variables, including a first latent variable, where the plurality of latent variables collectively account for all or a portion of a variation in the measured expression property values of the plurality of polynucleotides from the measuring C, and where each codon in the plurality of codons has a corresponding load in the first latent variable. The method further comprises (F) constructing the frequency lookup table for the expression system from the final model, where the lookup table provides a corresponding codon frequency range for each of two or more codons in the plurality of codons, and where the codon frequency range for a codon in the frequency lookup table is determined by the corresponding load of the codon in the first latent variable. The method further comprises (G) defining the test polynucleotide, where the defining comprises, for each respective codon in the frequency lookup table, determining whether the respective codon encodes a portion of the polypeptide sequence. In the method, when the respective codon encodes a portion of the polypeptide, the codon is incorporated into the test polynucleotide at a frequency of occurrence that is within the frequency range specified for the respective codon in the frequency lookup table. The method further comprises (H) outputting the test polynucleotide sequence to a user interface device, a tangible computer readable storage medium; or displaying the test polynucleotide sequence in user readable form. In some embodiments, each frequency in a frequency range for a respective codon in the frequency lookup table is a frequency that the respective codon can be incorporated into the test polynucleotide relative to all other naturally occurring codons that are synonymous to the respective codon. In some embodiments, each frequency in a frequency range for a respective codon in the frequency lookup table is a frequency that the respective codon can be incorporated into the test polynucleotide relative to all other codons in the plurality of codons. In some embodiments, each frequency in a frequency range for a respective codon in the frequency lookup table is a frequency that the respective codon can be incorporated into the test polynucleotide relative to all other naturally occurring codons.

Another aspect provides a method of constructing a frequency lookup table for an expression system, where the frequency lookup table comprises a plurality of sequence elements and optionally a reading frame designation relative to the reading frame of a polypeptide encoded by the polynucleotide. The method comprises constructing a plurality of polynucleotides, each polynucleotide in the plurality of polynucleotides encoding a predetermined polypeptide sequence, where a frequency with which a first sequence element is used in a first polynucleotide in the plurality of polynucleotides is different than a frequency with which the first sequence element is used in a second polynucleotide in the plurality of polynucleotides. The method further comprises (B) expressing each respective polynucleotide in the plurality of polynucleotides individually in the expression system. The method further comprises (C) measuring an expression property value of each respective polynucleotide in the plurality of polynucleotides in the expression system thereby constructing a dataset, where the dataset comprises, for each respective polynucleotide in the plurality of polynucleotides, a representation of sequence element occurrence in the respective polynucleotide and the measured expression property value of the respective polynucleotide. The method further comprises (D) computing a model comprising (i) a plurality of variables (e.g., two or more variables, three or more variables, four or more variables, ten or more variables, between two and fifty variables, less than forty variables, etc.), each variable in the plurality of variables describing a frequency of occurrence of one or more sequence elements in the first plurality of polynucleotides, and (ii) a plurality of weights (e.g., two or more weights, three or more weights, four or more weights, ten or more weights, between two and fifty weights, less than forty weights, etc.), each weight in the plurality of weights corresponding to one or more variables in the plurality of variables, and where the model describes a variation in the measured expression property values of the plurality of polynucleotides from the measuring (C) as a function of the plurality of variables and their corresponding weights. The method further comprises (E) refining the model by principal component analysis in which the plurality of variables in the model are reduced to a plurality of latent variables, including a first latent variable, where the plurality of latent variables collectively account for all or a portion of a variation in the measured expression property values of the plurality of polynucleotides from the measuring C, and where each sequence element in the plurality of sequence elements has a corresponding load in the first latent variable. The method further comprises (F) constructing the frequency lookup table for the expression system from the final model, where the frequency lookup table provides a corresponding sequence element frequency range for each of two or more sequence elements in the plurality of sequence elements, and where the codon frequency range for a sequence element in the frequency lookup table is determined by the corresponding load of the sequence element in the first latent variable. The method further comprises (G) outputting the frequency lookup table to a user interface device, a tangible computer readable storage medium; or displaying the frequency lookup table in user readable form.

Another aspect of the invention provides a method for designing a test polynucleotide for expression of a polypeptide in an expression system, where the frequency lookup table comprises a plurality of sequence elements and optionally a reading frame designation relative to the reading frame of a polypeptide encoded by the polynucleotide. In this aspect, the method comprises (A) constructing a plurality of polynucleotides, each polynucleotide in the plurality of polynucleotides encoding a predetermined polypeptide sequence, where a frequency with which a first sequence element is used in a first polynucleotide in the plurality of polynucleotides is different than a frequency with which the first sequence element is used in a second polynucleotide in the plurality of polynucleotides. The method further comprises (B) expressing each respective polynucleotide in the plurality of polynucleotides individually in the expression system. The method further comprises (C) measuring an expression property value of each respective polynucleotide in the plurality of polynucleotides in the expression system thereby constructing a dataset, where the dataset comprises, for each respective polynucleotide in the plurality of polynucleotides, a representation of sequence element occurrence in the respective polynucleotide and the measured expression property value of the respective polynucleotide. The method further comprises (D) computing a model comprising (i) a plurality of variables, each variable in the plurality of variables describing a frequency of occurrence of one or more sequence elements in the first plurality of polynucleotides, and (ii) a plurality of weights, each weight in the plurality of weights corresponding to one or more variables in the plurality of variables, and where the model describes a variation in the measured expression property values of the plurality of polynucleotides from the measuring (C) as a function of the plurality of variables and their corresponding weights. The method further comprises (E) refining the model by principal component analysis in which the plurality of variables in the model are reduced to a plurality of latent variables, including a first latent variable, where the plurality of latent variables collectively account for all or a portion of a variation in the measured expression property values of the plurality of polynucleotides from the measuring (C), and where each sequence element in the plurality of sequence elements has a corresponding load in the first latent variable. The method further comprises (F) constructing the frequency lookup table for the expression system from the final model, where the frequency lookup table provides a corresponding sequence element frequency range for each of two or more sequence elements in the plurality of sequence elements, and where the sequence element frequency range for a sequence element in the frequency lookup table is determined by the corresponding load of the sequence element in the first latent variable. The method further comprises (G) defining the test polynucleotide, where the defining comprises, for each respective sequence element in the frequency lookup table, determining whether the respective sequence element encodes a portion of the polypeptide sequence, where, when the respective sequence element encodes a portion of the polypeptide, the sequence element is incorporated into the test polynucleotide at a frequency of occurrence that is within the frequency range specified for the respective sequence element in the frequency lookup table. The method further comprises (H) outputting the test polynucleotide sequence to a user interface device, a tangible computer readable storage medium; or displaying the test polynucleotide sequence in user readable form.

5.6 DESIGN OF NEW SEQUENCE ELEMENT FREQUENCY LOOKUP TABLES

Analyses of the expression properties and frequencies of codons or other sequence elements in a codon variant set of polynucleotides can be used to identify frequencies or ranges of frequencies for sequence elements, such as codons, codon pairs and nucleotide triplets in the +3 reading frame within a polynucleotide that result in superior expression properties. The results of this analysis can be formulated as a frequency lookup table to be used in the design of polynucleotide sequences. In this way the expression properties of one codon variant set may be translated to design principles that can be used in the design of polynucleotides encoding polypeptides that are unrelated to the initial codon variant set. The extraction of polynucleotide design principles from codon variant sets are an aspect of the invention.

5.6.1 Sequence Element Frequency Lookup Tables Based Directly on Variants in a Codon Variant Set In a preferred embodiment of the invention, the absolute or relative frequencies of one or more sequence elements (e.g., codons) in the variant in the codon [valiant] variant set that has the most desirable expression property or properties are used as sequence element target frequencies for the design of other polynucleotides. The sequence element target frequencies can be encoded as a sequence element frequency lookup table, or as a codon frequency matrix, or otherwise used to calculate a desired score for a polynucleotide encoding a polypeptide.

Such sequence element target frequencies can be used to design polynucleotides to encode polypeptides that may or may not be related to the polypeptides present in the codon variant set. The frequency of each sequence element within the designed polynucleotides will preferably be between 1.5 times and 0.5 times the target codon frequencies, more preferably between 1.25 times and 0.75 times the target codon frequencies. In some embodiments the acceptable range of frequencies of sequence elements is explicitly defined.

In a variation of this embodiment of the invention, target codon frequencies can be derived from the 2 or 3 or 4 or 5 or 6 or 7 or 8 or 9 or 10 variants in the codon-variant set that have the most desirable expression property or properties, for example by calculating an arithmetic or geometric mean value for the codon frequency found in these best variants.

5.6.2 Adjusting Frequency Lookup Tables

In some instances, sequence element target frequencies for the design of other polynucleotides can be calculated by more complex sequence-expression modeling. For example relative or absolute frequencies for one or more of the codons for amino acids with multiple codon choices, or other sequence elements such as nucleotide triplets in the +3 reading frame (which encodes the "wobble" or third base of one codon and the first two bases of the following codon) and nucleotide hexamers in the +1 reading frame (which encode an adjacent pair of codons or "codon pair") can be used as the input independent variables for sequence-expression modeling. In this embodiment the resulting independent variable matrix contains one or more discrete values for each of the variables. Multivariate regression analysis or other sequence-expression analysis can then be applied to determine correlation of an expression property with the relative or absolute frequencies for one or more of the codons for amino acids with multiple codon choices, or other sequence elements. The resulting model can show which codon frequencies for each amino acid correlate most strongly with desired expression properties, or which other sequence elements correlate most strongly with desired expression properties. A new codon frequency lookup table can be constructed, for example, by using the codon frequency for each amino acid that the sequence-expression model correlates most strongly with desired expression properties.

In another embodiment of the invention the degree of bias relative to a reference relative frequency of synonymous codons can be used as the input independent variables for sequence-expression modeling. A codon variant set can be created by varying the codon bias for each amino acid systematically using Design of Experiments methodology. In this embodiment the resulting independent variable matrix would contain two or more discrete values for each of the 18 variables (e.g. "more" or "less" biased). Multivariate regression analysis could then be applied to determine correlation of the biases by amino acid with expression. The resulting model would suggest which amino acid codon sets should be more and which should be less biased. An optimal combination of the biases that show the strongest positive contribution to expression can then be constructed and used as an optimized codon frequency lookup table.

Codon biases calculated from analyzing sequence-expression data can in turn be used as the starting point for another experiment to determine whether more or less bias for each amino acid relative to this new table is beneficial. Iterations of this procedure could be used to find an optimum for each amino acid and, thus, an optimal complete codon table.

Alternatively the new frequency lookup tables or biases or matrices can simply be used to determine sequence element target frequencies in new polynucleotides.

5.6.3 Frequency Lookup Tables with Frequency Ranges

There are frequently multiple design criteria that must be followed in the design of synthetic polynucleotides. For polynucleotides that encode polypeptides, one constraint is that the polynucleotide should express. Other constraints can include (i) exclusion of a restriction site sequence; (ii) incorporation of a restriction site sequence in the polynucleotide sequence; (iii) a designation of a target G+C content in the polynucleotide sequence; (iv) an allowable length of a subsequence that is exactly repeated within either strand of the polynucleotide sequence; (v) an allowable annealing temperature of any sub-sequence to any other sub-sequence within either strand of the polynucleotide sequence; (vi) exclusion of a hairpin turn in the polynucleotide sequence; (vii) exclusion of a repeat element in the polynucleotide sequence; (viii) exclusion of a ribosome binding site in the polynucleotide sequence; (ix) exclusion of a polyadenylation signal in the polynucleotide sequence; (x) exclusion of a splice site in the polynucleotide sequence; (xi) exclusion of an open reading frame greater than a certain length in each possible 5' to 3' reading frame in the polynucleotide sequence; (xii) exclusion of a polynucleotide sequence that facilitates RNA degradation in the polynucleotide sequence; (xiii) exclusion of an RNA polymerase termination signal in the polynucleotide sequence; (xiv) exclusion of a transcriptional promoter in the polynucleotide sequence; (xv) exclusion of an immunostimulatory sequence in the polynucleotide sequence; (xvi) incorporation of an immunostimulatory sequence in the polynucleotide sequence; (xvii) exclusion of an RNA methylation signal in the polynucleotide sequence; (xviii) exclusion of a selenocysteine incorporation signal in the polynucleotide sequence; (xix) exclusion of an RNA editing sequence in the polynucleotide sequence; (xx) exclusion of an RNAi-targeted sequence in the polynucleotide sequence; (xxi) exclusion of an inverted repeat within the polynucleotide sequence and/or (xxii) exclusion of a DNA methylation signal in the polynucleotide sequence A polynucleotide sequence can be designed to fit many design criteria simultaneously by defining quantifiable polynucleotide sequence properties or combination of properties. The properties can also be described as the presence or absence of a feature (represented as a binary or Boolean term). For example the design criteria can be achieved by a Monte Carlo algorithm: (1) select an initial codon sequence to encode a polypeptide; (2) quantify the one or more polynucleotide sequence properties of interest; (3) identify a possible change to the codon sequence that does not change the encoded polypeptide; (4) quantify the one or more polynucleotide sequence properties of interest for the polynucleotide sequence after the change in codon sequence; (5) accept or reject the change based on a function of the difference in values for the one or more polynucleotide properties of interest for the original and the unchanged codon sequences; and (6) repeat this process until a desired value for the one or more polynucleotide sequence properties of interest is obtained. Searches for codon sequences that have defined values for one or more quantifiable polynucleotide sequence property can also be performed by evolving the sequence using genetic algorithms or genetic algorithms in combination with monte carlo algorithms, or other stochastic searches such as simulated annealing, Boltzmann learning.

One example of how to perform such a design is as follows:

---

Select an initial polynucleotide sequence encoding a polypeptide; then
for 10000 iterations
{
    i. Calculate the values for all of the quantifiable
       polynucleotide sequence properties corresponding to
       design criteria;
    ii. Compare these values with the desired values for all of the
       quantifiable polynucleotide sequence properties
       corresponding to design criteria;
    iii. Randomly choose one codon in the polynucleotide;
    iv. Randomly change the codon for a synonymous codon;
    v. For the new polynucleotide calculate the values for all of
       the quantifiable polynucleotide sequence properties
       corresponding to design criteria;

-continued vi. Compare these values with the desired values for all of the
       quantifiable polynucleotide sequence properties
       corresponding to design criteria;
    vii. If the values for the polynucleotide created in step iv) more
       closely match the design criteria than the polynucleotide of
       step i), accept the change from step iv), else, dismiss the
       changes and retain original values.
}
Output a polynucleotide sequence.

---

In some embodiments, it is advantageous to precisely control the frequencies of some sequence elements while less precisely controlling the frequencies of other sequence elements. In particular it is advantageous to less precisely control the frequencies of sequence elements whose frequencies are less critical for determining the expression property of the polynucleotide. If there are multiple design criteria in addition to sequence element frequency, relaxing the design constraints on sequence elements whose frequencies are less functionally critical increases the sequence possibilities that can be used to meet the other design criteria.

Sequence-expression modeling can produce values for the absolute or relative frequency for each codon that best correlates with desired expression properties. It can also produce a measure of the importance of each sequence element in determining the expression properties, or the acceptable range of frequencies for each sequence element that are consistent with certain desired expression properties. Frequency lookup tables can be created from sequence-expression relationships to describe a target range of relative or absolute frequencies for each sequence element instead of the single value for each sequence element that is found in codon bias tables that describe the frequencies of codons found in naturally occurring sequences or genomes. These frequency lookup tables can thus provide a target range for the frequency of each sequence element in a designed polynucleotide, rather than a single target value. This is particularly advantageous when the frequencies of some sequence elements have strong correlations with desired expression properties and the frequencies of other sequence elements appear to be less important.

5.6.4 Use of Frequency Lookup Tables to Design a Final Polynucleotide

Another aspect provides methods of using one or more frequency lookup tables to design a final polynucleotide that encodes an amino acid sequence of a predetermined polypeptide. For instance, in one such method a frequency lookup table corresponding to an expression system is obtained. The frequency lookup table comprises a plurality of sequence elements and a plurality of frequency ranges. Each frequency range in the plurality of frequency ranges is for a corresponding sequence element in the plurality of sequence elements. Each respective frequency range in the plurality of frequency ranges specifies a range of frequencies that the sequence element corresponding to the respective frequency range can occur in a polynucleotide that is to be expressed in the expression system. Each sequence element in the plurality of sequence elements is optionally associated with a frame designation in the frequency lookup table. For instance, the frequency lookup table may specify a frequency range for a given sequence element in the reading frame that encodes the amino acid sequence of a predetermined polypeptide. In this instance, the frequency lookup table is only constraining the frequency range of the sequence element in the reading frame that encodes the amino acid sequence of the predetermined polypeptide, not other frames. The frequency lookup table does not constrain the frequency that the sequence element appears in other frames. For example, consider the case where the sequence element is the codon TTT and the frequency lookup table specifies that the frame for TTT is the reading frame that encodes the amino acid sequence of the predetermined polypeptide. The sequence TTT may appear in other reading frames (e.g., split across two codons) but the frequency lookup table does not place a constraint on such occurrences. Of course, the frequency lookup table can be used to place frequency ranges on multiple frames for a given sequence element. Further, the frequency lookup table can be used to place a first frequency range on a given sequence element when the sequence element is in one frame and a second frequency range on a given sequence element when the sequence element is in a second frame, where the two frequency ranges are different. By different, what is meant here is that the two frequency ranges have a different maximum and/or minimum. Frequency ranges can be given as absolute numbers (e.g., a maximum or minimum specific number of occurrences allowed in the designated frame), relative frequencies (e.g., in the case where the sequence element is a codon, the minimum and maximum percentage of occurrence of the codon relative to all other synonymous codons regardless of the number of times the corresponding amino acid appears in the polynucleotide sequence), absolute frequencies (e.g., the minimum and maximum percentage of occurrence of the sequence element relative to all other sequence elements in the frequency lookup table), absolute relative frequencies (e.g., the minimum and maximum percentage of occurrence of the sequence element relative to a list of other sequence elements specified in the frequency lookup table), or some other metric that involves a range of allowed occurrences of the sequence element. An example of the case of absolute relative frequency, the frequency lookup table specifies a first sequence element, an optional frame, and a list of sequence elements that serve as a basis for constraining the occurrence of the first sequence element in the polynucleotide. For example, consider the case where the sequence element is labeled "A" and the list of sequence elements consists of the sequence elements labeled "B," "C," and "D." In this case, the frequency range allowed or "A" is relative to the sum total of the occurrence of "B." "C," and "D" in the designated reading frame of the polynucleotide.

In the method a test polynucleotide that encodes the amino acid sequence is defined. Further, a score for the test polynucleotide is determined using the frequency lookup table, where the score determined for the test polynucleotide is collectively determined by a plurality of agreement scores, each agreement score in the plurality of agreement scores being a measure of agreement between (i) an actual sequence element frequency of a respective sequence element in the plurality of sequence elements in the test polynucleotide and (ii) a frequency range specified for the respective sequence element in the frequency lookup table or a measure of agreement between (iii) an actual quantifiable sequence property of the test polynucleotide and (iv) a value range specified for the respective quantifiable sequence property in the lookup table. For example, consider a lookup table that contains three sequence elements and three corresponding frequency ranges. A test polynucleotide in this example is scored by determining three agreement scores. Each agreement score is a function of how well the frequency of occurrence in the test polynucleotide of one of the three sequence elements fits into the frequency ranges specified for the sequence element in the frequency lookup table. In some embodiments, the agreement score approaches a predetermined ideal score when the frequency of occurrence of the sequence element in the test polynucleotide approaches the middle of the frequency range specified in the frequency lookup table for the sequence element. In some embodiments, the agreement score approaches a predetermined ideal score when the frequency of occurrence of the sequence element in the test polynucleotide approaches the minimum allowed frequency in the frequency range specified in the frequency lookup table for the sequence element. In some embodiments, the agreement score approaches a predetermined ideal score when the frequency of occurrence of the sequence element in the test polynucleotide approaches the maximum allowed frequency in the frequency range specified in the frequency lookup table for the sequence element. By "approaches a predetermined ideal score" it is meant that the score becomes closer to a score that is considered to be optimal. The optimal score can, for example, be a high value, such as 100, or a low value such as zero. Thus, consider the case where the optimal score is zero and the agreement score approaches a predetermined ideal score when the frequency of occurrence of the sequence element in the test polynucleotide approaches the maximum allowed frequency in the frequency range specified in the frequency lookup table for the sequence element. In this case, the agreement score approaches zero when the frequency of occurrence of the sequence element in the test polynucleotide approaches the maximum allowed frequency in the frequency range specified in the frequency lookup table for the sequence element.

In some embodiments, each of the agreement scores (from each of the sequence elements in the frequency lookup table) are summed together to obtain the score for the test polynucleotide. In some embodiments, each of the agreement scores (from each of the sequence elements in the frequency lookup table) are summed together to obtain the score for the test polynucleotide but individual agreement scores are weighted by how often they appear in the test polynucleotide in the reading frame specified by the frequency lookup table. In some embodiments, any mathematical function is used to combine the agreement scores into the score for the test polynucleotide. For example, the agreement scores can be multiplied together. In some embodiments the sum of the squares of the differences between all of the (i) actual sequence element frequencies of a respective sequence element in the plurality of sequence elements in the test polynucleotide and (ii) the frequency range specified for the respective sequence element in the frequency lookup table and/or the differences between all of the (iii) actual quantifiable sequence property of the test polynucleotide and (iv) a value range specified for the respective quantifiable sequence property in the lookup table. In some embodiments, the predetermined ideal score for the test polynucleotide is a low value and the lower the score computed for the test polynucleotide (by combination of all the individual agreement scores), the closer this score is to the predetermined ideal score. In some embodiments, the predetermined ideal score for the test polynucleotide is a high value and the higher the score computed for the test polynucleotide (by combination of all the individual agreement scores), the closer this score is to the predetermined ideal score.

In the method, the test polynucleotide is then processed. Such processing assumes a case where there are multiple instances of the defining and determining described above, with each instance of the defining and determining resulting in a different test polynucleotide with a score. The processing is used to decide which test polynucleotide to keep and which test polynucleotides to reject based on their respective scores. In some embodiments, an instance of this processing is run after each instance of the defining and determining in order to decide whether to keep the newly determined test polynucleotide or to reject the newly determined test polynucleotide in favor of a previously determined polynucleotide. In some embodiments, this processing comprises accepting the recently determined test polynucleotide when (i) the test polynucleotide has a score that is closer to a predetermined ideal score than any other score assigned to a test polynucleotide. If there is no other test polynucleotide that has been determined, then the test polynucleotide is deemed to have a score that is closer to a predetermined ideal score than any other score assigned to a test polynucleotide. The test polynucleotide is rejected when another test polynucleotide in an instance of the determining (e.g., computed before the last instance of the determining) has a score that is closer to an ideal score than the score assigned to the test polynucleotide in the last instance of defining and determining. In some embodiments, the ideal score is a low value (e.g. zero or some negative value). In some embodiments, the ideal score is a high value (e.g. one or some other positive value).

The defining, determining, and processing are repeated until an exit condition is achieved, where the test polynucleotide to be accepted by the last instance of the processing before the exit condition is achieved is deemed to be the final polynucleotide. The final polynucleotide is then outputted to a user interface device, a tangible computer readable storage medium, or the final polynucleotide is displayed in user readable form. In some embodiments, the exit condition is the repetition of the defining, determining, and processing a predetermined number of times (e.g., two or more times, three or more times, four or more times, between five and one hundred times, more than ten times, or than one thousand times, more than one hundred thousand times, or more than one million times).

In some embodiments, the exit condition is the repetition of the defining, determining, and processing until a score for a test polynucleotide computed in an instance of the determining is within a predetermined threshold of an ideal score. The actual value of the predetermined threshold is application dependent. For instance, the predetermined threshold will depend upon the mathematical function that is used to combine individual agreement scores into the score for a test polynucleotide.

An advantage of the methods described in this section is that the defining of a test polynucleotide can accommodate many different design criteria. These design criteria can be absolute, such as the exclusion of a specific sequence element or they can be constrained to frequency ranges specified in a frequency lookup table, or they can be constrained to specific values specified in a quantifiable sequence property lookup table, or they can be associated with specific values for scores or penalties. In some embodiments, the designing of a test polynucleotide above further comprises (i) exclusion of a restriction site sequence in the test polynucleotide, (ii) incorporation of a restriction site sequence in the test polynucleotide, (iii) a designation of a target G+C content in the test polynucleotide, (iv) exclusion of a sub-sequence, longer than an allowable length, that is exactly repeated within either strand of the test polynucleotide, (v) exclusion of a first sub-sequence that can anneal at a greater than an allowable annealing temperature to a second sub-sequence within either strand of the test polynucleotide, (vi) exclusion of a hairpin turn in the test polynucleotide, (vii) exclusion of a repeat element in the test polynucleotide, (viii) exclusion of a ribosome binding site in the test polynucleotide, (ix) exclusion of a polyadenylation signal in the test polynucleotide, (x) exclusion of a splice site in the test polynucleotide, (xi) exclusion of an open reading frame in each possible reading frame in the test polynucleotide other than a reading frame encoding the amino acid sequence, (xii) exclusion of a polynucleotide sequence that facilitates RNA degradation in the test polynucleotide, (xiii) exclusion of an RNA polymerase termination signal in the test polynucleotide, (xiv) exclusion of a transcriptional promoter in the test polynucleotide, (xv) exclusion of an immunostimulatory sequence in the test polynucleotide, (xvi) incorporation of an immunostimulatory sequence in the test polynucleotide, (xvii) exclusion of an RNA methylation signal in the test polynucleotide, (xviii) exclusion of a selenocysteine incorporation signal in the test polynucleotide, (xix) exclusion of an RNA editing sequence in the test polynucleotide, (xx) exclusion of an RNAi-targeted sequence in the test polynucleotide, (xxi) exclusion of an inverted repeat within the first x number of nucleotides encoding the amino acid sequence in the test polynucleotide, where x is any value between one nucleotide and one hundred nucleotides, or (xxii) exclusion of a DNA methylation signal in the test polynucleotide.

In some embodiments, the score determined for a test polynucleotide in an instance of the determining is further determined by (i) exclusion of a restriction site sequence in the test polynucleotide, (ii) incorporation of a restriction site sequence in the test polynucleotide, (iii) a designation of a target G+C content in the test polynucleotide, (iv) exclusion of a sub-sequence, longer than an allowable length, that is exactly repeated within either strand of the test polynucleotide, (v) exclusion of a first sub-sequence that can anneal at a greater than an allowable annealing temperature to a second sub-sequence within either strand of the test polynucleotide, (vi) exclusion of a hairpin turn in the test polynucleotide, (vii) exclusion of a repeat element in the test polynucleotide, (viii) exclusion of a ribosome binding site in the test polynucleotide, (ix) exclusion of a polyadenylation signal in the test polynucleotide, (x) exclusion of a splice site in the test polynucleotide, (xi) exclusion of an open reading frame in each possible reading frame in the test polynucleotide other than a reading frame encoding the amino acid sequence, (xii) exclusion of a polynucleotide sequence that facilitates RNA degradation in the test polynucleotide, (xiii) exclusion of an RNA polymerase termination signal in the test polynucleotide, (xiv) exclusion of a transcriptional promoter in the test polynucleotide, (xv) exclusion of an immunostimulatory sequence in the test polynucleotide, (xvi) incorporation of an immunostimulatory sequence in the test polynucleotide, (xvii) exclusion of an RNA methylation signal in the test polynucleotide, (xviii) exclusion of a selenocysteine incorporation signal in the test polynucleotide, (xix) exclusion of an RNA editing sequence in the test polynucleotide, (xx) exclusion of an RNAi-targeted sequence in the test polynucleotide, (xxi) exclusion of an inverted repeat within the first x nucleotides encoding the amino acid sequence in the test polynucleotide, where x is any number between one nucleotide and one hundred nucleotides, or (xxii) exclusion of a DNA methylation signal in the test polynucleotide. For example, in some embodiments, the score for a test polynucleotide is adjusted so that it is closer to an ideal value when the test polynucleotide does not have a restriction sequence that is to be excluded from test polynucleotide. In another example, in some embodiments, the score for a test polynucleotide is adjusted so that it is closer to an ideal value when the test polynucleotide incorporates a restriction sequence that is to be included in the test polynucleotide. In another example, in some embodiments, the score for a test polynucleotide is adjusted so that it is further away from an ideal value when the test polynucleotide contains a sub-sequence, longer than an allowable length, that can be exactly repeated within either strand of the test polynucleotide. Such a sub-sequence may be undesirable because the repeats of the sub-sequence may anneal to each other and prevent translation of the polynucleotide.

In some embodiments, the frequency lookup table further comprises a model that computes an estimated expression property value for an expression property of the predetermined polypeptide as a function of a sequence of a test polynucleotide for the expression system, and where the score determined for a respective test polynucleotide in an instance of the determining is further determined by the estimated expression property value for the predetermined polypeptide calculated by the model based on a nucleotide sequence of the respective test polynucleotide. In some embodiments, the expression property is an estimate of a total amount of protein encoded by the respective test polynucleotide when expressed in the expression system in a predetermined period of time. In some embodiments, the expression property is an estimate of a total amount of active protein encoded by the respective test polynucleotide when expressed in the expression system in a predetermined period of time. In some embodiments, the expression property is an estimate of a total amount of soluble protein encoded by the respective test polynucleotide when expressed in the expression system in a predetermined period of time. This model can be created by evaluation of a codon variant set (plurality of nucleotides) in the expression system being used to express the final polynucleotide using any of the methods disclosed herein.

In some embodiments, the sequence element in the plurality of sequence elements consists of a codon. In some embodiments, a sequence element in the plurality of sequence elements consists of a codon pair. A codon pair is a predetermined first codon and predetermined second codon that are adjacent to each other and are in the same reading frame. In some embodiments, a sequence element in the plurality of sequence elements consists of a nucleotide triplet in the +3 reading frame (which encodes the "wobble" or third base of one codon and the first two bases of the following codon)

In some embodiments, the plurality of sequence elements consists of up to five, up to ten, up to fifteen, up to twenty, up to twenty-five, or up to thirty naturally occurring codons and the frequency lookup table places no restrictions on the frequency of occurrence of a codon in a test sequence when the codon is not in the frequency lookup table.

Another aspect provides a computer-readable medium storing one or more computer programs executable by a computer, the one or more computer programs collectively comprising instructions for performing any of the methods described in this section. Another aspect provides an apparatus comprising one or more processors and a memory, coupled to the one or more processors, the memory storing one or more computer programs that individually or collectively comprise instructions for performing any of the methods disclosed in this section.

5.6.5 Use of Frequency Lookup Tables and a Genetic Algorithm to Design a Final Polynucleotide Another aspect of the invention comprises designing a final polynucleotide that encodes an amino acid sequence of a predetermined polynucleotide using a genetic algorithm. In the method, a frequency lookup table corresponding to an expression system is obtained. The frequency lookup table comprises a plurality of sequence elements and a plurality of frequency ranges. Each frequency range in the plurality of frequency ranges is for a corresponding sequence element in the plurality of sequence elements. Each respective frequency range in the plurality of frequency ranges specifies a range of frequencies that the sequence element corresponding to the respective frequency range can occur in a polynucleotide that is to be expressed in the expression system. Each sequence element in the plurality of sequence elements is optionally associated with a frame designation in the frequency lookup table. In some embodiments, the plurality of sequence elements is five or more sequence elements, ten or more sequence elements, fifteen or more sequence elements, twenty or more sequence elements, twenty-five or more sequence elements, between five and ten sequence elements, or less than fifty sequence elements. In the methods, a set of test polynucleotides is defined, where each test polynucleotide in the set of test polynucleotides encodes the amino acid sequence. Then, a fit of each test polynucleotide in the set of test polynucleotides is determined, where the fit of a respective test polynucleotide in the set of test polynucleotides is determined by a combination of a plurality of agreement scores, each agreement score in the plurality of agreement scores being a measure of agreement between (i) an actual sequence element frequency of a respective sequence element in the plurality of sequence elements in the respective test polynucleotide sequence and (ii) a frequency range specified for the respective sequence element in the frequency lookup table or a measure of agreement between (iii) an actual quantifiable sequence property of the test polynucleotide and (iv) a value range specified for the respective quantifiable sequence property in the lookup table. Then a determination as to whether an exit condition has been satisfied is made. When the exit condition has not been satisfied, the set of test polynucleotides is enriched by removing a portion of the polynucleotides from the set of test polynucleotides based on a respective fit determined for each test polynucleotide in the set of test polynucleotides. When the exit condition has not been satisfied, the set of test polynucleotides is also enriched by adding a subset of test polynucleotides to the set of test polynucleotides, where each test polynucleotide in the subset of test polynucleotides is derived from one or more test polynucleotides already in the set of test polynucleotides and where each test polynucleotide in the subset of test polynucleotides encodes the amino acid sequence of the predetermined polypeptide. The steps of determining a fit, determining an exit condition, enriching by removing polynucleotides, and enriching by adding polynucleotides is repeated until the exit condition has been satisfied. A final polynucleotide from the set of test polynucleotides is outputted to a user interface device, a tangible computer readable storage medium; or the final polynucleotide is displayed in user readable form. In some embodiments, the final polynucleotide is a test polynucleotide in the set of test polynucleotides that has a fit that is closer to an ideal fit than any other test polynucleotide in the set of test polynucleotides. In some embodiments the exit condition is the repetition of the determining a fit, the determining an exit condition, the enriching by removal, and the enriching by repeating a predetermined number of times. In some embodiments, the exit condition is the repetition of the determining a fit, the determining whether an exit condition has not been satisfied, the enriching through removal of polynucleotides, and the enriching through adding derived polynucleotides until a fit of a test polynucleotide computed in an instance of the determining whether an exit condition is within a predetermined threshold of an ideal score. The exact value of the predetermined threshold is application dependent. Further, in some embodiments the ideal score is a minimum possible score, a maximum possible score, or a specific predetermined value.

In some embodiments, the defining a set of test polynucleotides comprises exclusion of a restriction site sequence in a test polynucleotide in the set of test polynucleotides, (ii) incorporation of a restriction site sequence in a test polynucleotide in the set of test polynucleotides, (iii) a designation of a target G+C content in a test polynucleotide in the set of test polynucleotides, (iv) exclusion of a sub-sequence, longer than an allowable length, that can be exactly repeated within either strand of a test polynucleotide in the set of test polynucleotides, (v) exclusion of a first sub-sequence that can anneal at a greater than an allowable annealing temperature to a second sub-sequence within either strand of a test polynucleotide in the set of test polynucleotides, (vi) exclusion of a hairpin turn in a test polynucleotide in the set of test polynucleotides, (vii) exclusion of a repeat element in a test polynucleotide in the set of test polynucleotides, (viii) exclusion of a ribosome binding site in a test polynucleotide in the set of test polynucleotides, (ix) exclusion of a polyadenylation signal in a test polynucleotide in the set of test polynucleotides, (x) exclusion of a splice site in a test polynucleotide in the set of test polynucleotides, (xi) exclusion of an open reading frame in each possible reading frame in a test polynucleotide in the set of test polynucleotides other than the reading frame encoding the predetermined polypeptide, (xii) exclusion of a polynucleotide sequence that facilitates RNA degradation in a test polynucleotide in the set of test polynucleotides, (xiii) exclusion of an RNA polymerase termination signal in a test polynucleotide in the set of test polynucleotides, (xiv) exclusion of a transcriptional promoter in a test polynucleotide in the set of test polynucleotides, (xv) exclusion of an immunostimulatory sequence in a test polynucleotide in the set of test polynucleotides, (xvi) incorporation of an immunostimulatory sequence in a test polynucleotide in the set of test polynucleotides, (xvii) exclusion of an RNA methylation signal in a test polynucleotide in the set of test polynucleotides, (xviii) exclusion of a selenocysteine incorporation signal in a test polynucleotide in the set of test polynucleotides, (xix) exclusion of an RNA editing sequence in a test polynucleotide in the set of test polynucleotides, (xx) exclusion of an RNAi-targeted sequence in a test polynucleotide in the set of test polynucleotides, (xxi) exclusion of an inverted repeat within the first 45 nucleotides encoding the amino acid sequence in a test polynucleotide in the set of test polynucleotides or (xxii) exclusion of a DNA methylation signal in a test polynucleotide in the set of test polynucleotides.

In some embodiments, the fit that is determined for a test polynucleotide in an instance of the determining whether an exit condition has been satisfied is further determined by (i) exclusion of a restriction site sequence in a test polynucleotide in the test polynucleotide, (ii) incorporation of a restriction site sequence in the test polynucleotide, (iii) a designation of a target G+C content in the test polynucleotide, (iv) exclusion of a sub-sequence, longer than an allowable length, that can be exactly repeated within either strand of the test polynucleotide, (v) exclusion of a first sub-sequence that can anneal at a greater than an allowable annealing temperature to a second sub-sequence within either strand of the test polynucleotide, (vi) exclusion of a hairpin turn in the test polynucleotide, (vii) exclusion of a repeat element in the test polynucleotide, (viii) exclusion of a ribosome binding site in the test polynucleotide, (ix) exclusion of a polyadenylation signal in the test polynucleotide, (x) exclusion of a splice site in the test polynucleotide, (xi) exclusion of an open reading frame in each possible reading frame in the test polynucleotide in other than the reading frame encoding the predetermined polypeptide, (xii) exclusion of a polynucleotide sequence that facilitates RNA degradation in the test polynucleotide, (xiii) exclusion of an RNA polymerase termination signal in the test polynucleotide, (xiv) exclusion of a transcriptional promoter in the test polynucleotide, (xv) exclusion of an immunostimulatory sequence in the test polynucleotide, (xvi) incorporation of an immunostimulatory sequence in the test polynucleotide, (xvii) exclusion of an RNA methylation signal in the test polynucleotide, (xviii) exclusion of a selenocysteine incorporation signal in the test polynucleotide, (xix) exclusion of an RNA editing sequence in the test polynucleotide, (xx) exclusion of an RNAi-targeted sequence in the test polynucleotide, (xxi) exclusion of an inverted repeat within the first x nucleotides encoding the amino acid sequence in the test polynucleotide, where x is any number between one nucleotide and one hundred nucleotides, or (xxii) exclusion of a DNA methylation signal in the test polynucleotide. For example, in some embodiments, the fit for a test polynucleotide is adjusted so that it is closer to an ideal value when the test polynucleotide does not have a restriction sequence that is to be excluded from test polynucleotide. In another example, in some embodiments, the fit for a test polynucleotide is adjusted so that it is closer to an ideal value when the test polynucleotide incorporates a restriction sequence that is to be included in the test polynucleotide. In another example, in some embodiments, the fit for a test polynucleotide is adjusted so that it is further away from an ideal value when the test polynucleotide contains a sub-sequence, longer than an allowable length, that can be exactly repeated within either strand of the test polynucleotide. Such a sub-sequence may be undersirable because the repeats of the sub-sequence may anneal to each other and prevent translation of the polynucleotide.

In some embodiments, the frequency lookup table further comprises a model that computes an estimated expression property value for an expression property of the predetermined polypeptide as a function of a nucleotide sequence of a test polynucleotide, and wherein the fit determined for a respective test polynucleotide in an instance of the determining a fit of a respective test polynucleotide in the set of test polynucleotides is further determined by the estimated expression property value for the predetermined polypeptide calculated by the model based on a nucleotide sequence of the respective test polynucleotide. In some embodiments, the expression property is an estimate of a total amount of protein encoded by the respective test polynucleotide when expressed in the expression system in a predetermined period of time. In some embodiments, the expression property is an estimate of a total amount of active protein encoded by the respective test polynucleotide when expressed in the expression system in a predetermined period of time. In some embodiments, the expression property is an estimate of a total amount of soluble protein encoded by the respective test polynucleotide when expressed in the expression system.

In some embodiments, the sequence element in the plurality of sequence elements consists of a codon. In some embodiments, a sequence element in the plurality of sequence elements consists of a codon pair. A codon pair is a predetermined first codon and predetermined second codon that are adjacent to each other and are in the same reading frame. In some embodiments, a sequence element in the one or more sequence elements is a nucleotide triplet in the +3 reading frame (encoding the "wobble" or third base of one codon and the first two bases of the following codon).

In some embodiments, the plurality of sequence elements consists of up to five, up to ten, up to fifteen, up to twenty, up to twenty-five, or up to thirty naturally occurring codons and the frequency lookup table places no restrictions on the frequency of occurrence of a codon in a test sequence when the codon is not in the frequency lookup table.

Another aspect provides a computer-readable medium storing one or more computer programs executable by a computer, the one or more computer programs collectively comprising instructions for performing any of the methods described in this section. Another aspect provides an apparatus comprising one or more processors and a memory, coupled to the one or more processors, the memory storing one or more computer programs that individually or collectively comprise instructions for performing any of the methods disclosed in this section.

5.6.6 Use of Frequency Lookup Tables and a Global Optimization Algorithm to Design a Final Polynucleotide Another aspect of the invention provides methods for designing a final polynucleotide that encodes an amino acid sequence of a predetermined polypeptide. In some embodiments, a frequency lookup table corresponding to an expression system is obtained. The frequency lookup table comprises a plurality of sequence elements and a plurality of frequency ranges. Each frequency range in the plurality of frequency ranges is for a corresponding sequence element in the plurality of sequence elements. Each respective frequency range in the plurality of frequency ranges specifies a range of frequencies that the sequence element corresponding to the respective frequency range can occur in a polynucleotide that is to be expressed in the expression system. Each sequence element in the plurality of sequence elements is optionally associated with a frame designation in the frequency lookup table.

In some embodiments, a multivariate space is searched using a global optimization algorithm. In some embodiments, the plurality of sequence elements is five or more sequence elements, ten or more sequence elements, fifteen or more sequence elements, twenty or more sequence elements, twenty-five or more sequence elements, between five and ten sequence elements, or less than fifty sequence elements.

The multivariate space comprising a plurality of variables, each variable in the plurality of variables for quantifying a fit between (i) a frequency of occurrence in a polynucleotide of a respective sequence element in the plurality of sequence elements and (ii) the frequency range for the respective sequence element in the frequency lookup table, where the global optimization algorithm assigns a score to each respective test polynucleotide in a plurality of test polynucleotides in order to find the final model, each respective score being a quantification of the fit of the respective test polynucleotide, and each test polynucleotide in the plurality of test polynucleotides encoding the amino acid sequence of the predetermined polypeptide The final polynucleotide from the plurality of test polynucleotides is outputted as the final polynucleotide sequence to a user interface device, a tangible computer readable storage medium; or the final polynucleotide is displayed in user readable form, where the final polynucleotide is deemed to be the test polynucleotide in the plurality of test polynucleotides that has a fit that is closer to an ideal fit than any other test polynucleotide in the plurality of test polynucleotides.

In some embodiments, the plurality of sequence elements consists of up to five naturally occurring codons, of up to ten naturally occurring codons, of up to fifteen naturally occurring codons, of up to twenty naturally occurring codons, of up to twenty-five naturally occurring codons or up to thirty naturally occurring codons and the frequency lookup table places no restrictions on the frequency of occurrence of a codon in a test sequence when the codon is not in the frequency lookup table.

In some embodiments, the global optimization algorithm is a heuristic search comprising a plurality of steps where, at each step in the plurality of steps, the global optimization algorithm comprises (i) quantifying a fit for each respective test polynucleotide in a subset of the plurality of test polynucleotides and (ii) enriching the plurality of test polynucleotides by removing a portion of the subset of the plurality of test polynucleotides from the plurality of test polynucleotides based on respective scores assigned to the test polynucleotides in the subset of test polynucleotides. In some embodiments, at each step in the plurality of steps, the global optimization algorithm further comprises (iii) enriching the plurality of test polynucleotides by adding a new subset of test polynucleotides to the plurality of test polynucleotides, where each test polynucleotide in the new subset of test polynucleotides is derived from values for weights in one or more test polynucleotides already in the plurality of test polynucleotides.

In some embodiments, the global optimization algorithm is a heureistic search. Examples of heureistic searches include, but are not limited to evolutionary algorithms, swarm-based optimization algorithms, memetic algorithms, and differential evolution algorithms.

In some embodiments, the global optimization algorithm is a stochastic search. Examples of stochastic searches include, but are not limited to, simulated annealing algorithm, a directed monte-carlo sampling algorithm, a stochastic tunneling algorithm, a parallel tempering algorithm, a monte-carlo with minimization algorithm or a continuation method. See for example, Horst et al., 2000, *Introduction to Global Optimization*, Second Edition, Kluwer Academic Publishers; Neumaier, 2004, Complete Search in Continuous Global Optimization and Constraint Satisfaction, pp. 271-369 in: *Acta Numerica* 2004 (A. Iserles, ed.), Cambridge University Press; Mongeau et al., 2000, Optimization Methods & Software 13(3), pp. 203-226; Kirkpatrick et al., 1983, Science 220:671-680, Hamacher, 2006, Europhys. Lett. 74(6):944, 2006; Hamacher and Wenzel, 1999, Landscape. Phys. Rev. E, 59(1):938-941; Wenzel and Hamacher, 1999, Phys. Rev. Lett., 82(15):3003-3007; Hansmann, 1997, Chem. Phys. Lett., 281:140; Zhijun, November 1996, "The effective energy transformation scheme as a special continuation approach to global optimization with application to molecular conformation," Technical Report, Argonne National Lab., IL (United States), November 1996, each of which is hereby incorporated by reference herein in its entirety.

In some embodiments, each respective test polynucleotide in the plurality of the polynucleotides: (i) excludes a restriction site sequence at a position in the respective test polynucleotide, (ii) incorporates a restriction site sequence at a position in the respective test polynucleotide, (iii) has a target G+C content, (iv) excludes a sub-sequence, longer than an allowable length, that can be exactly repeated within either strand of the respective test polynucleotide, (v) excludes a first sub-sequence that can anneal at a greater than an allowable annealing temperature to a second sub-sequence within either strand of the respective test polynucleotide, (vi) excludes of a hairpin turn, (vii) excludes a repeat element, (viii) excludes a ribosome binding site, (ix) excludes a polyadenylation signal, (x) excludes a splice site, (xi) excludes an open reading frame in each possible reading frame in the respective test polynucleotide other than the reading frame encoding the predetermined polypeptide, (xii) excludes a polynucleotide sequence that facilitates RNA degradation, (xiii) excludes an RNA polymerase termination signal, (xiv) excludes a transcriptional promoter, (xv) excludes an immunostimulatory sequence, (xvi) incorporates an immunostimulatory sequence, (xvii) excludes an RNA methylation signal, (xviii) excludes a selenocysteine incorporation signal, (xix) excludes an RNA editing sequence, (xx) excludes an RNAi-targeted sequence, (xxi) excludes an inverted repeat within the first x nucleotides encoding the amino acid sequence in the respective test polynucleotide, where x is any value between 1 nucleotide and one hundred nucleotides, or (xxii) excludes a DNA methylation signal.

In some embodiments, the fit determined for respective test polynucleotide by the search of the mulitivariate space is further determined by (i) exclusion of restriction site sequence at a position in the respective test polynucleotide, (ii) incorporation of a restriction site sequence at a position in the respective test polynucleotide, (iii) presence of a target G+C content in the respective test polynucleotide, (iv) exclusion of a sub-sequence, longer than an allowable length, that can be exactly repeated within either strand of the respective test polynucleotide, (v) exclusion of a first sub-sequence that can anneal at a greater than an allowable annealing temperature to a second sub-sequence within either strand of the respective test polynucleotide, (vi) exclusion of a hairpin turn, (vii) exclusion of a repeat element, (viii) exclusion of a ribosome binding site, (ix) exclusion of a polyadenylation signal, (x) exclusion of a splice site, (xi) exclusion of an open reading frame in each possible reading frame in the respective test polynucleotide other than the reading frame encoding the predetermined polypeptide, (xii) exclusion of a polynucleotide sequence that facilitates RNA degradation, (xiii) exclusion of an RNA polymerase termination signal, (xiv) exclusion of a transcriptional promoter, (xv) exclusion of an immunostimulatory sequence, (xvi) incorporates an immunostimulatory sequence, (xvii) exclusion of an RNA methylation signal, (xviii) exclusion of a selenocysteine incorporation signal, (xix) exclusion of an RNA editing sequence, (xx) exclusion of an RNAi-targeted sequence, (xxi) exclusion of an inverted repeat within the first x nucleotides encoding the amino acid sequence in the respective test polynucleotide, where x is between 1 nucleotide and 100 nucleotides, or (xxii) exclusion of a DNA methylation signal.

In some embodiments, the frequency lookup table further comprises a model that computes an estimated expression property value for an expression property of the predetermined polypeptide as a function of a nucleotide sequence of a test polynucleotide, and the fit determined for a respective test polynucleotide in the search of the multivariate space is further determined by the estimated expression property value for the predetermined polypeptide calculated by the model based on a nucleotide sequence of the respective test polynucleotide. In some embodiments, the expression property is an estimate of a total amount of protein encoded by the respective test polynucleotide when expressed in the expression system. In some embodiments, the expression property is an estimate of a total amount of active protein encoded by the respective test polynucleotide when expressed in the expression system. In some embodiments, the expression property is an estimate of a total amount of soluble protein encoded by the respective polynucleotide when expressed in the expression system.

In some embodiments, the sequence element in the plurality of sequence elements consists of a codon. In some embodiments, a sequence element in the plurality of sequence elements consists of a codon pair. A codon pair is a predetermined first codon and predetermined second codon that are adjacent to each other and are in the same reading frame. In some embodiments, a sequence element in the one or more sequence elements is a nucleotide triplet in the +3 reading frame (encoding the "wobble" or third base of one codon and the first two bases of the following codon).

In some embodiments, the plurality of sequence elements consists of up to five, up to ten, up to fifteen, up to twenty, up to twenty-five, or up to thirty naturally occurring codons and the frequency lookup table places no restrictions on the frequency of occurrence of a codon in a test sequence when the codon is not in the frequency lookup table.

Another aspect provides a computer-readable medium storing one or more computer programs executable by a computer, the one or more computer programs collectively comprising instructions for performing any of the methods described in this section. Another aspect provides an apparatus comprising one or more processors and a memory, coupled to the one or more processors, the memory storing one or more computer programs that individually or collectively comprise instructions for performing any of the methods disclosed in this section.

5.6.7 Use of Frequency Lookup Tables to Design a Polynucleotide Sequence

Another aspect of the present invention provides methods for designing a polynucleotide sequence that encodes a polypeptide sequence of a predetermined polypeptide. A frequency lookup table corresponding to an expression system is obtained. The frequency lookup table comprises a plurality of sequence elements and a plurality of frequency ranges. Each frequency range in the plurality of frequency ranges is for a corresponding sequence element in the plurality of sequence elements. Each respective frequency range in the plurality of frequency ranges specifies a range of frequencies with which the sequence element corresponding to the respective frequency range can occur in a polynucleotide that is to be expressed in the expression system. Each respective sequence element in the plurality of sequence elements optionally includes a frame designation which defines the frame of the respective sequence element relative to the reading frame of said predetermined polypeptide.

The polynucleotide sequence is defined using the frequency lookup table, where the defining comprises, for each respective sequence element in the frequency lookup table, (i) determining whether the respective sequence element encodes a portion of the polypeptide sequence in the frame designation specified for the respective sequence element when there is a frame designation for the respective sequence element in the frequency lookup table and (ii) determining whether the respective sequence element encodes a portion of the polypeptide sequence in any frame when there is no a frame designation for the respective sequence element in the frequency lookup table. When the respective sequence element encodes a portion of the polypeptide sequence, the sequence element is incorporated into the polynucleotide at a frequency of occurrence that is within the frequency range specified for the respective sequence element in the frequency lookup table. The polynucleotide sequence is then outputted to a user interface device, a tangible computer readable storage medium or the polynucleotide sequence is displayed in user readable form.

In some embodiments, the portion of the polypeptide sequence is a first amino acid that appears at a plurality of positions in the polypeptide sequence, a sequence element in the frequency lookup table consists of a codon that encodes the first amino acid, and the defining comprises incorporating the codon for the amino acid in the polynucleotide at a first frequency of occurrence at positions in the polynucleotide that encode the amino acid at the plurality of positions in the polypeptide sequence, where the first frequency of occurrence is within the frequency range specified for the sequence element in the frequency lookup table. For example, consider the case where the first amino acid is leucine and leucine appears at twenty positions in the polypeptide sequence. Further consider that the frequency lookup table contains a sequence element that is the codon UUA for leucine in *Homo sapiens* and a corresponding frequency range that for the leucine that specifies that the codon is to be incorporated in a frequency range of 0.30 to 0.90 relative to the five other codons that are synonymous for leucine in *homo sapiens* (UUG, CUU, CUC, CUA, and CUG). This means that across the twenty positions in the polypeptide sequence, the codon UUA is to be used between thirty percent (at six leucine positions) to ninety percent (at eighteen leucine positions) and the codons (UUG, CUU, CUC, CUA, and CUG) are to be used in the remaining positions.

In some embodiments, the portion of the polypeptide sequence in the frame designation specified for the respective sequence element is an amino acid pair that appears at a plurality of positions in the polypeptide sequence, a sequence element in the frequency lookup table consists of a codon pair that encodes the first amino acid pair, and the defining comprises incorporating the codon pair encoding the amino acid pair in the polynucleotide at a first frequency of occurrence at positions in the polynucleotide that encode the amino acid pair at the plurality of positions in the polypeptide sequence, where the first frequency of occurrence is within the frequency range specified for the sequence element in the frequency lookup table.

In some embodiments, the frequency lookup table further comprises a frequency modification function for a predetermined sequence element, and the defining further comprises using the frequency modification function to adjust, by an amount, the frequency range for the predetermined sequence element where the frequency modification function is determined by the frequency of occurrence, within the predetermined polypeptide sequence, of the portion of the polypeptide sequence encoded by the respective sequence element. Such a frequency modification function is useful to provide tiered frequency ranges as a function of the number of times a sequence element appears within the predetermined polypeptide sequence. For example, if the sequence element appears less than a threshold number of times in the predetermined polypeptide sequence the frequency lookup table imposes a first frequency lookup table and if the sequence element appears at or more than a threshold number of times in the predetermined polypeptide sequence, the frequency lookup table imposes a second frequency lookup table. Exemplary values for the threshold is any value between two and one thousand. In another embodiment, the frequency modification function operates on the maximum and/or the minimum of the frequency range for a predetermine sequence element based on a number of times the predetermined sequence element appears in the predetermined polypeptide sequence. For example, the minimum of the frequency range can be a frequency that is divided by the number of times the predetermined sequence element appears in the predetermined polypeptide sequence, and so forth. In some embodiments, the portion of the polypeptide sequence encoded by the respective sequence element is a predetermined amino acid. In some embodiments, the sequence element comprises the wobble nucleotide of a first codon and the first two nucleotides of a of a second codon, where the first and second codon respectively encode a first amino acid and a second amino acid in a pair of adjacent amino acids in the polypeptide sequence, where the first codon is the 5' codon and the second codon is the 3' codon in the pair of adjacent codons.

In some embodiments, the defining the polynucleotide sequence further comprises (i) exclusion of a restriction site sequence in the polynucleotide sequence, (ii) incorporation of a restriction site sequence in the polynucleotide sequence, (iii) a designation of a target G+C content in the polynucleotide sequence, (iv) exclusion of a sub-sequence, longer than an allowable length, that can be exactly repeated within either strand of the polynucleotide sequence, (v) exclusion of a first sub-sequence that can anneal at a greater than an allowable annealing temperature to a second sub-sequence within either strand of the polynucleotide sequence, (vi) exclusion of a hairpin turn in the polynucleotide sequence, (vii) exclusion of a repeat element in the polynucleotide sequence, (viii) exclusion of a ribosome binding site in the polynucleotide sequence, (ix) exclusion of a polyadenylation signal in the polynucleotide sequence, (x) exclusion of a splice site in the polynucleotide sequence, (xi) exclusion of an open reading frame in each possible reading frame in the test polynucleotide other than a reading frame encoding the polypeptide sequence, (xii) exclusion of a polynucleotide sequence that facilitates RNA degradation in the polynucleotide sequence, (xiii) exclusion of an RNA polymerase termination signal in the polynucleotide sequence, (xiv) exclusion of a transcriptional promoter in the polynucleotide sequence, (xv) exclusion of an immunostimulatory sequence in the polynucleotide sequence, (xvi) incorporation of an immunostimulatory sequence in the polynucleotide sequence, (xvii) exclusion of an RNA methylation signal in the polynucleotide sequence, (xviii) exclusion of a selenocysteine incorporation signal in the polynucleotide sequence, (xix) exclusion of an RNA editing sequence in the polynucleotide sequence, (xx) exclusion of an RNAi-targeted sequence in the polynucleotide sequence, (xxi) exclusion of an inverted repeat within the first x nucleotides encoding the amino acid sequence in the polynucleotide sequence, where x is any number between one nucleotide and one hundred nucleotides, and/or (xxii) exclusion of a DNA methylation signal in the polynucleotide sequence.

In some embodiments, the plurality of sequence elements comprises a plurality of codons, where the plurality of codons comprises all of the natural codons encoding at least one amino acid, and where each frequency range for a codon in the plurality of codons comprises: a maximum percent occurrence of the corresponding codon relative to the occurrence of all other codons that code the amino acid corresponding to the corresponding codon throughout the polynucleotide sequence; and a minimum percent occurrence of the corresponding codon relative to the occurrence of all other codons that code the amino acid corresponding to the corresponding codon throughout the polynucleotide sequence, wherein the minimum percent occurrence of at least one codon in the plurality of codons is greater than zero percent and less than one hundred percent.

In some embodiments, the polypeptide sequence consists of each of a plurality of positions in the polypeptide sequence that contain the same predetermined amino acid. In some embodiments, a sequence element in the plurality of sequence elements comprises a predetermined homopolymer stretch and a transcription pause site within a predetermined number of nucleotides of each other.

Another embodiment provides a method of designing a polynucleotide sequence that encodes a polypeptide sequence of a predetermined polypeptide. The method comprises obtaining a first frequency lookup table corresponding to an expression system, where the first frequency lookup table comprises a plurality of sequence elements and a first plurality of frequency ranges, each frequency range in the first plurality of frequency ranges is for a corresponding sequence element in the plurality of sequence elements, each respective frequency range in the first plurality of frequency ranges specifies a range of frequencies with which the sequence element corresponding to the respective frequency range can occur in the polynucleotide sequence and each respective sequence element in the plurality of sequence elements optionally includes a frame designation which defines the frame of the respective sequence element relative to the reading frame of said predetermined polypeptide.

The method further comprises obtaining a second frequency lookup table corresponding to the expression system, where the second frequency lookup table comprises the plurality of sequence elements and a second plurality of frequency ranges, each frequency range in the second plurality of frequency ranges is for a corresponding sequence element in the plurality of sequence elements, each respective frequency range in the second plurality of frequency ranges specifies a range of frequencies with which the sequence element corresponding to the respective frequency range can occur in the predetermined polypeptide, and each respective sequence element in the second plurality of sequence elements optionally includes a frame designation which defines the frame of the respective sequence element relative to the reading frame of said predetermined polypeptide.

The polynucleotide sequence is defined. This defining comprises, for each respective sequence element in the plurality of sequence elements, determining a number of times an amino acid encoded by the sequence element is present in the polypeptide, where, when the number of times is more than a threshold amount the sequence element is incorporated into the polynucleotide at a frequency of occurrence that is within the frequency range specified for the respective sequence element in the first frequency lookup table. When the number of times is equal to or less than the threshold amount, the sequence element is incorporated into the polynucleotide at a frequency of occurrence that is within the frequency range specified for the respective sequence element in the second frequency lookup table. The polynucleotide sequence is then outputted to a user interface device, a tangible computer readable storage medium. Or the polynucleotide sequence is displayed in user readable form.

Another aspect provides a method of designing a polynucleotide sequence that encodes a polypeptide sequence of a predetermined polypeptide. The method comprises obtaining a first frequency lookup table corresponding to an expression system. The first frequency lookup table comprises a plurality of sequence elements and a first plurality of frequency ranges. Each frequency range in the first plurality of frequency ranges is for a corresponding sequence element in the plurality of sequence elements. Each respective frequency range in the first plurality of frequency ranges specifies a range of frequencies with which the sequence element corresponding to the respective frequency range can occur in the polynucleotide sequence. Each respective sequence element in the plurality of sequence elements optionally includes a frame designation which defines the frame of the respective sequence element relative to the reading frame of said predetermined polypeptide. A second frequency lookup table corresponding to the expression system is obtained. The second frequency lookup table comprises the plurality of sequence elements and a second plurality of frequency ranges. Each frequency range in the second plurality of frequency ranges is for a corresponding sequence element in the plurality of sequence element. Each respective frequency range in the second plurality of frequency ranges specifies a range of frequencies with which the sequence element corresponding to the respective frequency range can occur in said predetermined polypeptide. Each respective sequence element in the second plurality of sequence elements optionally includes a frame designation which defines the frame of the respective sequence element relative to the reading frame of said predetermined polypeptide. The polynucleotide sequence is defined. This defining comprises, for each respective sequence element in the plurality of sequence elements, determining a frequency with which an amino acid encodable by the sequence element is present in the polypeptide relative to the total number of amino acids in the polypeptide where, when the frequency is more than a threshold amount the sequence element is incorporated into the polynucleotide at a frequency of occurrence that is within the frequency range specified for the respective sequence element in the first frequency lookup table, and when the frequency is equal to or less than the threshold amount, the sequence element is incorporated into the polynucleotide at a frequency of occurrence that is within the frequency range specified for the respective sequence element in the second frequency lookup table. The polynucleotide sequence is outputted to a user interface device, a tangible computer readable storage medium. Alternatively, the polynucleotide sequence is displayed in user readable form.

Another aspect provides a method of designing a polynucleotide sequence that encodes a polypeptide sequence of a predetermined polypeptide. The method comprises obtaining a plurality of frequency lookup tables (e.g., two or more frequency lookup tables, three or more frequency lookup tables, four or more frequency lookup tables, five or more frequency lookup tables, or between two and twenty frequency lookup tables, etc.) each frequency lookup table in the plurality of frequency lookup tables corresponding to the same expression system, where each respective frequency lookup table in the plurality of frequency lookup tables comprises: (i) a plurality of sequence elements and a plurality of frequency ranges, (ii) each frequency range in the plurality of frequency ranges is for a corresponding sequence element in the plurality of sequence elements, (iii) each respective frequency range in the plurality of frequency ranges specifies a range of frequencies with which the sequence element corresponding to the respective frequency range can occur in the polynucleotide sequence, (iv) each respective sequence element in the plurality of sequence elements optionally includes a frame designation which defines the frame of the respective sequence element relative to the reading frame of said predetermined polypeptide; and (v) a unique frequency lookup table condition criterion. In the method, the polynucleotide sequence is defined. The defining comprises, for each respective sequence element in the plurality of sequence elements, determining a frequency lookup table condition for the respective sequence element in the polynucleotide sequence, where, when the frequency lookup table condition satisfies a unique frequency lookup table condition criterion for a corresponding frequency lookup table in the plurality of frequency lookup tables, the sequence element is incorporated into the polynucleotide at a frequency of occurrence that is within the frequency range specified for the respective sequence element in the corresponding frequency lookup table. The method further comprises outputting the polynucleotide sequence to a user interface device, a tangible computer readable storage medium or displaying the polynucleotide sequence in user readable form. In some embodiments, the unique frequency lookup table condition criterion for the respective sequence element is a number of times an amino acid encoded by the sequence element is present in the polypeptide.

Another aspect provides a computer-readable medium storing one or more computer programs executable by a computer, the one or more computer programs collectively comprising instructions for performing any of the methods described in this section. Another aspect provides an apparatus comprising one or more processors and a memory, coupled to the one or more processors, the memory storing one or more computer programs that individually or collectively comprise instructions for performing any of the methods disclosed in this section.

5.7 RELATIVE AND ABSOLUTE CODON FREQUENCIES

In some cases, the level of protein expression, the level of soluble protein expression or the level of active protein expression obtained from a polynucleotide in an expression host may depend upon the relative frequencies with which different synonymous codons are used within the polynucleotide. This is the information that is typically encoded in a codon bias table. In some cases, the level of protein expression, the level of soluble protein expression or the level of active protein expression obtained from a polynucleotide in an expression host may depend upon the absolute frequencies with which different synonymous codons are used within the polynucleotide. This is different from the information typically encoded in a codon bias table, since it depends not only upon the polynucleotide but also upon the encoded polypeptide.

As an example to clarify this difference between codon bias or relative codon frequency and absolute codon frequency, consider a polypeptide containing 100 amino acids of which 20 are Tyr. This polypeptide could be encoded by a polynucleotide that used the TAT codon 7 times (i.e. 35% of 20) and the TAC codon 13 times (i.e. 65% of 20). Then consider a second polypeptide containing 100 amino acids of which 40 are Tyr. This second polypeptide could be encoded by a second polynucleotide that used the TAT codon 14 times (i.e. 35% of 40) and the TAC codon 26 times (i.e. 65% of 40). Both the first and second polynucleotides have codon biases for TAT of 0.35 and for TAC of 0.65. That is the codon TAT is used to encode Tyr 35% or 0.35 of the time, and the codon TAC is used to encode Tyr 65% or 0.65 of the time. However the first polynucleotide uses TAT at an absolute frequency of 7:100 (or 0.07), that is the codon TAT occurs 7 times per hundred codons in the polynucleotide. The second polynucleotide uses TAT at an absolute frequency of 14:100 (or 0.14), because the codon TAT occurs 14 times per hundred codons in the polynucleotide. The codon bias or relative codon frequency is thus the frequency of a codon relative to all synonymous codons, while the absolute codon frequency is the frequency of a codon relative to both synonymous and non-synonymous codons, that is to the total number of codons used to encode the polypeptide in the polynucleotide.

5.8 DESIGN OF CODON FUNCTION TABLES

In some cases, the level of protein expression, the level of soluble protein expression or the level of active protein expression obtained from a polynucleotide in an expression host may depend upon the rate at which the polynucleotide is translated, which is also the rate at which the polypeptide is extended. In some embodiments of the invention, for the synthesis of some polypeptides in some expression systems this relationship may be direct: the more quickly a ribosome is able to add all of the amino acids in a polypeptide, the more polypeptides may be produced per unit of time and so the greater the expression levels of polypeptide that may be obtained. In some embodiments of the invention, for other polypeptides and other expression systems it may be an inverse relationship: the more slowly a ribosome is able to add all of the amino acids in a polypeptide, the more time the polypeptide may have to fold, and so the more soluble protein may be produced. In some embodiments of the invention it may be advantageous to design a polynucleotide that allows amino acids to be added most rapidly to the polypeptide except at certain positions, regions, or domains of the polypeptide structure where it is critical to slow translation to promote proper folding. Such positions or regions may be at or near protein structural domain boundaries or consist of multiple contiguous or non-contiguous amino acids within a structural domain where folding is sensitive to translation rate.

One factor that affects the rate of translation in some expression systems under some conditions is the rate with which each charged tRNA binds at the A site of the ribosome; this step is followed by recognition of the cognate codon bringing the aminoacyl stem of the tRNA into the A site of the ribosomal large subunit, joining of the incoming amino acid to the growing peptide chain by a peptidyl transferase activity, and translocation of the tRNA and peptide chain to the ribosome's P site. The time taken for addition of an amino acid to a growing peptide chain can thus be approximated as $$t_{ad} = t_c + t_e$$

where $t_{ad}$ is the time taken for addition of an amino acid to the peptide chain, $t_c$ is the time taken for the correct charged tRNA to bind to its codon and fully occupy the ribosome's A site, and $t_e$ is the time taken for the catalytic and translocation steps.

The time taken for a single ribosome to complete synthesis of an entire polypeptide can therefore be approximated as:

$$t_{syn} = t_{in} + \Sigma t_{ad}$$

where $t_{syn}$ is the time taken to synthesize the polypeptide, $t_{in}$ is the time taken for the ribosome to bind to the message and initiate translation.

$\Sigma t_{ad}$ is the sum of the times taken for the addition of each amino acid.

In selecting preferred codons, the rate of translational initiation may be considered independent or dependent on the polypeptide coding sequence. The degree to which initiation is dependent on the coding sequence may be influenced by the initial peptide sequence, the host organism, and the expression system employed. In systems where initiation depends primarily upon sequences to the 5' of the open reading frame, it is advantageous to simplify the problem by considering that the time taken to initiate translation is approximately constant for all possible codon sequences. In other systems it is advantageous to consider that both initiation and elongation times are dependent on codon selection, and make adjustments to sequences that may affect initiation. Such sequences may include those that promote secondary structure of the mRNA near or possibly covering the start codon and/or the ribosome binding site (RBS), and thus may hinder proper initiation. To minimize interference with initiation, a polynucleotide can be designed by choosing codons that result in an initial coding sequence that does not interfere with ribosome binding. Optimal initial sequences may be highly dependent on the sequence of the 5' UTR of the mRNA, particularly that of and near the RBS. Such designs can be performed by mRNA secondary structure prediction software to analyze RBS interference.

Ribosomes are especially susceptible to abortion of elongation in the first 15-20 codons translated. Use of rapidly translated codons in the initial coding sequence can minimize abortion as well as increasing the initiation rate by clearing the ribosome binding site faster. Preferred codons for the initial coding sequence may be identified by systematically varying the codons for the first 10, 20 or 30 amino acids while keeping the remainder of the coding sequence constant, or while varying it independently of the variation in the first 10, 20 or 30 codons. Experimental expression data can then be used to distinguish correlations between initial sequence and expression level and optimal sequences can then be determined.

To design polynucleotide sequences that will result in shorter synthesis times for an encoded polypeptide, selecting codons that result in lower values for $\Sigma t_{ad}$ may be advantageous. The speed with which the incoming amino acid is joined to the growing peptide chain by a peptidyl transferase activity and the tRNA and peptide chain are translocated to the ribosome's P site do not depend to a significant degree upon the codon used. Thus shorter times for the synthesis of a polypeptide will result from shorter times taken for a charged tRNA to bind to its codon on the mRNA and fully occupy the A site of the ribosome.

The rate at which charged tRNA binds to and is selected by the ribosome for A-site entry may depend on the concentration of charged tRNA available in the expression system. The higher the concentration the shorter the time expected for the tRNA to associate with its codon at the A-site. The overall tRNA selection rate may also depend on the rate at which tRNA dissociates from the A-site before recognition of the correct codon-anticodon pairing and selection for petidyl transfer. Multiple tRNA species may recognize a particular codon and a particular tRNA species often may recognize multiple codons. The tRNA-codon association and dissociation rates may depend on the particular tRNA species and codon involved. These rates may also be influenced by the tRNA and codon occupying the P-site of the ribosome, either by direct physical interaction of the P-site tRNA with the closely binding A-site tRNA or by influencing the presentation of the codon to be recognized. A further influence on tRNA selection may be the rate at which the ribosome recognizes the correct codon-anticodon pairing and allows entry of the tRNA to the A-site of the large ribosomal subunit for peptidyl transfer. This rate may depend on the specific tRNA species and codon involved and also may depend on the P-site tRNA and codon if these influence how the ribosome recognizes the codon-anticodon interaction.

The process by which a charged tRNA is selected by the ribosome for peptidyl transfer may be described by the following simplified expression:

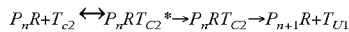

where $P_nR$ is the complex of the P-site tRNA with the mRNA programmed ribosome, $T_{C2}$ is the aminoacyl-tRNA to be selected (ternary complex of EF-Tu and the charged tRNA), $P_nRT_{C2}*$ is the initial complex of the aminoacyl-tRNA with the ribosome, $P_nRT_{C2}$ is the complex after recognition of the codon-anticodon interaction and full entry of the aminoacyl-tRNA into the ribosomal A-site, $P_{n+1}R$ is the ribosomal complex after peptidyl transfer and translocation of the A-site tRNA to the P-site, and $T_{U1}$ is the deacylated form of the initial P-site tRNA.

In selecting codons for shorter translation times, one may choose to assume that the tRNA selection rate is dependent primarily on the rate at which the cognate charged tRNA associates with the ribosome. Under this assumption the rate of selection would be highly dependent on the charged tRNA ternary complex concentration. Each tRNA exists in a full ternary complex (will be referred to simply as "charged") or in some other form inactive for peptide acceptor use by the ribosome (will be referred to as "uncharged"). The balance of tRNA species i may be expressed $$T_{Ti} = T_{Ci} + T_{Ui}$$

where $T_{Ti}$ is the total tRNA of species i, $T_{Ci}$ is the concentration of charged tRNA of species i, and $T_{Ui}$ is the concentration of uncharged tRNA of species i, The rate at which charged tRNA is consumed may be expressed

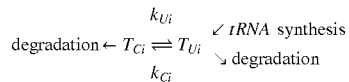

where $k_{Ui}$ is an overall rate constant for loss of charged tRNA species i, which includes consumption for protein synthesis, chemical deacylation and any other form of reversible loss of active ternary complex. The term $k_{Ci}$ is the rate constant for charging of tRNA species i. In determining the relationship of codon usage to expression rate, one simplification could be to assume that $T_{Ci}$ is in steady state during protein synthesis and that total tRNA of species i is constant. If irreversible degradation of $T_{Ci}$ is assumed to be insignificant, then the steady-state assumptions yield the relationship:

$$T_{Ci} = k_{Ci} T_{Ui} / k_{Ui}$$

And substituting $T_{Ui}$ with $(T_{Ti} - T_{Ci})$ $$T_{Ci} = \frac{T_{Ti} k_{Ci}}{k_{Ui} + k_{Ci}}$$

The overall rate constant of uncharging may be considered the sum of the constants for consumption by protein synthesis, $k_{Pi}$, and all other reversible degradation, $k_{Di}$:

$$k_{Ui} = k_{pi} + k_{Di}$$

If consumption for protein synthesis is considered the dominant path of charged tRNA loss, the expression for charged tRNA level may be simplified to:

$$T_{Ci} = \frac{T_{Ti} k_{Ci}}{k_{Pi} + k_{Ci}}$$

The first order rate constant for consumption of tRNA species i in protein synthesis can be expressed as the product of the concentration of a cognate codon j at the ribosomal A-site, $C_j$, times the rate constant for reaction with that codon, $k_{Sj}$, summed for all codons read by that tRNA:

$$k_{pi} = \Sigma k_{Sj} C_j$$

Thus, charged tRNA may be expressed as follows:

$$T_{Ci} = \frac{T_{Ti}k_{Ci}}{\sum k_{s_j}C_j + k_{Ci}}$$

The above equation shows one way to understand charged tRNA levels as a function of codon usage. As consumption, $\Sigma k_{S_j}C_j$, becomes significant relative to charging, $k_{Ci}$, the level of charged tRNA is lowered, potentially lowering the rate of protein synthesis at steps involving the lowered tRNA species. One way specific tRNA consumption may be increased is by increasing the frequency usage of codons read by the tRNA, raising $C_j$.

One way the translation rate of a particular codon $v_{Cj}$ read by tRNA species i may be modeled is the product of the charged tRNA concentration and the reaction rate constant for the codon, summed for all tRNA species—codon combinations for that codon:

$$v_{Cj} = \Sigma T_{Ci} k_{Sj}$$

The complete relationship may be considerably more complicated due to competition between tRNAs for the ribosomal A-site and other factors, although the above approximation may be sufficient for practical modeling of the relationship between codon usage and expression level. In this relationship it can be seen that codon translation rate is increased by higher steady-state charged tRNA level and by a higher rate constant for translation of the codon. In choosing codons to maximize expression, one approach according to the above discussion would be to use codons that are read at a high rate, but use a balance of codons read by different tRNAs such that specific tRNA consumption remains low relative to recharging and $T_{Ci}$ remains high as possible. This balance will depend upon the frequency of each amino acid within the polypeptide. For example in a polynucleotide encoding a polypeptide with many leucine residues but few serine residues it will be important to balance the codons for leucine but less important to balance the codons for serine. Similarly it will generally be more important to balance the codons for other highly represented amino acids within an encoded polypeptide than those that occur infrequently within the polypeptide. Thus in some embodiments it is advantageous to use different codon bias table or lookup tables or design algorithms may be used for designing polynucleotides to encode different polypeptides.

Context of the codon in the mRNA, such as the nature of the preceding codon, the position within the open reading frame, or surrounding structure in the mRNA, may alter the rate of reaction of a tRNA with a codon. In a more generalized form, therefore, $k_{Sj}$ would refer to the reaction rate with a cognate codon in a context j and $\Sigma k_{S_j}C_j$ would be the sum for all contexts and rates for cognate codons for the tRNA species. One way codon context may be simplified is by considering only neighboring sequence in the mRNA. For example, one may include in the context with a codon only the preceding codon (61 possible contexts for each codon after the start codon), only the preceding dinucleotide (16 possible contexts), or only the preceding nucleotide (4 possible contexts).

In determining the relationship between gene sequence and expression level, the above equations suggest alternative ways to define the parameters for system modeling. In one preferred embodiment of the invention, frequencies of individual codons may be treated as independent variables. In another preferred embodiment, relationships between codon usage and tRNA concentration are used, as exemplified above, to determine expression models that may more accurately reflect the mechanism of protein translation. In such models, expression is fit as a function of the influence of codon usage on tRNA levels and the rate constants for codon translation. For example, protein synthesis may be modeled as proportional to charged tRNA levels and related to codon usage and recharging rates as described above. In another embodiment, codon context information may be added to further refine the model by accounting for any influence of context on translation rates as discussed above.

5.9 DESIGN OF POLYNUCLEOTIDES FOR IMPROVED EXPRESSION PROPERTIES OF ENCODED POLYPEPTIDES

Measuring one or more expression properties of the polynucleotides in a codon variant set produces a set of correlated values for sequence element usage and one or more expression property. Sequence element usage can then be taken directly from one of the best expressing variants. Alternatively sequence element usage can be calculated as an average value or a weighted average from a set of the best expressing variants. Alternatively sequence-expression modeling can produce single values or ranges of values for the absolute or relative frequency for each sequence element that best correlates with desired expression properties. These frequencies can be provided as a frequency lookup table or a codon frequency table or matrix, or a codon lookup table. In some embodiments, these tables or matrices provide a target value or range of values for the frequencies of codons for one or more amino acids that should be used in designing a polynucleotide to encode a polypeptide.

Frequency lookup tables can be created from sequence-expression relationships to describe a target range of relative or absolute frequencies for each sequence element instead of the single value for each codon that is found in codon bias tables that describe the frequencies of codons found in naturally occurring sequences or genomes. These frequency lookup tables can thus provide a target range for the frequency of each sequence element (e.g. codon) in a designed polynucleotide, rather than a single target value. This is particularly advantageous when the frequencies of some sequence elements have strong correlations with desired expression properties and the frequencies of other sequence elements appear to be less important.

This balance will depend upon the frequency of each amino acid within the polypeptide. For example in a polynucleotide encoding a polypeptide with many leucine residues but few serine residues it will be important to balance the codons for leucine but less important to balance the codons for serine. Similarly it will generally be more important to balance the codons for other highly represented amino acids within an encoded polypeptide than those that occur infrequently within the polypeptide. Thus different frequency lookup tables or design algorithms may be used for designing polynucleotides to encode different polypeptides.

One codon variant set can be expressed in more than one expression system, sequence-expression relationships can be derived from more than one expression system and for more than one expression property. In some embodiments, polynucleotides are designed using sequence element target frequencies expression derived from measuring expression properties of the codon variant set. It is advantageous to express these designed polynucleotides in the same expression system that was used for expression of the codon variant set, since different expression systems or conditions may differ in the factors that are rate limiting for the expression property of interest.

Another aspect of the present invention provides a computer program product for use in conjunction with a computer system, the computer program product comprising a computer readable storage medium and a computer program mechanism embedded therein. The computer program mechanism comprising instructions for carrying out any step of any method disclosed herein that does not involve expressing a protein or measuring an abundance of a protein. Still another aspect of the invention provides a computer system comprising a central processing unit and a memory, coupled to the central processing unit, the memory storing the aforementioned computer program product.

5.10 ADDITIONAL EMBODIMENTS

What follows are additional exemplary embodiments.

Embodiment 1

A method of designing a final polynucleotide that encodes an amino acid sequence of a predetermined polypeptide, the method comprising: (A) obtaining a frequency lookup table corresponding to an expression system, wherein (i) the frequency lookup table comprises a plurality of sequence elements and a plurality of frequency ranges, (ii) each frequency range in the plurality of frequency ranges is for a corresponding sequence element in the plurality of sequence elements, (iii) each respective frequency range in the plurality of frequency ranges specifies a range of frequencies that the sequence element corresponding to the respective frequency range can occur in a polynucleotide that is to be expressed in the expression system, and (iv) each sequence element in the plurality of sequence elements is optionally associated with a frame designation in the frequency lookup table; (B) defining a test polynucleotide that encodes the amino acid sequence; (C) determining a score for the test polynucleotide using the frequency lookup table, wherein the score determined for the test polynucleotide is collectively determined by a plurality of agreement scores, each agreement score in the plurality of agreement scores being a measure of agreement between (i) an actual sequence element frequency of a respective sequence element in the plurality of sequence elements in the test polynucleotide and (ii) a frequency range specified for the respective sequence element in the frequency lookup table; (D) processing the test polynucleotide, wherein the processing comprises: accepting the test polynucleotide from the last instance of the determining (C) when (i) the test polynucleotide has a score that is closer to a predetermined ideal score than any other score assigned to a test polynucleotide in a prior instance of the assigning (C), or (ii) there is no prior instance of the determining (C), and rejecting the test polynucleotide from the last instance of the determining (C) when a test polynucleotide in an instance of the determining (C) computed before the last instance of the determining (C) has a score that is closer to an ideal score than the score assigned to the test polynucleotide in the last instance of the determining (C); (E) repeating (B) through (D) until an exit condition is achieved, wherein the test polynucleotide to be accepted by the last instance of the processing (D) before the exit condition is achieved is deemed to be the final polynucleotide; and (F) outputting the final polynucleotide to a user interface device, a tangible computer readable storage medium; or displaying the final polynucleotide in user readable form.

Embodiment 2

The method of embodiment 1, wherein the exit condition is the repetition of (B) through (D) a predetermined number of times.

Embodiment 3

The method of embodiment 1, wherein the exit condition is the repetition of (B) through (D) until a score for a test polynucleotide computed in an instance of the determining (C) is within a predetermined threshold of an ideal score.

Embodiment 4

The method of embodiment 1, wherein the defining (B) further comprises: (i) exclusion of a restriction site sequence in the test polynucleotide; (ii) incorporation of a restriction site sequence in the test polynucleotide; (iii) a designation of a target G+C content in the test polynucleotide; (iv) exclusion of a sub-sequence, longer than an allowable length, that can be exactly repeated within either strand of the test polynucleotide; (v) exclusion of a first sub-sequence that can anneal at a greater than an allowable annealing temperature to a second sub-sequence within either strand of the test polynucleotide; (vi) exclusion of a hairpin turn in the test polynucleotide; (vii) exclusion of a repeat element in the test polynucleotide; (viii) exclusion of a ribosome binding site in the test polynucleotide; (ix) exclusion of a polyadenylation signal in the test polynucleotide; (x) exclusion of a splice site in the test polynucleotide; (xi) exclusion of an open reading frame in each possible reading frame in the test polynucleotide other than a reading frame encoding the amino acid sequence; (xii) exclusion of a polynucleotide sequence that facilitates RNA degradation in the test polynucleotide; (xiii) exclusion of an RNA polymerase termination signal in the test polynucleotide; (xiv) exclusion of a transcriptional promoter in the test polynucleotide; (xv) exclusion of an immunostimulatory sequence in the test polynucleotide; (xvi) incorporation of an immunostimulatory sequence in the test polynucleotide; (xvii) exclusion of an RNA methylation signal in the test polynucleotide; (xviii) exclusion of a selenocysteine incorporation signal in the test polynucleotide; (xix) exclusion of an RNA editing sequence in the test polynucleotide; (xx) exclusion of an RNAi-targeted sequence in the test polynucleotide; (xxi) exclusion of an inverted repeat within the first x nucleotides encoding the amino acid sequence in the test polynucleotide, where x is any number between one nucleotide and one hundred nucleotides; or (xxii) exclusion of a DNA methylation signal in the test polynucleotide.

Embodiment 5

The method of embodiment 1, wherein the score determined for a test polynucleotide in an instance of the determining (C) is further determined by (i) exclusion of a restriction site sequence in the test polynucleotide; (ii) incorporation of a restriction site sequence in the test polynucleotide; (iii) a designation of a target G+C content in the test polynucleotide; (iv) exclusion of a sub-sequence, longer than an allowable length, that can be exactly repeated within either strand of the test polynucleotide; (v) exclusion of a first sub-sequence that can anneal at a greater than an allowable annealing temperature to a second sub-sequence within either strand of the test polynucleotide; (vi) exclusion of a hairpin turn in the test polynucleotide; (vii) exclusion of a repeat element in the test polynucleotide; (viii) exclusion of a ribosome binding site in the test polynucleotide; (ix) exclusion of a polyadenylation signal in the test polynucleotide; (x) exclusion of a splice site in the test polynucleotide; (xi) exclusion of an open reading frame in each possible reading frame in the test polynucleotide other than a reading frame encoding the amino acid sequence; (xii) exclusion of a polynucleotide sequence that facilitates RNA degradation in the test polynucleotide; (xiii) exclusion of an RNA polymerase termination signal in the test polynucleotide; (xiv) exclusion of a transcriptional promoter in the test polynucleotide; (xv) exclusion of an immunostimulatory sequence in the test polynucleotide; (xvi) incorporation of an immunostimulatory sequence in the test polynucleotide; (xvii) exclusion of an RNA methylation signal in the test polynucleotide; (xviii) exclusion of a selenocysteine incorporation signal in the test polynucleotide; (xix) exclusion of an RNA editing sequence in the test polynucleotide; (xx) exclusion of an RNAi-targeted sequence in the test polynucleotide; (xxi) exclusion of an inverted repeat within the first x nucleotides encoding the amino acid sequence in the test polynucleotide, where x is any number between one nucleotide and one hundred nucleotides; or (xxii) exclusion of a DNA methylation signal in the test polynucleotide.

Embodiment 6

The method of embodiment 1, wherein the frequency lookup table further comprises a model that computes an estimated expression property value for an expression property of the predetermined polypeptide as a function of a sequence of a test polynucleotide for the expression system, and wherein the score determined for a respective test polynucleotide in an instance of the determining (C) is further determined by the estimated expression property value for the predetermined polypeptide calculated by the model based on a nucleotide sequence of the respective test polynucleotide.

Embodiment 7

The method of embodiment 6, wherein the expression property is an estimate of a total amount of protein encoded by the respective test polynucleotide when expressed in the expression system in a predetermined period of time.

Embodiment 8

The method of embodiment 6, wherein the expression property is an estimate of a total amount of active protein encoded by the respective test polynucleotide when expressed in the expression system in a predetermined period of time.

Embodiment 9

The method of embodiment 6, wherein the expression property is an estimate of a total amount of soluble protein encoded by the respective test polynucleotide when expressed in the expression system in a predetermined period of time.

Embodiment 10

The method of embodiment 1, wherein a sequence element in the plurality of sequence elements consists of a codon.

Embodiment 11

The method of embodiment 1, wherein a sequence element in the plurality of sequence elements consists of a codon pair.

Embodiment 12

The method of embodiment 1, wherein the plurality of sequence elements consists of up to thirty naturally occurring codons and wherein the frequency lookup table places no restrictions on the frequency of occurrence of a codon in a test sequence when the codon is not in the frequency lookup table.

Embodiment 13

The method of embodiment 1, wherein the plurality of sequence elements consists of up to twenty naturally occurring codons and wherein the frequency lookup table places no restrictions on the frequency of occurrence of a codon in a test sequence when the codon is not in the frequency lookup table.

Embodiment 14

A computer-readable medium storing one or more computer programs executable by a computer, the one or more computer programs collectively comprising instructions for performing the method of 1.

Embodiment 15

An apparatus comprising: one or more processors; and a memory, coupled to the one or more processors, the memory storing one or more computer programs that individually or collectively comprise instructions for performing the method of embodiment 1.

Embodiment 16

A method of designing a final polynucleotide that encodes an amino acid sequence of a predetermined polypeptide, the method comprising: (A) obtaining a frequency lookup table corresponding to an expression system, wherein (i) the frequency lookup table comprises a plurality of sequence elements and a plurality of frequency ranges, (ii) each frequency range in the plurality of frequency ranges is for a corresponding sequence element in the plurality of sequence elements, (iii) each respective frequency range in the plurality of frequency ranges specifies a range of frequencies that the sequence element corresponding to the respective frequency range can occur in a polynucleotide that is to be expressed in the expression system, and (iv) each sequence element in the plurality of sequence elements is optionally associated with a frame designation in the frequency lookup table; (B) defining a set of test polynucleotides, wherein each test polynucletide in the set of test polynucleotides encodes the amino acid sequence; (C) determining a fit of each test polynucleotide in the set of test polynucleotides, wherein the fit of a respective test polynucleotide in the set of test polynucleotides is determined by a combination of a plurality of agreement scores, each agreement score in the plurality of agreement scores being a measure of agreement between (i) an actual sequence element frequency of a respective sequence element in the plurality of sequence elements in the respective test polynucleotide sequence and (ii) a frequency range specified for the respective sequence element in the frequency lookup table; (D) determining whether an exit condition has been satisfied; (E) enriching, when the exit condition has not been satisfied, the set of test polynucleotides by removing a portion of the polynucleotides from the set of test polynucleotides based on a respective fit determined for each test polynucleotide in the set of test polynucleotides; (F) enriching, when the exit condition has not been satisfied, the set of test polynucleotides by adding a subset of test polynucleotides to the set of test polynucleotides, wherein each test polynucleotide in the subset of test polynucleotides is derived from one or more test polynucleotides already in the set of test polynucleotides and wherein each test polynucleotide in the subset of test polynucleotides encodes the amino acid sequence of the predetermined polypeptide; (G) repeating (C) through (F) until an exit condition has been satisfied in an instance of the determining (D); and (F) outputting a final polynucleotide from the set of test polynucleotides as the final polynucleotide sequence to a user interface device, a tangible computer readable storage medium; or displaying the final polynucleotide in user readable form.

Embodiment 17

The method of embodiment 16, wherein the final polynucleotide is a test polynucleotide in the set of test polynucleotides that has a fit that is closer to an ideal fit than any other test polynucleotide in the set of test polynucleotides.

Embodiment 18

The method of embodiment 16, wherein the exit condition is the repetition of (C) through (F) a predetermined number of times.

Embodiment 19

The method of embodiment 1, wherein the exit condition is the repetition of (C) through (F) until a fit of a test polynucleotide computed in an instance of the determining (C) is within a predetermined threshold of an ideal score.

Embodiment 20

The method of embodiment 16, wherein the defining (B) further comprises: (i) exclusion of a restriction site sequence in a test polynucleotide in the set of test polynucleotides; (ii) incorporation of a restriction site sequence in a test polynucleotide in the set of test polynucleotides; (iii) a designation of a target G+C content in a test polynucleotide in the set of test polynucleotides; (iv) exclusion of a sub-sequence, longer than an allowable length, that can be exactly repeated within either strand of a test polynucleotide in the set of test polynucleotides; (v) exclusion of a first sub-sequence that can anneal at a greater than an allowable annealing temperature to a second sub-sequence within either strand of a test polynucleotide in the set of test polynucleotides; (vi) exclusion of a hairpin turn in a test polynucleotide in the set of test polynucleotides; (vii) exclusion of a repeat element in a test polynucleotide in the set of test polynucleotides; (viii) exclusion of a ribosome binding site in a test polynucleotide in the set of test polynucleotides; (ix) exclusion of a polyadenylation signal in a test polynucleotide in the set of test polynucleotides; (x) exclusion of a splice site in a test polynucleotide in the set of test polynucleotides; (xi) exclusion of an open reading frame in each possible reading frame in a test polynucleotide in the set of test polynucleotides other than the reading frame encoding the predetermined polypeptide; (xii) exclusion of a polynucleotide sequence that facilitates RNA degradation in a test polynucleotide in the set of test polynucleotides; (xiii) exclusion of an RNA polymerase termination signal in a test polynucleotide in the set of test polynucleotides; (xiv) exclusion of a transcriptional promoter in a test polynucleotide in the set of test polynucleotides; (xv) exclusion of an immunostimulatory sequence in a test polynucleotide in the set of test polynucleotides; (xvi) incorporation of an immunostimulatory sequence in a test polynucleotide in the set of test polynucleotides; (xvii) exclusion of an RNA methylation signal in a test polynucleotide in the set of test polynucleotides; (xviii) exclusion of a selenocysteine incorporation signal in a test polynucleotide in the set of test polynucleotides; (xix) exclusion of an RNA editing sequence in a test polynucleotide in the set of test polynucleotides; (xx) exclusion of an RNAi-targeted sequence in a test polynucleotide in the set of test polynucleotides; (xxi) exclusion of an inverted repeat within the first 45 nucleotides encoding the amino acid sequence in a test polynucleotide in the set of test polynucleotides; or (xxii) exclusion of a DNA methylation signal in a test polynucleotide in the set of test polynucleotides.

Embodiment 21

The method of embodiment 16, wherein the fit that is determined for a test polynucleotide in an instance of the determining (C) is further determined by (i) exclusion of a restriction site sequence in a test polynucleotide in the test polynucleotide; (ii) incorporation of a restriction site sequence in the test polynucleotide; (iii) a designation of a target G+C content in the test polynucleotide; (iv) exclusion of a sub-sequence, longer than an allowable length, that can be exactly repeated within either strand of the test polynucleotide; (v) exclusion of a first sub-sequence that can anneal at a greater than an allowable annealing temperature to a second sub-sequence within either strand of the test polynucleotide; (vi) exclusion of a hairpin turn in the test polynucleotide; (vii) exclusion of a repeat element in the test polynucleotide; (viii) exclusion of a ribosome binding site in the test polynucleotide; (ix) exclusion of a polyadenylation signal in the test polynucleotide; (x) exclusion of a splice site in the test polynucleotide; (xi) exclusion of an open reading frame in each possible reading frame in the test polynucleotide in other than the reading frame encoding the predetermined polypeptide; (xii) exclusion of a polynucleotide sequence that facilitates RNA degradation in the test polynucleotide; (xiii) exclusion of an RNA polymerase termination signal in the test polynucleotide; (xiv) exclusion of a transcriptional promoter in the test polynucleotide; (xv) exclusion of an immunostimulatory sequence in the test polynucleotide; (xvi) incorporation of an immunostimulatory sequence in the test polynucleotide; (xvii) exclusion of an RNA methylation signal in the test polynucleotide; (xviii) exclusion of a selenocysteine incorporation signal in the test polynucleotide; (xix) exclusion of an RNA editing sequence in the test polynucleotide; (xx) exclusion of an RNAi-targeted sequence in the test polynucleotide; (xxi) exclusion of an inverted repeat within the first 45 nucleotides encoding the amino acid sequence in the test polynucleotide; or (xxii) exclusion of a DNA methylation signal in the test polynucleotide.

Embodiment 22

The method of embodiment 16, wherein the frequency lookup table further comprises a model that computes an estimated expression property value for an expression property of the predetermined polypeptide as a function of a nucleotide sequence of a test polynucleotide, and wherein the fit determined for a respective test polynucleotide in an instance of the determining (C) is further determined by the estimated expression property value for the predetermined polypeptide calculated by the model based on a nucleotide sequence of the respective test polynucleotide.

Embodiment 23

The method of embodiment 22, wherein the expression property is an estimate of a total amount of protein encoded by the respective test polynucleotide when expressed in the expression system in a predetermined period of time.

Embodiment 24

The method of embodiment 22, wherein the expression property is an estimate of a total amount of active protein encoded by the respective test polynucleotide when expressed in the expression system in a predetermined period of time.

Embodiment 25

The method of embodiment 22, wherein the expression property is an estimate of a total amount of soluble protein encoded by the respective test polynucleotide when expressed in the expression system.

Embodiment 26

The method of embodiment 16, wherein a sequence element in the plurality of sequence elements consists of a codon.

Embodiment 27

The method of embodiment 16, wherein a sequence element in the plurality of sequence elements consists of a codon pair.

Embodiment 28

The method of embodiment 16, wherein the plurality of sequence elements consists of up to thirty naturally occurring codons and wherein the frequency lookup table places no restrictions on the frequency of occurrence of a codon in a test polynucleotide in the set of test polynucleotides when the codon is not in the frequency lookup table.

Embodiment 29

The method of embodiment 16, wherein the plurality of sequence elements consists of up to twenty naturally occurring codons and wherein the frequency lookup table places no restrictions on the frequency of occurrence of a codon in a test polynucleotide in the set of test polynucleotides when the codon is not in the frequency lookup table.

Embodiment 30

A computer-readable medium storing one or more computer programs executable by a computer, the one or more computer programs collectively comprising instructions for performing the method of embodiment 16.

Embodiment 31

An apparatus comprising: one or more processors; and a memory, coupled to the one or more processors, the memory storing one or more computer programs that collectively comprise instructions for performing the method of embodiment 16.

Embodiment 32

A method of designing a final polynucleotide that encodes an amino acid sequence of a predetermined polypeptide, the method comprising: (A) obtaining a frequency lookup table corresponding to an expression system, wherein (i) the frequency lookup table comprises a plurality of sequence elements and a plurality of frequency ranges, (ii) each frequency range in the plurality of frequency ranges is for a corresponding sequence element in the plurality of sequence elements, (iii) each respective frequency range in the plurality of frequency ranges specifies a range of frequencies that the sequence element corresponding to the respective frequency range can occur in a polynucleotide that is to be expressed in the expression system; and (vi) each sequence element in the plurality of sequence elements is optionally associated with a frame designation in the frequency lookup table; (B) searching a multivariate space using a global optimization algorithm, the multivariate space comprising a plurality of variables, each variable in the plurality of variables for quantifying a fit between (i) a frequency of occurrence in a polynucleotide of a respective sequence element in the plurality of sequence elements and (ii) the frequency range for the respective sequence element in the frequency lookup table; wherein the global optimization algorithm assigns a score to each respective test polynucleotide in a plurality of test polynucleotides in order to find the final model, each respective score being a quantification of the fit of the respective test polynucleotide, and each test polynucleotide in the plurality of test polynucleotides encoding the amino acid sequence of the predetermined polypeptide; and (C) outputting the final polynucleotide from the plurality of test polynucleotides as the final polynucleotide sequence to a user interface device, a tangible computer readable storage medium; or displaying the final polynucleotide in user readable form, wherein the final polynucleotide is deemed to be the test polynucleotide in the plurality of test polynucleotides that has a fit that is closer to an ideal fit than any other test polynucleotide in the plurality of test polynucleotides.

Embodiment 33

The method of embodiment 32, wherein the plurality of sequence elements consists of up to twenty naturally occurring codons and wherein the frequency lookup table places no restrictions on the frequency of occurrence of a codon in a test sequence when the codon is not in the frequency lookup table.

Embodiment 34

The method of embodiment 32, wherein the global optimization algorithm is a heuristic search comprising a plurality of steps wherein, at each step in the plurality of steps, the global optimization algorithm comprises: (i) quantifying a fit for each respective test polynucleotide in a subset of the plurality of test polynucleotides; and (ii) enriching the plurality of test polynucleotides by removing a portion of the subset of the plurality of test polynucleotides from the plurality of test polynucleotides based on respective scores assigned to the test polynucleotides in the subset of test polynucleotides.

Embodiment 35

The method of embodiment 34, wherein at each step in the plurality of steps, the global optimization algorithm further comprises: (iii) enriching the plurality of test polynucleotides by adding a new subset of test polynucleotides to the plurality of test polynucleotides, wherein each test polynucleotide in the new subset of test polynucleotides is derived from values for weights in one or more test polynucleotides already in the plurality of test polynucleotides.

Embodiment 36

The method of embodiment 32, wherein the global optimization algorithm is a heureistic search.

Embodiment 37

The method of embodiment 36, wherein the heureistic search is an evolutionary algorithm, a swarm-based optimization algorithm, a memetic algorithm, or a differential evolution algorithm.

Embodiment 38

The method of embodiment 32, wherein the global optimization algorithm is a stochastic search.

Embodiment 39

The method of embodiment 38, wherein the stochastic search is a simulated annealing algorithm, a directed monte-carlo sampling algorithm, a stochastic tunneling algorithm, a parallel tempering algorithm, a monte-carlo with minimization algorithm or a continuation method.

Embodiment 40

The method of embodiment 32, wherein each respective test polynucleotide in the plurality of the polynucleotides: (i) excludes a restriction site sequence at a position in the respective test polynucleotide; (ii) incorporates a restriction site sequence at a position in the respective test polynucleotide; (iii) has a target G+C content; (iv) excludes a sub-sequence, longer than an allowable length, that can be exactly repeated within either strand of the respective test polynucleotide; (v) excludes a first sub-sequence that can anneal at a greater than an allowable annealing temperature to a second sub-sequence within either strand of the respective test polynucleotide; (vi) excludes of a hairpin turn; (vii) excludes a repeat element; (viii) excludes a ribosome binding site; (ix) excludes a polyadenylation signal; (x) excludes a splice site; (xi) excludes an open reading frame in each possible reading frame in the respective test polynucleotide other than the reading frame encoding the predetermined polypeptide; (xii) excludes a polynucleotide sequence that facilitates RNA degradation; (xiii) excludes an RNA polymerase termination signal; (xiv) excludes a transcriptional promoter; (xv) excludes an immunostimulatory sequence; (xvi) incorporates an immunostimulatory sequence; (xvii) excludes an RNA methylation signal; (xviii) excludes a selenocysteine incorporation signal; (xix) excludes an RNA editing sequence; (xx) excludes an RNAi-targeted sequence; (xxi) excludes an inverted repeat within the first 45 nucleotides encoding the amino acid sequence in the respective test polynucleotide; or (xxii) excludes a DNA methylation signal.

Embodiment 41

The method of embodiment 32, wherein the fit determined for respective test polynucleotide by the search (B) is further determined by (i) exclusion of restriction site sequence at a position in the respective test polynucleotide; (ii) incorporation of a restriction site sequence at a position in the respective test polynucleotide; (iii) presence of a target G+C content in the respective test polynucleotide; (iv) exclusion of a sub-sequence, longer than an allowable length, that can be exactly repeated within either strand of the respective test polynucleotide; (v) exclusion of a first sub-sequence that can anneal at a greater than an allowable annealing temperature to a second sub-sequence within either strand of the respective test polynucleotide; (vi) exclusion of a hairpin turn; (vii) exclusion of a repeat element; (viii) exclusion of a ribosome binding site; (ix) exclusion of a polyadenylation signal; (x) exclusion of a splice site; (xi) exclusion of an open reading frame in each possible reading frame in the respective test polynucleotide other than the reading frame encoding the predetermined polypeptide; (xii) exclusion of a polynucleotide sequence that facilitates RNA degradation; (xiii) exclusion of an RNA polymerase termination signal; (xiv) exclusion of a transcriptional promoter; (xv) exclusion of an immunostimulatory sequence; (xvi) incorporates an immunostimulatory sequence; (xvii) exclusion of an RNA methylation signal; (xviii) exclusion of a selenocysteine incorporation signal; (xix) exclusion of an RNA editing sequence; (xx) exclusion of an RNAi-targeted sequence; (xxi) exclusion of an inverted repeat within the first 45 nucleotides encoding the amino acid sequence in the respective test polynucleotide; or (xxii) exclusion of a DNA methylation signal.

Embodiment 42

The method of embodiment 32, wherein the frequency lookup table further comprises a model that computes an estimated expression property value for an expression property of the predetermined polypeptide as a function of a nucleotide sequence of a test polynucleotide, and wherein the fit determined for a respective test polynucleotide in the search (B) is further determined by the estimated expression property value for the predetermined polypeptide calculated by the model based on a nucleotide sequence of the respective test polynucleotide.

Embodiment 43

The method of embodiment 42, wherein the expression property is an estimate of a total amount of protein encoded by the respective test polynucleotide when expressed in the expression system.

Embodiment 44

The method of embodiment 42, wherein the expression property is an estimate of a total amount of active protein encoded by the respective test polynucleotide when expressed in the expression system.

Embodiment 45

The method of embodiment 42, wherein the expression property is an estimate of a total amount of soluble protein encoded by the respective polynucleotide when expressed in the expression system.

Embodiment 46

The method of embodiment 32, wherein a sequence element in the plurality of sequence elements consists of a codon.

Embodiment 47

The method of embodiment 32, wherein a sequence element in the plurality of sequence elements consists of a codon pair.

Embodiment 48

The method of embodiment 32, wherein the plurality of sequence elements consists of up to thirty naturally occurring codons and wherein the frequency lookup table places no restrictions on the frequency of occurrence of a codon in a test sequence when the codon is not in the frequency lookup table.

Embodiment 49

A computer-readable medium storing one or more computer programs executable by a computer, the one or more computer programs collectively comprising instructions for performing the method of embodiment 32.

Embodiment 50

An apparatus comprising: one or more processors; and a memory, coupled to the one or more processors, the memory storing one or more computer programs that collectively comprise instructions for performing the method of embodiment 32.

6. EXAMPLES

The following examples are set forth so as to provide those of ordinary skill in the art with a complete description of how to make and use embodiments of the present invention, and are not intended to limit the scope of what is regarded as the invention.

6.1 DESIGN, SYNTHESIS & EXPRESSION TESTING OF A CODON VARIANT SET FOR PHI129 DNA POLYMERASE

6.1.1 Phi 29 Variant Design

An expression construct for testing codon variants of the 1.7 kb gene for the DNA polymerase of the *Bacillus* sp. phage phi29 was designed to contain sequence elements required for expression in an *E. coli* host cell. To the 5' of the open reading frame were a T7 promoter and ribosome binding site (sequences provided as SEQAA), to the 3' of the phi29 open reading frame were two stop codons and a T7 terminator (sequences provided as SEQAB). SEQAA also contains other important vector sequences: an origin of replication, a gene conferring resistance to the antibiotic kanamycin, and a gene expressing the lac repressor. The sequences SEQAA and SEQAB were identical for all phi29 DNA polymerase variants tested, the only differences were in the codons selected to encode the polypeptide in the open reading frames, and all of these DNA sequences resulted in identical polypeptides.

The natural coding sequence for phi29 polymerase was obtained from GenBank and used as a template for gene design. A set of seven gene design parameters was varied between the designs. These were:

1. Codon bias. Codon bias describes the relative frequency with which synonymous codons are used to encode an amino acid. We used two codon bias tables, one calculated from all of the genes in the *E. coli* genome ('*E. coli*' table) and a second from a subset of 27 genes that are highly expressed ('*E. coli* II' table) (Gustafsson et al., 2004, "Codon bias and heterologous protein expression," Trends Biotechnol 22, 346-53, Henaut and Danchin, 1996, "Analysis and predictions from *Escherichia coli* sequences," *Escherichia coli* and *Salmonella typhimurium* Cellular and Molecular Biology 2, 2047-2066, Sharp and Li, 1987, "The codon Adaptation Index—a measure of directional synonymous codon usage bias, and its potential applications," Nucleic Acids Res 15, 1281-95). To design each gene variant encoding phi29 polymerase, we used Gene Designer software (Villalobos et al., 2006, "Gene Designer: a synthetic biology tool for constructing artificial DNA segments," BMC Bioinformatics 7, 285). For each consecutive amino acid the program chooses a codon with a probability that is proportional to its frequency in the chosen bias table. Thus the overall bias of the gene approximates that of the bias table.

2. Cutoff threshold. Several previous reports have shown that use of some rarely used codons may lower expression, particularly when these are used frequently or in tandem (Kane, 1995, "Effects of rare codon clusters on high-level expression of heterologous proteins in *Escherichia coli*," Curr Opin Biotechnol 6, 494-500, Shu et al., 2006, "Inhibition of translation by consecutive rare leucine codons in *E. coli*: absence of effect of varying mRNA stability," Gene Expr: 13, 97-106). We therefore used Gene Designer to exclude codons whose frequencies in the codon bias table are lower than a selected threshold (the cutoff threshold). We varied this threshold to test whether inclusion of codons used at intermediate frequency or occasional inclusion of rare codons have a detrimental effect. At the highest threshold settings used (25%, that is, the only codons allowed are those that are used to encode an amino acid more than 25% of the time in the genes from which that codon bias table is derived), 5-6 amino acids that could be encoded by multiple codons are restricted to a single choice. At the lowest settings (2%) only 0-6 of the rarest codons are excluded.

Figure 1A:
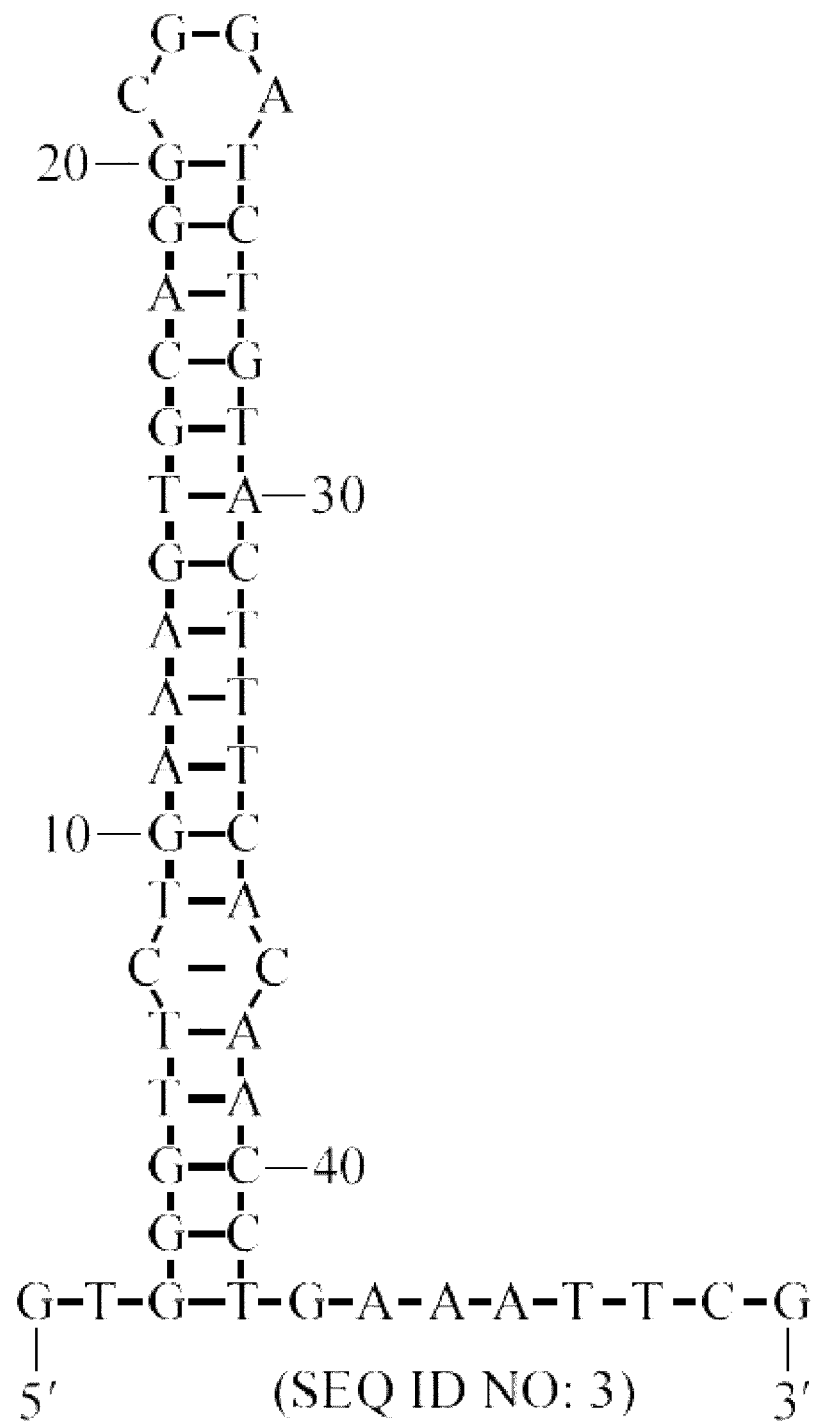
Figure 1B:
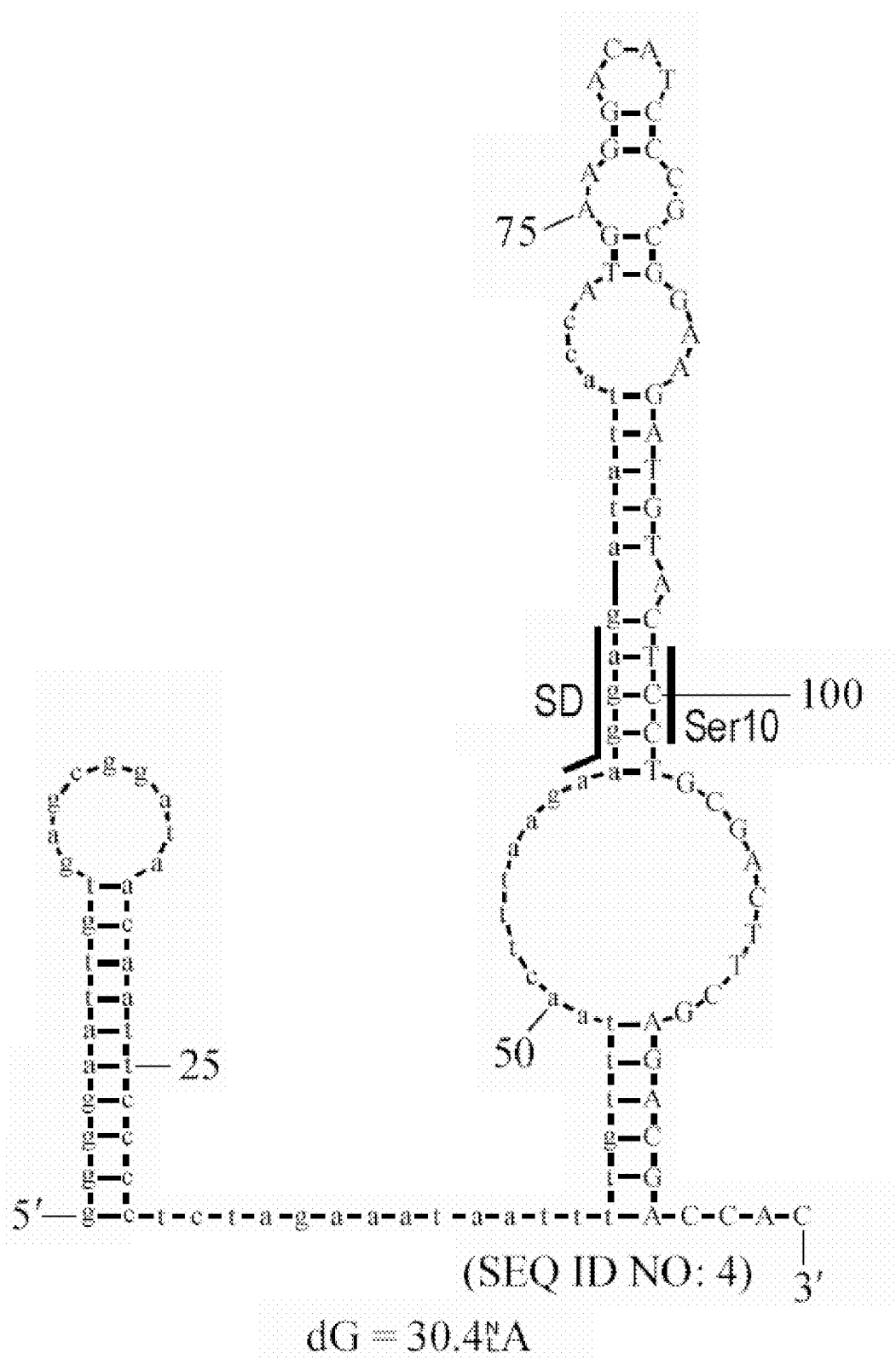

3. Internal RNA structure. After initial coding we analyzed the RNA secondary structure of each variant using UNAFold (Markham and Zuker, 2005, "DINAMelt web server for nucleic acid melting prediction," Nucleic Acids Res. 33, W577-W581). RNA structures were determined for every 50 nucleotide window of the coding sequence (1676 windows within the 1725 nucleotide open reading frame), and for the 3' terminal tail of the mRNA consisting of the last 50 nucleotides of the coding sequence through to the expected terminus. A 50 nucleotide window was used because it should identify local structures that can form between consecutive ribosomes on an mRNA: ribosome spacing is estimated at 50 nucleotides for a rapidly translating message. One region of the mRNA, the 50 nt window from position +147 to +196, was found to be especially prone to forming strong hairpin structures (FIG. 1). This structure was manually modified in selected genes by minimal codon substitutions, within the bias and threshold limits.

4. RNA structure at the 5 initiation site. We used UNAFold to calculate the RNA structure for the first 121 nucleotides from the 5' end of the mRNA to position +50 (FIG. 1). This structure was manually modified in selected genes by minimal codon substitutions, within the bias and threshold limits.

5. 5AT wobble. We manually modified the percentage of the first 15 codons that use A or T in the $3^{rd}$ position.

6. GC runs. Runs of G and/or C of 6 nucleotides or more were avoided in some sequences by defining SSSSSS (S=G or C) as a motif to avoid in Gene Designer.

7. Identity to wild type. We selected sequences with different degrees of identity to the wild type. This was performed using Gene Designer.

In addition to the codon bias table and threshold parameters systematically varied, the covariant gene codon adaptation index (CAI) (Sharp and Li, 1987, "The codon Adaptation Index—a measure of directional synonymous codon usage bias, and its potential applications," Nucleic Acids Res 15, 1281-1295), the parameter most commonly used for gene optimization, was monitored in the dataset and included in modeling. The adaptiveness of a codon is defined as its usage frequency relative to that of the most frequently used synonymous codon in the *E. coli* II bias table. The CAI for the gene is the average codon adaptiveness over all positions. A CAI of 1 means only the most frequent codon is used for all 20 amino acids at every position.

To assess the impact of these seven parameters on protein expression, each was varied within practical limits. Five parameters (codon bias, threshold, internal RNA structure, AT wobble, and GC runs), were systematically varied among variants 1-8. Two parameters, 5'-RNA and identity to wild type, were difficult to systematically vary along with the remaining set of variables, so a few genes were constructed for each where only codon bias was varied and the other parameters were not controlled. The design properties of the first 21 variants are shown in FIG. 2. On average the pairwise sequence identities of the variants was 82% and no two are more similar than 91%, except 16 and 17 (97%) and 19 and 20 (93%).

6.1.2 Phi 29 Variant Synthesis and Cloning

The gene variants were all synthesized by standard gene synthesis procedures and cloned into a pET24a expression vector between the XbaI and EcoRI restriction sites. This put each gene under transcriptional control of the strong T7 RNA polymerase promoter of this vector. Each final construct was completely sequenced in both directions to be certain that the complete sequence was as designed. The plasmid was then used to transform *E. coli* expression host strain BL21(DE3) harboring a second plasmid for low level expression of T7 lysozyme, pLysS. The background expression of T7 lysozyme, an inhibitor of T7 RNA polymerase, gives tight repression of heterologous expression prior to induction to minimize potential gene toxicity which could affect data quality.

6.1.3 Phi 29 Variant Protein Expression

Proteins were expressed from the variant genes using standard methods. Prior to analysis of the variants, expression was analyzed for multiple variants to determine appropriate expression time and temperature. Strong, consistent expression was achieved at 30° C., a commonly used temperature for heterologous expression in *E. coli*. Time courses at 30° C. showed expressed protein levels increasing to a maximum after approximately two hours, as the cells entered stationary phase growth, and remaining steady for at least five hours. Relative protein expression levels between variants were consistent throughout the time course. For our variant analysis we chose to express for four hours at 30° C.

Figure 3:
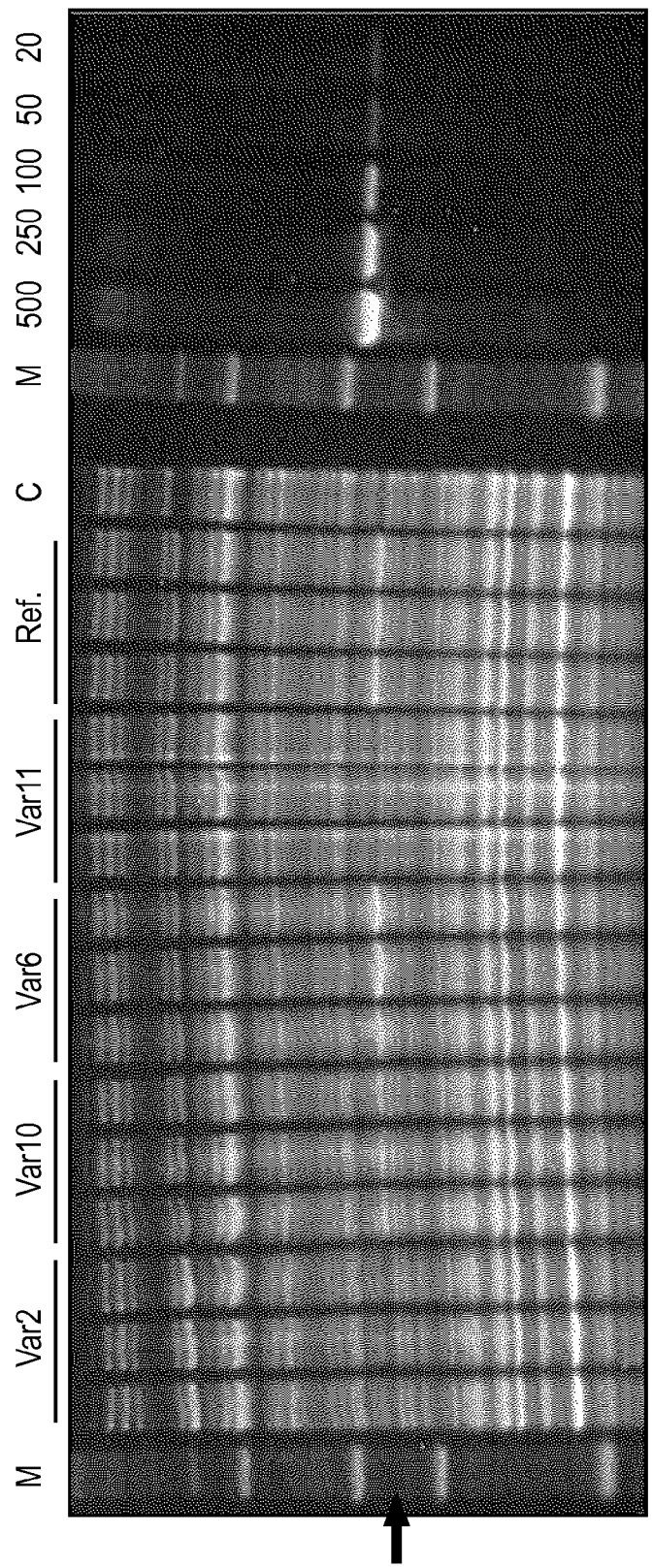

For each variant, three transformants were picked and cultured overnight in 2 ml Luria Broth (LB) containing appropriate antibiotics to maintain the expression vector and pLysS plasmid. The overnight cultures were diluted 50-fold in fresh media and incubated at 37° C. until the cells were in mid-log growth (OD at 600 nm ~0.6). Expression was induced by addition of IPTG to 1 mM and incubation for four hours at 30° C. Final optical densities of cultures were measured and equivalent amounts of culture were analyzed by polyacrylamide gel electrophoresis (a sample set of variant expression is shown in FIG. 3). Gels were stained with Sypro Ruby (Pierce), visualized by fluorescence imaging, and protein band intensities quantified using TotalLab 100 image analysis software (Nonlinear Dynamics, Inc). Each gel contained protein concentration standards to calibrate band intensity. Three replicates of a reference clone (a phi29 polymerase variant identical to variant 21 but containing two point mutations in the 5' untranslated region) were expressed in parallel cultures in each experiment to allow corrections to be made for any experiment to experiment variation. Reported expression levels are all relative to this reference. The detection limit of the assay was approximately 1 µg of phi29 polymerase per ml culture at an $A_{600}=3$. This is ~5% of the reference variant expression level. The standard error of measured expression for variant repeats was generally <20% of the mean.

Quantitation of expression levels for the first 21 variants synthesized are shown in FIG. 2. There are a wide range of expression levels among the variants, demonstrating a good sampling of expression relevant features in our gene designs. Levels ranged from below detection to 3 times the reference, a range of two orders of magnitude.

6.1.4 Analysis of Gene Design Parameters for Phi 29 Variants

To determine the influence of the various gene design parameters on expression, the data in FIG. 2 was fit to partial least squares (PLS) models using PLS Toolbox 4.0 software (Eigenvector, Inc.) within MATLAB (Mathworks, Inc). PLS regression is a highly reliable method for modeling systems data where the number of independent variables is high, approaching or even exceeding the number of samples (Eriksson et al., 2004, "Using chemometrics for navigating in the large datasets of genomics, proteomics, and metabonomics (gpm)," Anal Bioanal Chem 380, 419-29). In PLS regression, multivariate data are transformed to a variable space with reduced dimensionality that is defined by new orthogonal variables (latent variables). The latent variables are linear combinations of the original variables, calculated to maximize correlation between independent and dependent variables in as few dimensions as possible. Cross-validation methods are used to determine the optimal number of latent variables to use in the model, so that fit between data and model is maximized without over-fitting.

Figure 4A:
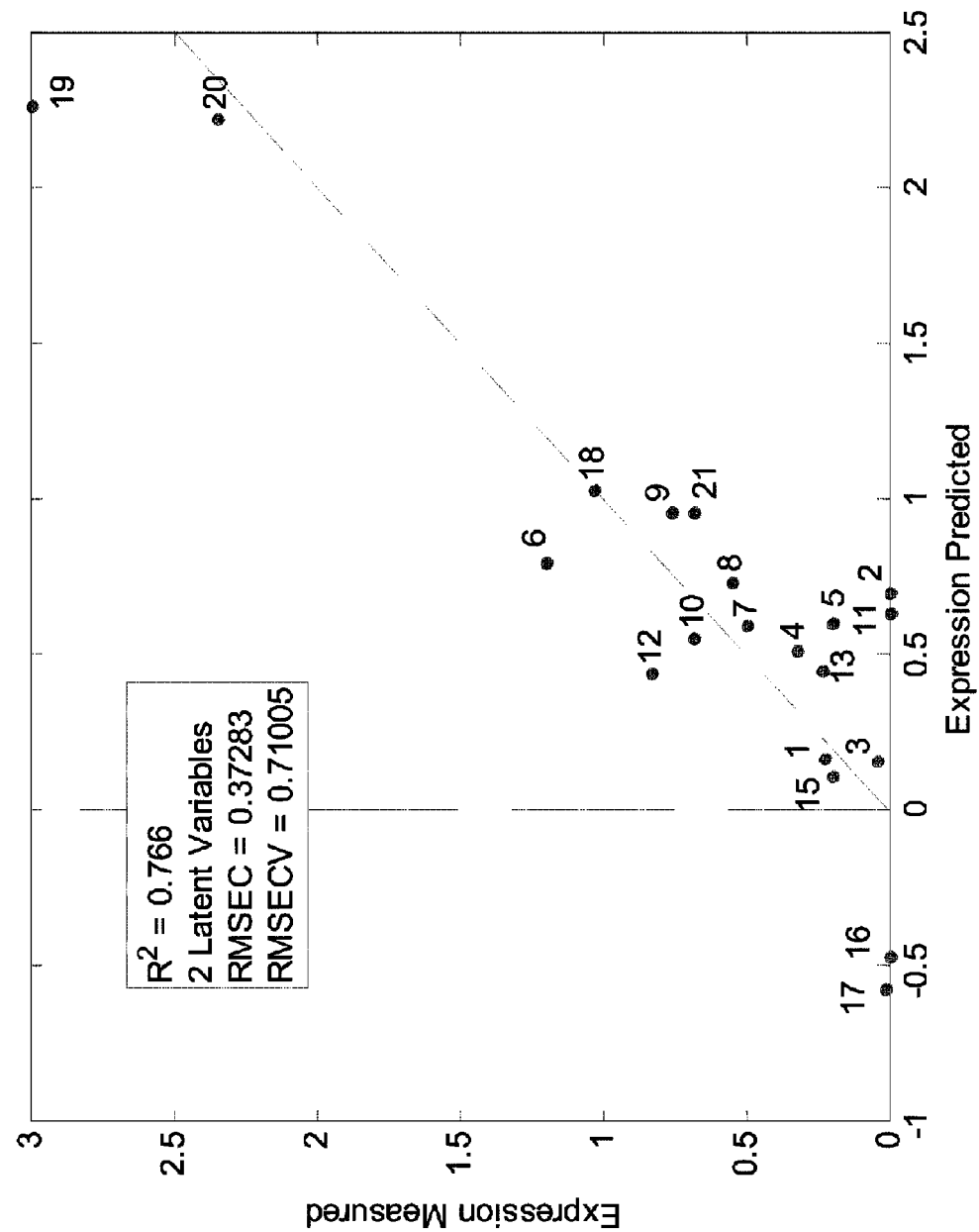
Figure 4B:
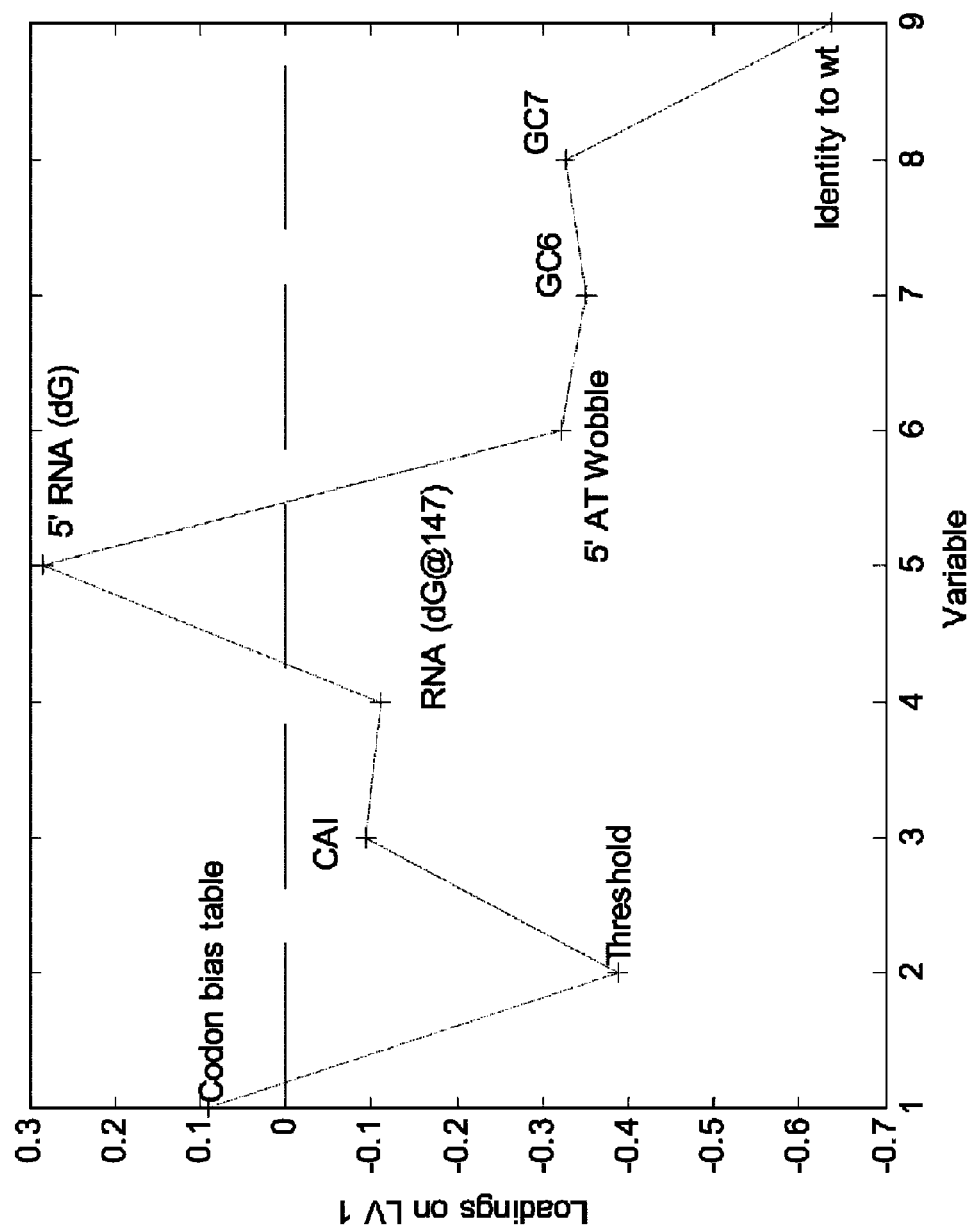
Figure 6A:
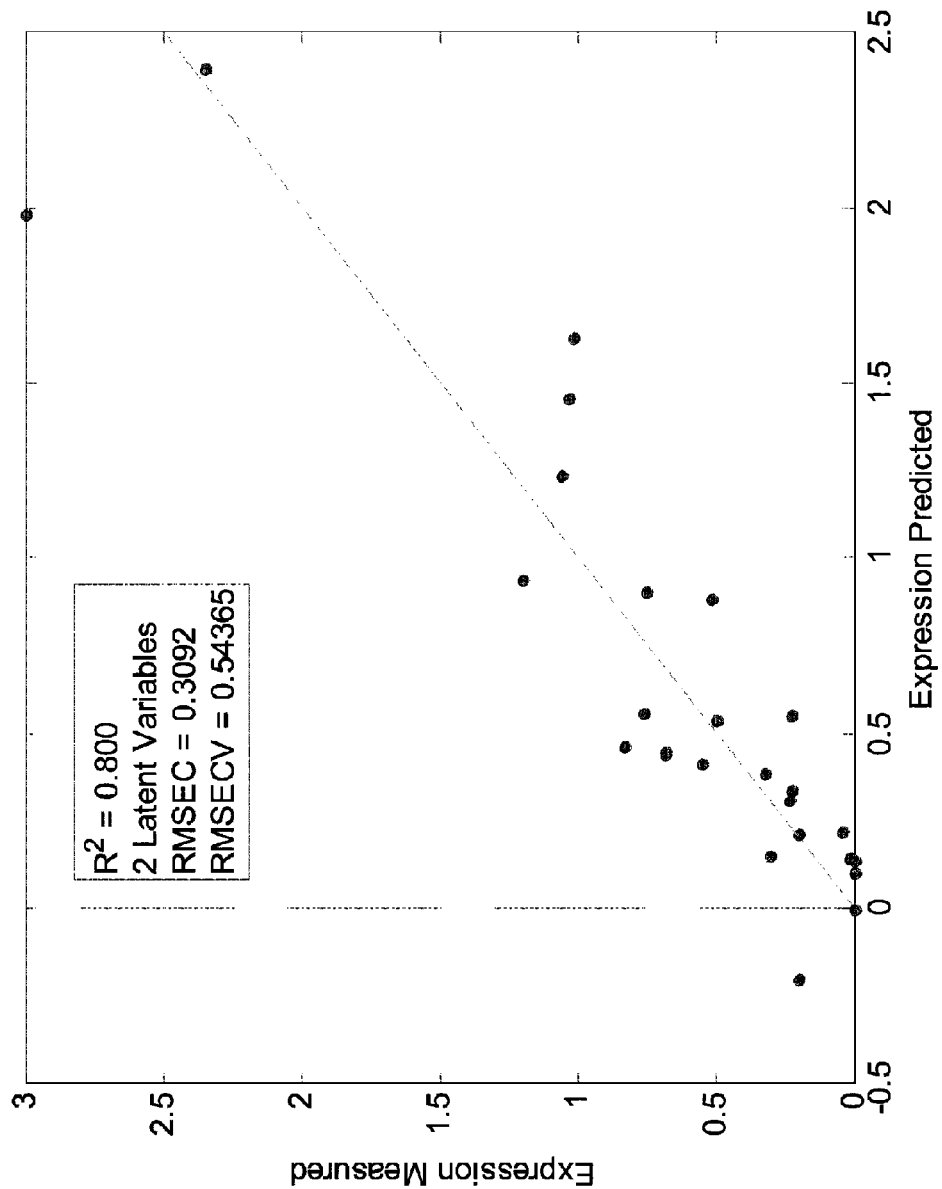
Figure 6B:
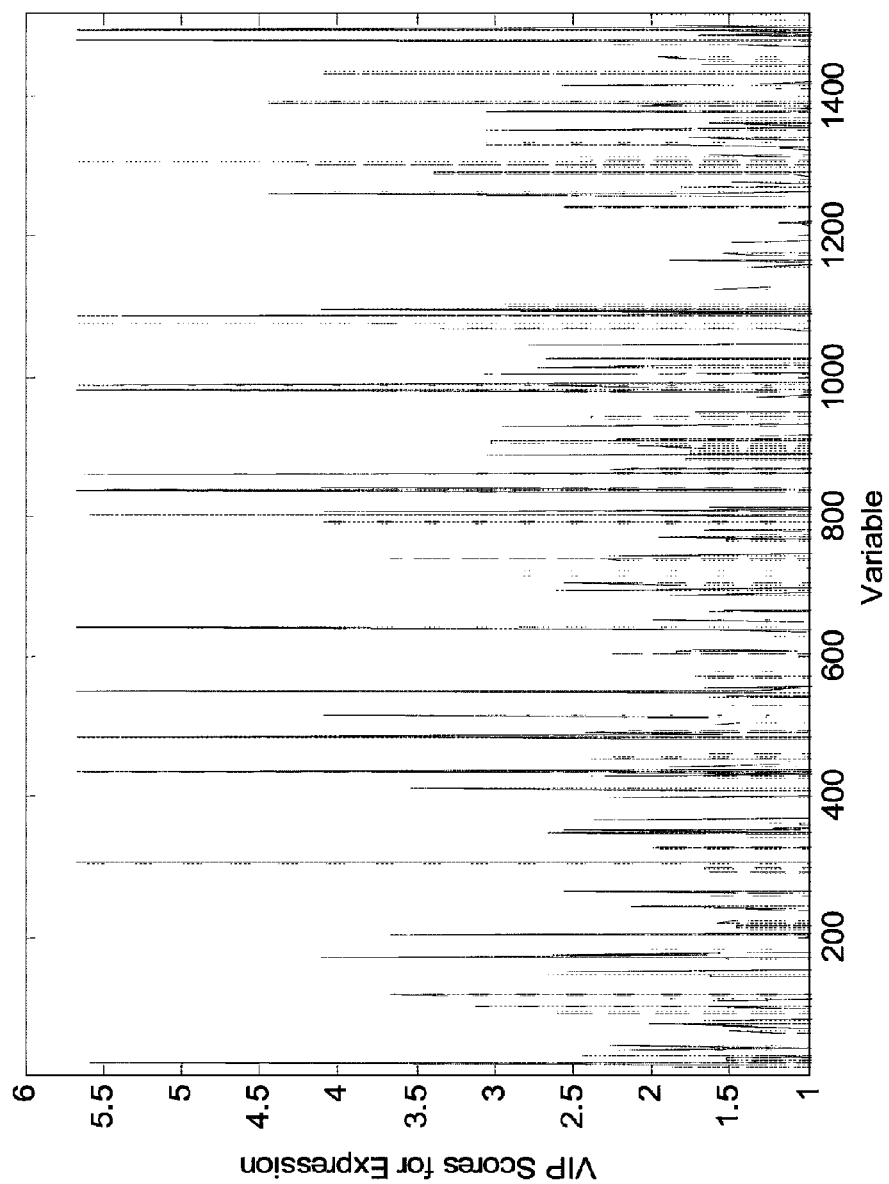

Correlation between observed and predicted expression levels for an initial PLS model of the phi29 polymerase variants data is shown in FIG. 4 part A. For this model, all variables listed in FIG. 2 were included, except GC %, which tightly correlates with 'identity to wt' and only contributes noise to this model fit. For modeling, the codon bias table is described by a binary term with *E. coli* genomic bias assigned the value −1 and *E. Coli* II bias is +1. RNA structure variables are entered as the absolute value of the predicted minimal free energy fold. In this model, 65% of the independent variables contributing to variation in protein expression were captured in latent variable 1 (LV1) and an additional 14% in LV2. FIG. 4 part B shows the loads of each of the initial design parameters on the first latent variable (LV1). This is a measure of the extent to which each initial design parameter influences the expression level of the phi29 gene variants.

The degree of identity between a variant and the wild type sequence was the most dominant factor in determining the protein expression levels that could be obtained from a gene. The two variants most different from wild-type, 19 and 20, showed more than two-fold higher expression than the next best variant. Also, contrary to conventional thinking, increasing the cutoff threshold for codons correlated with lower expression levels. A second parameter, the codon adaptation index (CAI). As defined here, the adaptiveness of a codon is defined as its usage frequency relative to that of the most frequently used synonymous codon in the E. coli II bias table. The CAI for the gene is the average codon adaptiveness over all positions. A commonly used gene optimization method is to maximize CAI, although no significant correlation of CAI with heterologous expression has been adequately demonstrated. CAI correlated negatively with protein expression in our experiments (FIG. 4 part B). High CAI scores and high cutoff thresholds both reflect a reduction in the diversity of codons used for some amino acids. These results suggest that limiting the total number of different codons used in the gene, may be detrimental. The model also suggests a negative effect of A/T bias in the third codon position of the first 15 codons and a positive effect of 5' RNA structure. It is not clear why stronger RNA structure around the initiation AUG would have a positive effect.

6.1.5 Analysis of Codon Bias and Expression for Phi 29 Variants

The factors affecting expression of phi29 variants all point to the influence of codon usage on expression. Two of the possible ways in which codon usage can be important are that there are relatively small numbers of rate-limiting positions, or that there is an optimal codon bias that is different from the E. coli genomic or Class II biases that we used in our original designs.

A new partial least squares (PLS) models was constructed using PLS Toolbox 4.0 software (Eigenvector, Inc.) within MATLAB (Mathworks, Inc), analyzing the sequences and expression levels of phi29 variants shown in FIG. 2 to identify specific codon choices that correlate best with activity. The variables used were the possible codons used at each position. For each codon position in the gene, the possible codon choices were assigned the value 1 if used and 0 if not, as shown for the first few positions in FIG. 5.

The complete set of variants contains 1517 variables. FIG. F part A shows the fit between predicted and measured expression levels for a Partial Least Squares (PLS) model of the expression and sequence of the 21 variants described in FIG. 2. FIG. F part B shows the positions in the polynucleotide sequence that were identified in this model as possible expression determining positions or regions.

PLS analysis of gene design features indicated some importance of the 5' initial sequence and a few positions in this sequence are identified by the codon-position analysis as correlating with expression. One site of interest is the codon for serine at position 10 and its neighboring codons at positions 9 and 11. In only the three top variants (6, 19 AND 20), the rather rare codon TCG was used at position 10. Also, strong biases are observed at positions 3 (CAC>CAT), 9 (TAC>TAT), 10 (TCG>TCC>others), 11 (TGC>TGT) and 13 (TTC>TTT).

More than 250 codon-positions had significant positive and negative load on expression according to the PLS model generated according to their variable importance in projection (VIP) scores for the model. VIP is a measure of the contribution of the variable to the model fitness based on comparison of models including or singly excluding the variable. Higher VIP means that error in the model is more highly increased upon omission of the variable. These higher VIP variables could be considered more likely to be critical for expression. Generally a VIP greater than 1 is considered significant to the model.

The importance of so many codon positions for expression implies that there is an overall codon bias requirement rather than a small number of rate-limiting positions or regions. To test this we synthesized 6 new genes designed as hybrids constructed from variants 19 and 15. Variant 19 was chosen because it was the variant expressing the highest levels of phi29. Variant 15 was chosen because it was the variant with lowest sequence identity to variant 19 that still had detectable levels of expressed protein. The parental genes (variants 15 and 19) were divided into three segments from codons 1-75, 76-325, and 326-575 and all six possible combinations were constructed and tested for expression as for the original variants (Table A).

All segments were found to be critical and essentially independent in their contributions to expression. Any substitution of a segment in variant 19 with the corresponding segment from variant 15 reduced expression 3- to 4-fold. Replacement of the 3' segment was most deleterious. Conversely, substitutions of either 5' or 3' segments of variant 15 with the corresponding segment from variant 19 increased expression 1.5 to 2.5-fold, though we saw no significant improvement when the middle segment of variant 15 was replaced. The intermediate expression levels that result from these hybrid constructs suggest that there is not a single dominant rate-determining region (i.e., a particular cis regulatory element) in the gene coding sequence. Instead it is consistent with the overall codon bias being the primary determinant of the expression levels observed.

TABLE A

Relative expression of phi29 polymerase gene variants 15 and 19 and hybrids between the two.

| Variant | Parent for segment 1-75 | Parent for segment 76-325 | Parent for segment 326-575 | Relative Expression |
|---|---|---|---|---|
| 15 | | | | 20 ± 4 |
| 19 | | | | 301 ± 65 |
| Hyb 15-15-19 | 15 | 15 | 19 | 51 ± 17 |
| Hyb 15-19-15 | 15 | 19 | 15 | 22 + 3 |
| Hyb 19-15-15 | 19 | 15 | 15 | 30 ± 4 |
| Hyb 15-19-19 | 15 | 19 | 19 | 101 ± 7 |
| Hyb 19-15-19 | 19 | 15 | 19 | 106 ± 11 |
| Hyb 19-19-15 | 19 | 19 | 15 | 75 ± 8 |

Figure 7:
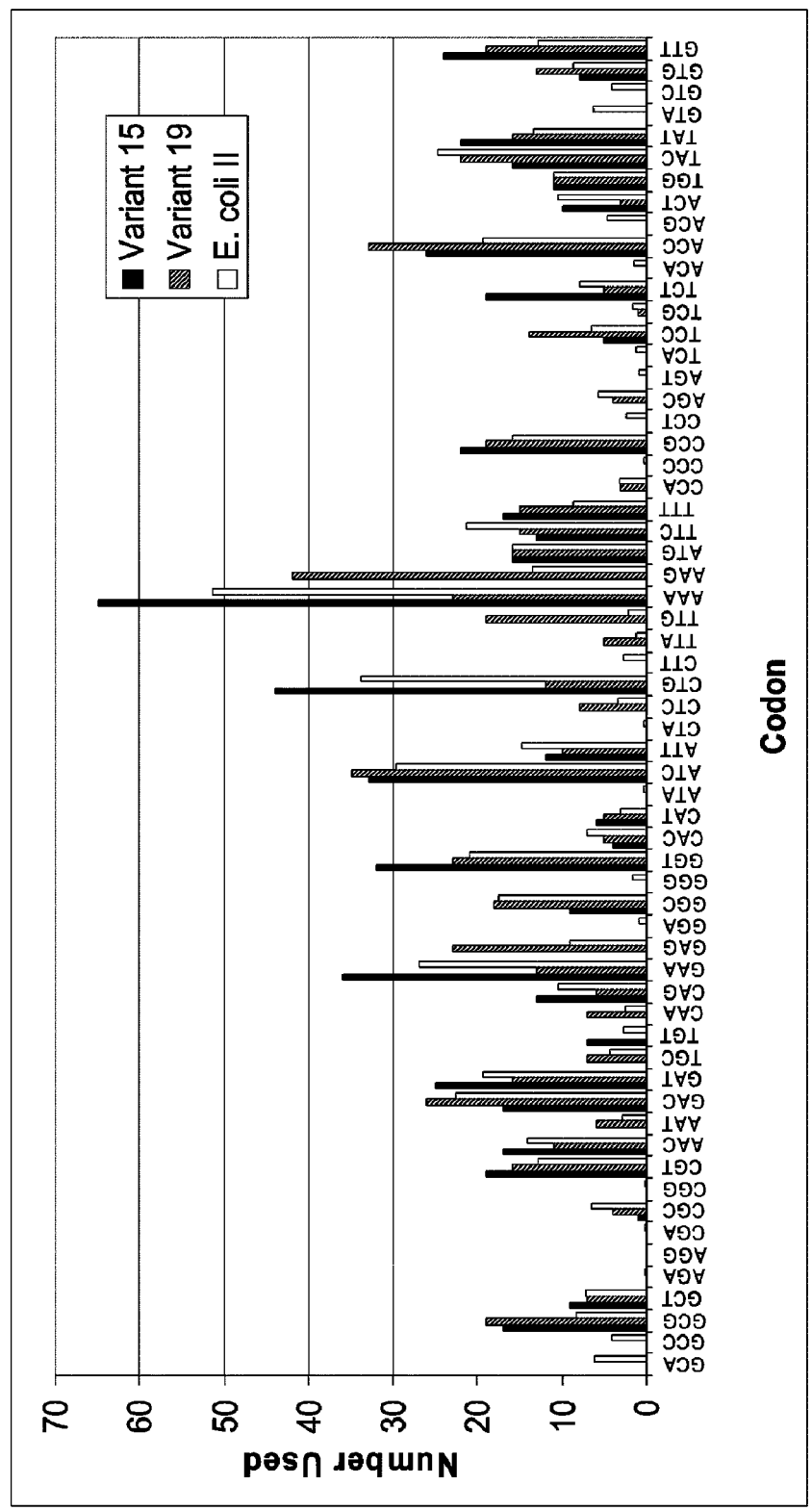

The overall codon biases for variants 15 and 19 are quite different from each other and from that found in E. coli class II genes, as shown in FIG. 7. The bias in variant 15 is much closer to that of E. coli class II genes than is the bias in variant 19. The codon bias in variant 19 is much "flatter" than in variant 15, that is the codons for each amino acid are much more evenly distributed.

Figure 8:
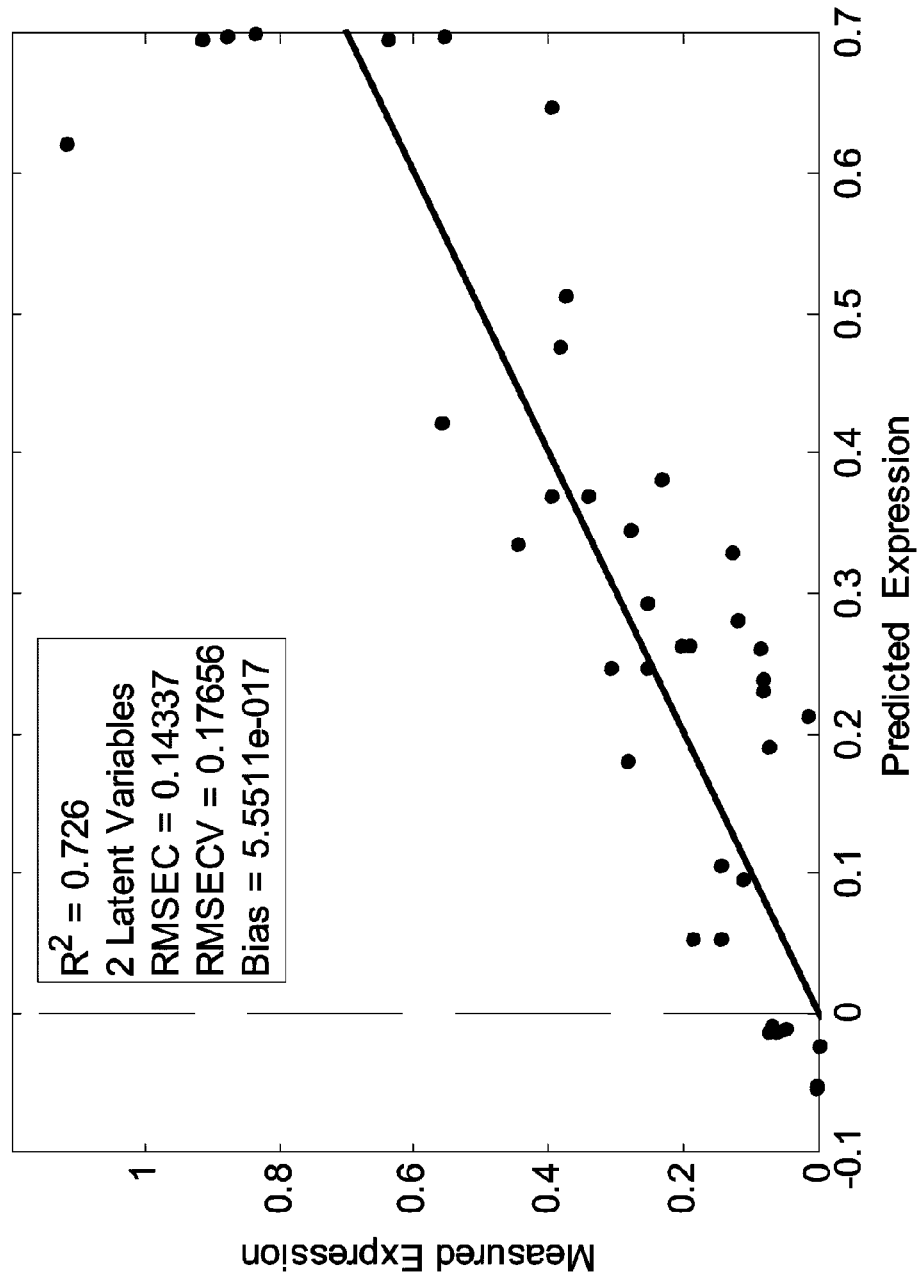

A new partial least squares (PLS) model was constructed using PLS Toolbox 4.0 software (Eigenvector, Inc.) within MATLAB (Mathworks, Inc). This model used the 59 codons that had synonymous alternatives (that is all codons except the three stop codons, ATG (Met) and TGG (Trp)) as the independent variables to describe the polynucleotide sequence property. The latent variables, variable importance in projection and regression vector in Y were calculated for each codon, the fit between measured and predicted expression levels are shown in FIG. 8.

Figure 11:
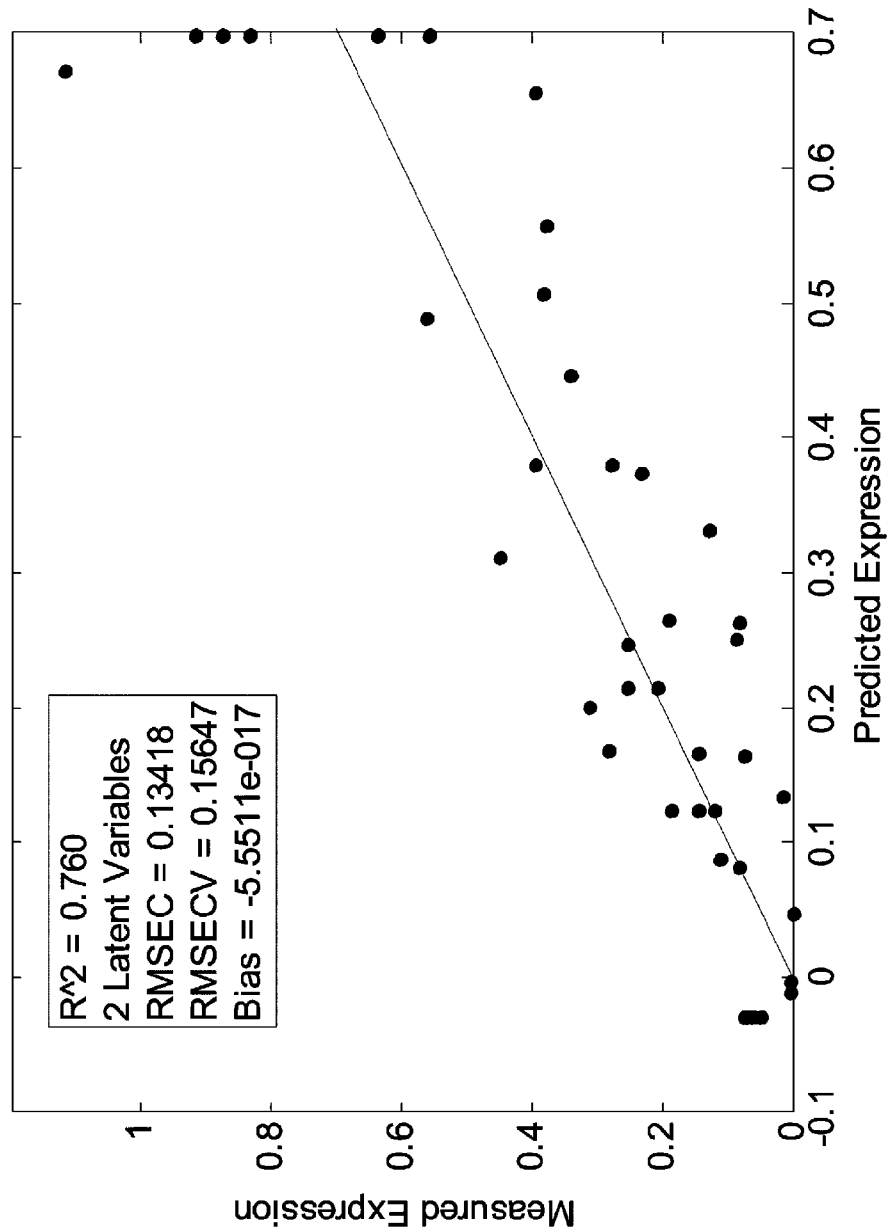
FIG. 11 illustrates a PLS modeling of phi29 DNA polymerase expression as a function of the frequency of 12 codons selected as the most important using a genetic algorithm. The graph shows correlation between measured and predicted values.

A new partial least squares (PLS) model was constructed using the Genetic Algorithm function in PLS Toolbox 4.0 software (Eigenvector, Inc.) within MATLAB (Mathworks, Inc). The genetic algorithm compared models using 100 different random subsets of 15-25 of the 61 sense codons, and evaluated their ability to explain the data in PLS modeling. The error of the PLS fit of the data in cross validation (RMSECV) was used to distinguish the subsets. Those that yielded lower than median RMSECV were retained. The codon sets used by random pairs of these selected samples were then recombined at two randomly selected crossover points to create new progeny samples. The resulting samples, the original selected and their progeny, were then analyzed for fit as before and the best half were used to create the next sample generation. At each generation, mutation (substituting one codon variable in a sample for another) was allowed to prevent the model from prematurely eliminating or fixing under- or overrepresented variables, respectively. The entire process was repeated until there was convergence in makeup and performance of the selected population. In this way we identified 12 codons that were most significant for expression. The fit between measured and predicted expression levels is shown in FIG. 11.

6.2 DESIGN, SYNTHESIS & EXPRESSION TESTING OF A CODON VARIANT SET FOR A SINGLE CHAIN ANTIBODY FRAGMENT

6.2.1 ScFv Variant Design

We created a set of gene variants encoding a 281 codon single-chain antibody fragment (scFv). The scFv gene variants were diversified in a similar fashion to the phi29 polymerase variants, as described in detail in section 6.1.1.

A set of 6 gene design parameters were varied between the designs. These were:

1. Codon bias. Codon bias describes the relative frequency with which synonymous codons are used to encode an amino acid. We used two codon bias tables, one calculated from all of the genes in the *E. coli* genome ('*E. coli*' table) and a second from a subset of 27 genes that are highly expressed ('*E. coli* II' table) (Gustafsson et al., 2004, "Codon bias and heterologous protein expression," Trends Biotechnol: 22, 346-353; Henaut and Danchin, 1996, "Analysis and predictions from *Escherichia coli* sequences," *Escherichia coli* and *Salmonella typhimurium* Cellular and Molecular Biology 2, 2047-2066; Sharp and Li, 1987, "The codon Adaptation Index—a measure of directional synonymous codon usage bias, and its potential applications," Nucleic Acids Res 15, 1281-1295). We also created 3 "flattened" tables based on each of these. This was achieved by reducing the difference between the frequency of a codon in the codon bias table used and the mean frequency for each codon encoding that amino acid. For example, lysine is encoded by AAA 79% of the time and AAG 21% of the time in *E. coli* class II genes. The mean of these frequencies is 50%. Flattening this codon bias by 50% would reduce the frequency of AAA by (79-50)/2=14.5% to 64.5%, and increase the frequency of AAG by (50-21)/2=14.5% to 35.5%. A 100% flattening would result in all possible codons above threshold are used at equal frequency. The cutoff thresholds used, however, were based on the codon frequencies in the original codon table. To design each gene variant encoding ScFv, we used Gene Designer software (Villalobos et al, 2006, "Gene Designer: a synthetic biology tool for constructing artificial DNA segments," BMC Bioinformatics: 7, 285). For each consecutive amino acid the program chooses a codon with a probability that is proportional to its frequency in the chosen bias table. Thus the overall bias of the gene approximates that of the bias table.

2. Cutoff threshold. Several previous reports have shown that use of some rarely used codons may lower expression, particularly when these are used frequently or in tandem (Kane, 1995, "Effects of rare codon clusters on high-level expression of heterologous proteins in *Escherichia coli*," Curr Opin Biotechnol 6, 494-500; Shu et al., 2006, "Inhibition of translation by consecutive rare leucine codons in *E. coli*: absence of effect of varying mRNA stability," Gene Expr: 13, 97-106. We therefore used Gene Designer to exclude codons whose frequencies in the codon bias table are lower than a selected threshold (the cutoff threshold). We varied this threshold to test whether inclusion of codons used at intermediate frequency or occasional inclusion of rare codons have a detrimental effect. At the highest threshold settings used (25%, that is, the only codons allowed are those that are used to encode an amino acid more than 25% of the time in the genes from which that codon bias table is derived), 5-6 amino acids that could be encoded by multiple codons are restricted to a single choice. At the lowest settings (2%) only 0-6 of the rarest codons are excluded.

3. Internal RNA structure. After initial coding we analyzed the RNA secondary structure of each variant using UNAFold (Markham and Zuker, 2005, "DINAMelt web server for nucleic acid melting prediction," Nucleic Acids Res 33, W577-W581). RNA structures were determined for every 50 nucleotide window of the coding sequence, and for the 3' terminal tail of the mRNA consisting of the last 50 nucleotides of the coding sequence through to the expected terminus. A 50 nucleotide window was used because it should identify local structures that can form between consecutive ribosomes on an mRNA: ribosome spacing is estimated at 50 nucleotides for a rapidly translating message. There were multiple possible strong internal RNA structures but only one, near position 83 of the coding sequence, could be engineered mostly independent of codon bias. RNA structure at several positions were analyzed and included in modeling, but none, including that at 83, contributed significantly to fitting.

4. RNA structure at the 5' initiation site. We used UNAFold to calculate the RNA structure from the 5' end of the mRNA to position +50. This structure was manually modified in selected genes by minimal codon substitutions, within the bias and threshold limits.

5. 5' AT wobble. We manually modified the percentage of the first 15 codons that use A or T in the 3rd position 6. GC runs. Runs of G and/or C of 6 or 7 nucleotides or more were avoided in some sequences by defining SSSSSS/S(S=G or C) as a motif to avoid in Gene Designer.

Five parameters (codon bias (including degree of "flattening"), threshold, internal RNA structure, AT wobble, and GC runs), were systematically varied. The design properties of the first 24 variants are shown in Table B.

TABLE B

Gene design parameter matrix for scFv test variants. Expression is relative to variant 13.

| ScFv Var. | Codon bias table | Threshold | % Flat[b] | CAI | RNA (dG@83) | 5' RNA (dG) | 5' AT Wobble | GC6 | GC7 | Expression |
|---|---|---|---|---|---|---|---|---|---|---|
| V1 | E. coli | 0.20 | 50 | 0.718 | −17.6 | −26.9 | 0.400 | 7 | 2 | 281 ± 27 |
| V2 | E. coli | 0.05 | 50 | 0.443 | −11.0 | −28.6 | 0.067 | 7 | 3 | 21 ± 6 |

TABLE B-continued

Gene design parameter matrix for scFv test variants. Expression is relative to variant 13.

| ScFv Var. | Codon bias table | Threshold | % Flat[b] | CAI | RNA (dG@83) | 5' RNA (dG) | 5' AT Wobble | GC6 | GC7 | Expression |
|---|---|---|---|---|---|---|---|---|---|---|
| V3  | E. coli II | 0.20 | 50  | 0.804 | −19.6 | −26.6 | 0.200 | 11 | 4 | 78 ± 11 |
| V4  | E. coli II | 0.02 | 50  | 0.556 | −22.5 | −27.2 | 0.667 | 10 | 7 | 173 ± 17 |
| V5  | E. coli II | 0.02 | 0   | 0.703 | −13.3 | −28.0 | 0.667 | 9  | 2 | 163 ± 17 |
| V6  | E. coli II | 0.25 | 0   | 0.863 | −22.8 | −26.1 | 0.067 | 8  | 3 | 152 ± 19 |
| V7  | E. coli    | 0.20 | 0   | 0.716 | −24.8 | −26.9 | 0.400 | 11 | 6 | ND |
| V8  | E. coli    | 0.03 | 0   | 0.472 | −18.4 | −25.0 | 0.133 | 9  | 4 | ND |
| V9  | E. coli II | 0.20 | 50  | 0.825 | −16.9 | −26.2 | 0.400 | 6  | 0 | 221 ± 22 |
| V10 | E. coli II | 0.02 | 50  | 0.552 | −27.2 | −27.2 | 0.200 | 4  | 1 | 109 ± 25 |
| V11 | E. coli    | 0.20 | 50  | 0.719 | −18.0 | −27.9 | 0.067 | 12 | 5 | ND |
| V12 | E. coli    | 0.05 | 50  | 0.395 | −23.8 | −25.9 | 0.800 | 10 | 6 | 182 ± 28 |
| V13 | E. coli    | 0.02 | 0   | 0.459 | −12.3 | −26.0 | 0.733 | 9  | 1 | 100 ± 12 |
| V14 | E. coli    | 0.20 | 0   | 0.742 | −27.9 | −30.1 | 0.067 | 7  | 2 | ND |
| V15 | E. coli II | 0.27 | 0   | 0.858 | −23.6 | −27.6 | 0.400 | 6  | 5 | 55 ± 13 |
| V16 | E. coli II | 0.02 | 0   | 0.714 | −17.2 | −33.8 | 0.133 | 8  | 4 | ND |
| V17 | E. coli II | 0.10 | 0   | 0.815 | −17.3 | −24.8 | 0.400 | 8  | 4 | 61 ± 9 |
| V18 | E. coli II | 0.10 | 0   | 0.759 | −19.4 | −28.9 | 0.333 | 5  | 3 | 71 ± 5 |
| V19 | E. coli II | 0.10 | 0   | 0.8   | −18.6 | −28.6 | 0.267 | 10 | 4 | ND |
| V20 | E. coli II | 0.20 | 100 | 0.788 | −19.0 | −26.7 | 0.200 | 7  | 2 | 63 ± 10 |
| V21 | E. coli II | 0.10 | 100 | 0.665 | −17.4 | −25.6 | 0.333 | 3  | 0 | 241 ± 24 |
| V22 | E. coli    | 0.07 | 100 | 0.404 | −18.4 | −23.7 | 0.400 | 8  | 2 | 107 ± 10 |
| V23 | E. coli II | 0.10 | 0   | 0.794 | −16.6 | −27.5 | 0.333 | 10 | 4 | 182 ± 19 |
| V24 | E. coli II | 0.10 | 0   | 0.797 | −21.4 | −25.9 | 0.267 | 10 | 6 | ND |

6.2.2 scFv Variant Synthesis and Cloning

The gene variants were all synthesized by standard gene synthesis procedures and cloned into a pET24a expression vector between the XbaI and EcoRI restriction sites. This put each gene under transcriptional control of the strong T7 RNA polymerase promoter of this vector. Each final construct was completely sequenced in both directions to be certain that the complete sequence was as designed. The plasmid was then used to transform E. coli expression host strain BL21(DE3) harboring a second plasmid for low level expression of T7 lysozyme, pLysS. The background expression of T7 lysozyme, an inhibitor of T7 RNA polymerase, gives tight repression of heterologous expression prior to induction to minimize potential gene toxicity which could affect data quality.

6.2.3 ScFv Variant Expression

Proteins were expressed from the variant genes using standard methods. Prior to analysis of the variants, expression was analyzed for multiple variants to determine appropriate expression time and temperature. Strong, consistent expression was achieved at 30° C., a commonly used temperature for heterologous expression in E. coli. Time courses at 30° C. showed expressed protein levels increasing to a maximum after approximately two hours, as the cells entered stationary phase growth, and remaining steady for at least five hours. Relative protein expression levels between variants were consistent throughout the time course. For our variant analysis we chose to express for four hours at 30° C.

Figure 9:
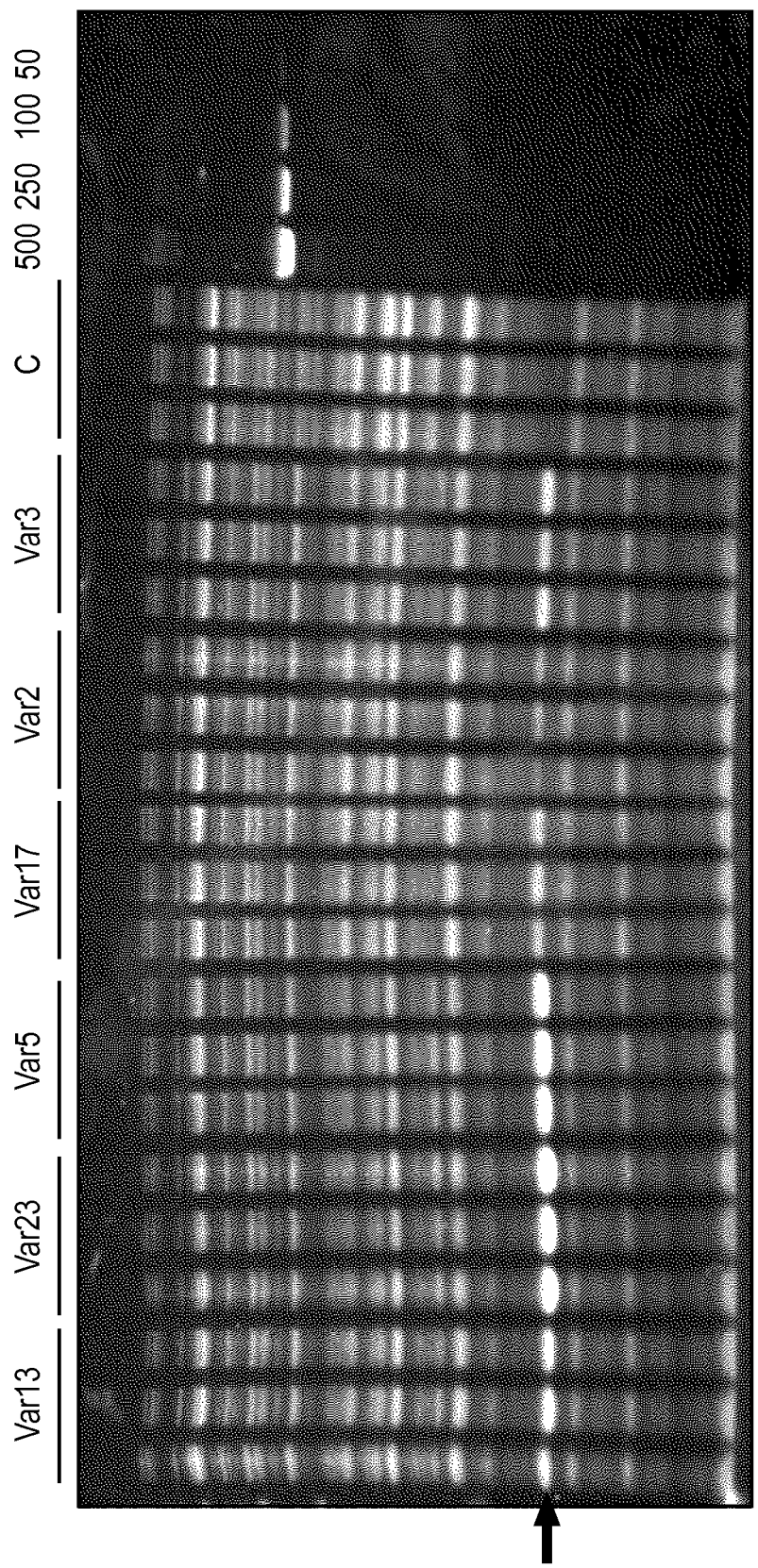

For each variant, three transformants were picked and cultured overnight in 2 ml Luria Broth (LB) containing appropriate antibiotics to maintain the expression vector and pLysS plasmid. The overnight cultures were diluted 50-fold in fresh media and incubated at 37° C. until the cells were in mid-log growth (OD at 600 nm ~0.6). Expression was induced by addition of IPTG to 1 mM and incubation for four hours at 30° C. Final optical densities of cultures were measured and equivalent amounts of culture were analyzed by polyacrylamide gel electrophoresis (a sample set of variant expression is shown in FIG. 9). Gels were stained with Sypro Ruby (Pierce), visualized by fluorescence imaging, and protein band intensities quantified using TotalLab 100 image analysis software (Nonlinear Dynamics, Inc). Each gel contained protein concentration standards to calibrate band intensity. Three replicates of a reference clone (ScFv variant 13) were expressed in parallel cultures in each experiment to allow corrections to be made for any experiment to experiment variation. Reported expression levels are all relative to this reference. The detection limit of the assay was approximately 1 μg of ScFv per ml culture at an $A_{600}=3$. The standard error of measured expression for variant repeats was generally <20% of the mean.

Quantitation of expression levels for the variants was assessed. There are a wide range of expression levels among the variants, demonstrating a good sampling of expression relevant features in our gene designs. Levels ranged from below detection to three times the reference, a range of two orders of magnitude.

6.2.4 Analysis of Gene Design Parameters for ScFv Variants

To determine the influence of the various gene design parameters on expression, the data was fit to partial least squares (PLS) models using PLS Toolbox 4.0 software (Eigenvector, Inc.) within MATLAB (Mathworks, Inc). PLS regression is a highly reliable method for modeling systems data where the number of independent variables is high, approaching or even exceeding the number of samples (Eriksson et al., Wold, 2004, "Using chemometrics for navigating in the large data sets of genomics, proteomics, and metabonomics (gpm)," Anal Bioanal Chem: 380, 419-429). In PLS regression, multivariate data are transformed to a variable space with reduced dimensionality that is defined by new orthogonal variables (latent variables). The latent variables are linear combinations of the original variables, calculated to maximize correlation between independent and dependent variables in as few dimensions as possible. Cross-validation methods are used to determine the optimal number of latent variables to use in the model, so that fit between data and model is maximized without over-fitting.

Figure 10A:
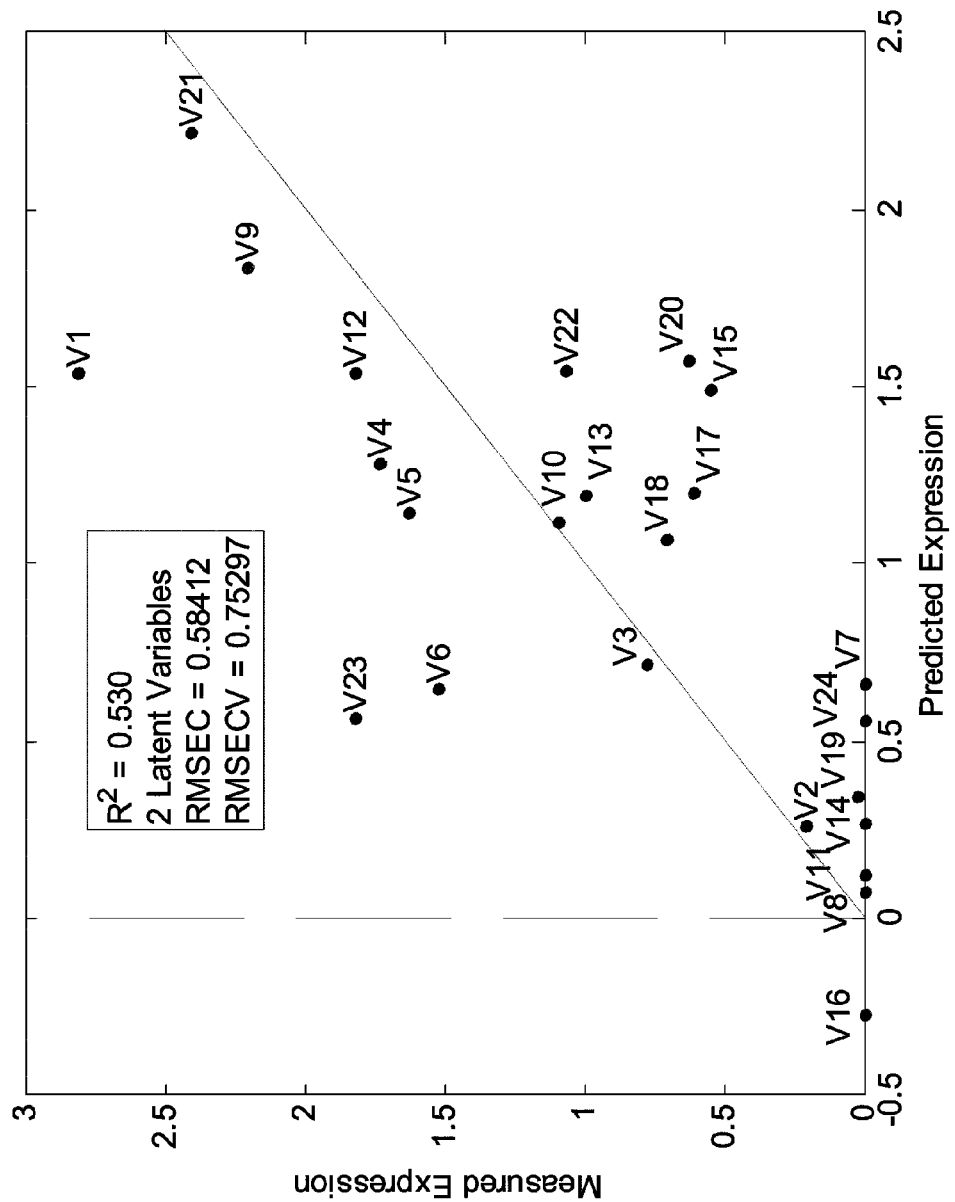
Figure 10B:
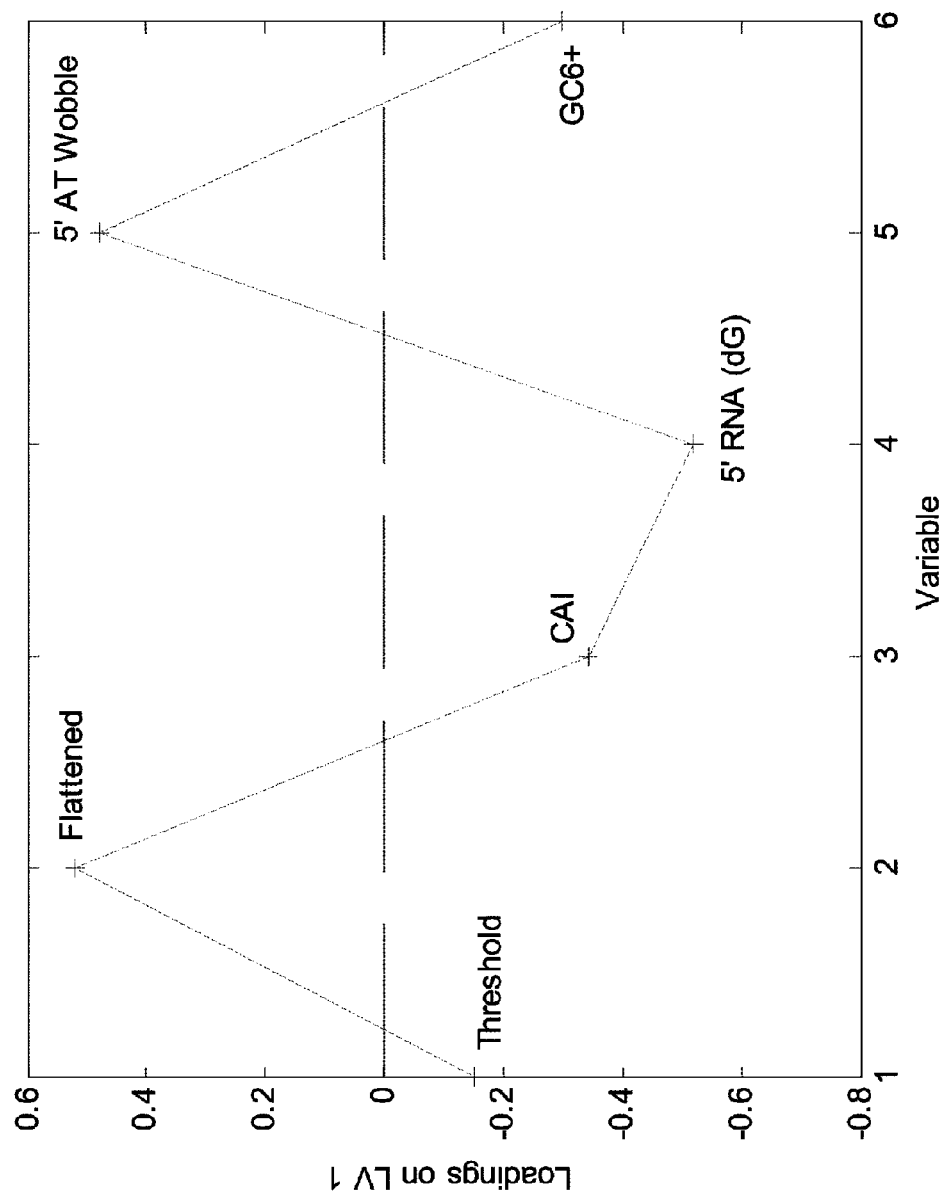

Correlation between observed and predicted expression levels for an initial PLS model of the ScFv variants data is shown in FIG. 10 part A. FIG. 10 part B shows the contributions of varied parameters to the expression of the scFv. Most striking, and consistent with our predictions from phi29 variants in Example 6.1, we observe a positive effect of flattening the codon bias. The three highest expressing variants all have flattened bias, including the 100% flattened variant 21. These results indicate that there is an advantage to sampling a more diverse codon usage than is typically done in standard gene optimization. Also consistent with our results from phi29 polymerase, CAI does not correlate positively with expression. In fact, once again, we observe a negative effect of high CAI and, more weakly, threshold, again suggesting that a different codon bias is optimal.

We also see correlation of expression with 5' codon usage. Both 5'-AT Wobble and 5'-RNA structure correlate with expression, although in this case higher A/T usage and weaker structure is preferred, opposite of the preferences seen with phi29 polymerase. As with the phi29 polymerase, AT wobble and 5' RNA structure are heavily influenced by codon biases.

Figure 12:
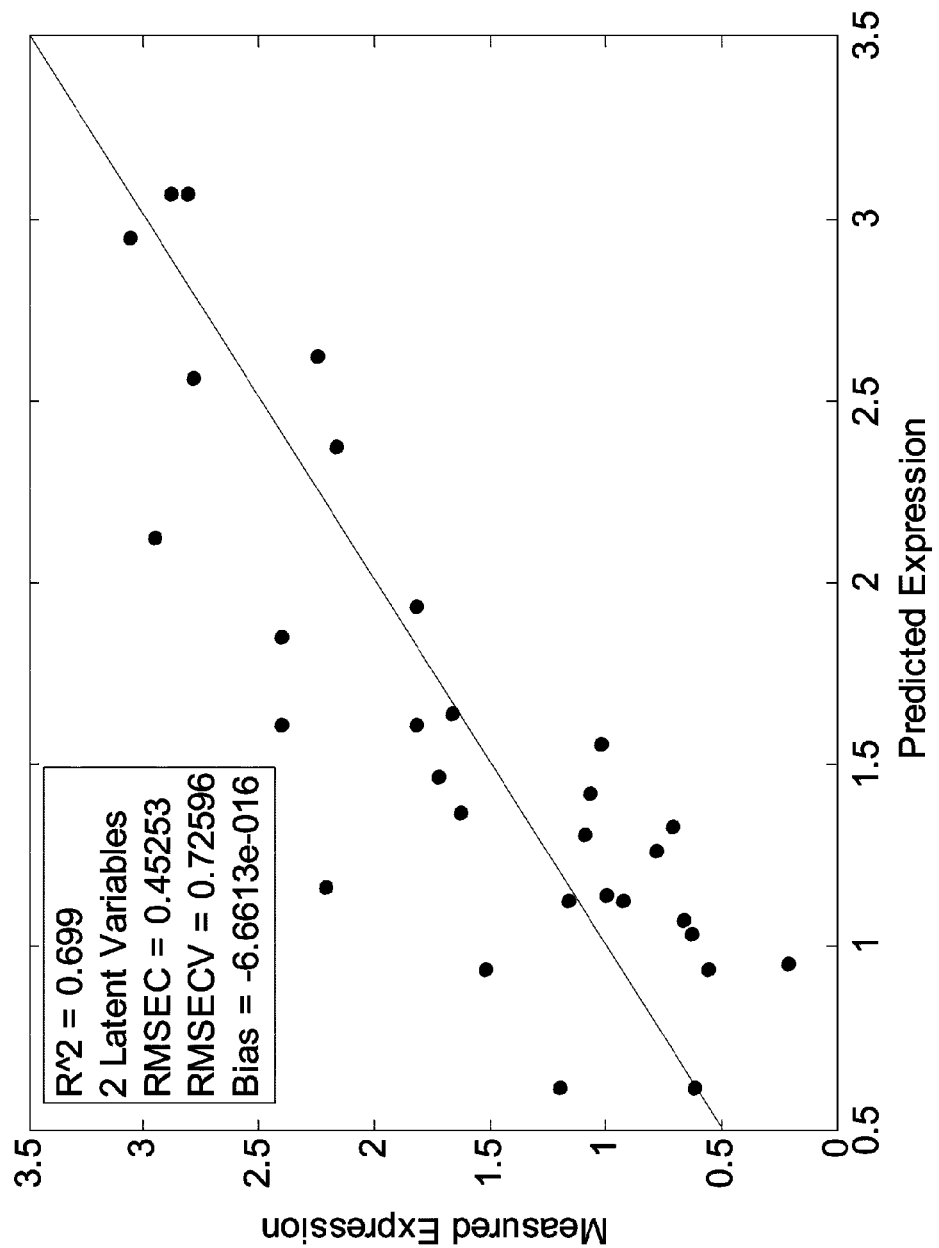
FIG. 12 shows PLS modeling of ScFv expression as a function of the frequency of each of the 59 variable codons. The graph shows correlation between measured and predicted values.

A new partial least squares (PLS) model was constructed using PLS Toolbox 4.0 software (Eigenvector, Inc.) within MATLAB (Mathworks, Inc). This model used the 59 codons that had synonymous alternatives (that is all codons except the three stop codons, ATG (Met) and TGG (Trp)) as the independent variables to describe the polynucleotide sequence property. The latent variables, variable importance in projection and regression vector in Y were calculated for each codon, the fit between measured and predicted expression levels for this model are shown in FIG. 12.

Figure 13:
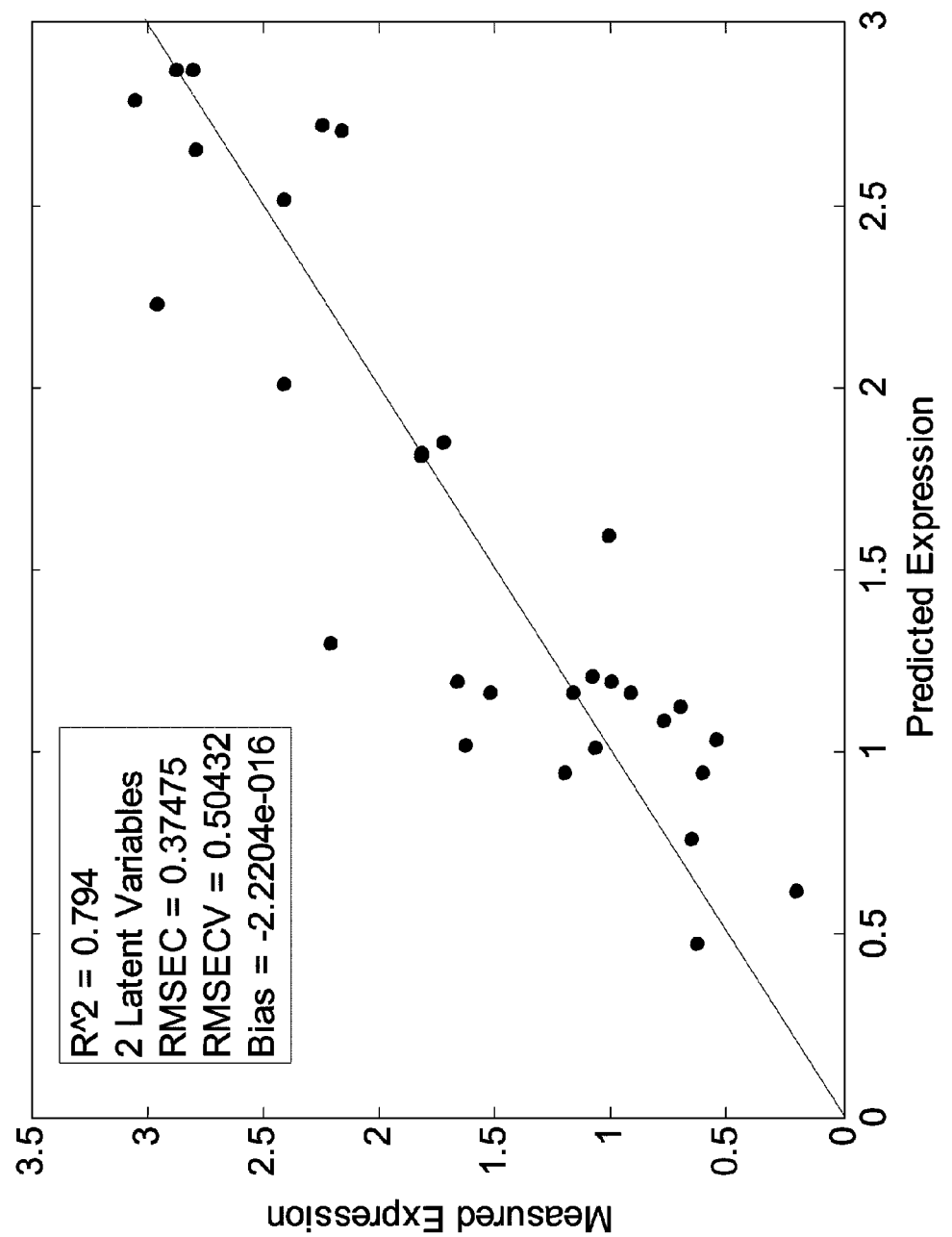
FIG. 13 shows PLS modeling of ScFv expression as a function of the frequency of 12 codons selected as the most important using a genetic algorithm. The graph shows correlation between measured and predicted values.

A new partial least squares (PLS) model was constructed using the Genetic Algorithm function in PLS Toolbox 4.0 software (Eigenvector, Inc.) within MATLAB (Mathworks, Inc). The genetic algorithm compared models using 100 different random subsets of 15-25 of the 61 sense codons, and evaluated their ability to explain the data in PLS modeling. The error of the PLS fit of the data in cross validation (RMSECV) was used to distinguish the subsets. Those that yielded lower than median RMSECV were retained. The codon sets used by random pairs of these selected samples were then recombined at two randomly selected crossover points to create new progeny samples. The resulting samples, the original selected and their progeny, were then analyzed for fit as before and the best half were used to create the next sample generation. At each generation, mutation (substituting one codon variable in a sample for another) was allowed to prevent the model from prematurely eliminating or fixing under- or overrepresented variables, respectively. The entire process was repeated until there was convergence in makeup and performance of the selected population. In this way we identified 12 codons that were most significant for expression. The fit between measured and predicted expression levels is shown in FIG. 13.

6.3 COMBINED SEQUENCE-EXPRESSION ANALYSIS OF CODON VARIANT SETS FOR PHI 29 DNA POLYMERASE AND A SINGLE CHAIN ANTIBODY FRAGMENT

6.3.1 Modeling Codon Expression Data

Figure 14:
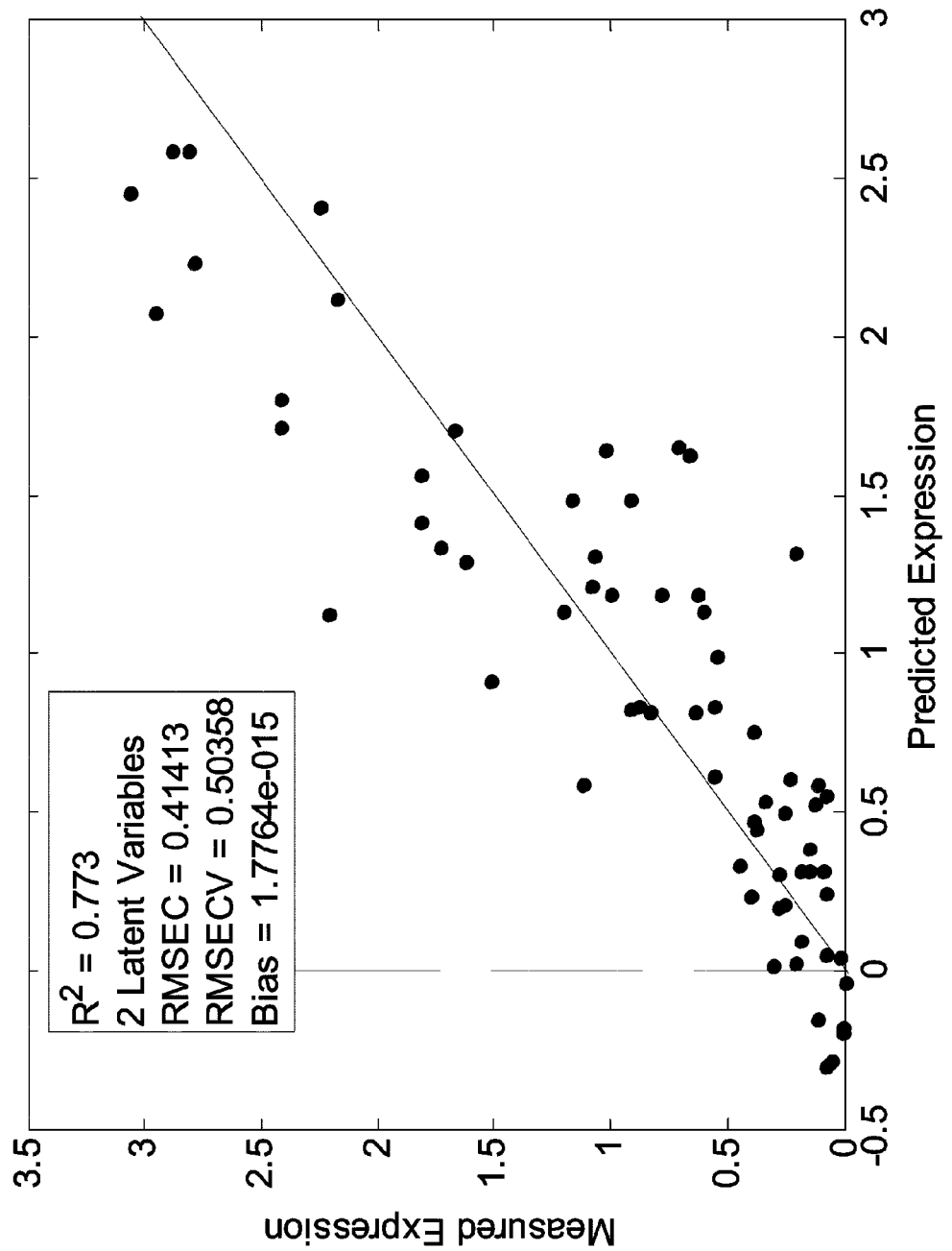
FIG. 14 shows PLS modeling of protein expression as a function of the frequency of each of the 59 variable codons for combined data from ScFv and phi29 variants. The graph shows correlation between measured and predicted values.

A partial least squares (PLS) model was constructed for the combined data for phi29 and ScFv variants for which activity data was shown in FIG. 2. The model was constructed using PLS Toolbox 4.0 software (Eigenvector, Inc.) within MATLAB (Mathworks, Inc). This model used the 59 codons that had synonymous alternatives (that is all codons except the three stop codons, ATG (Met) and TGG (Trp)) as the independent variables to describe the polynucleotide sequence property. The latent variables, variable importance in projection and regression vector in Y were calculated for each codon. The fit between measured and predicted expression levels for this model are shown in FIG. 14.

Figure 15:
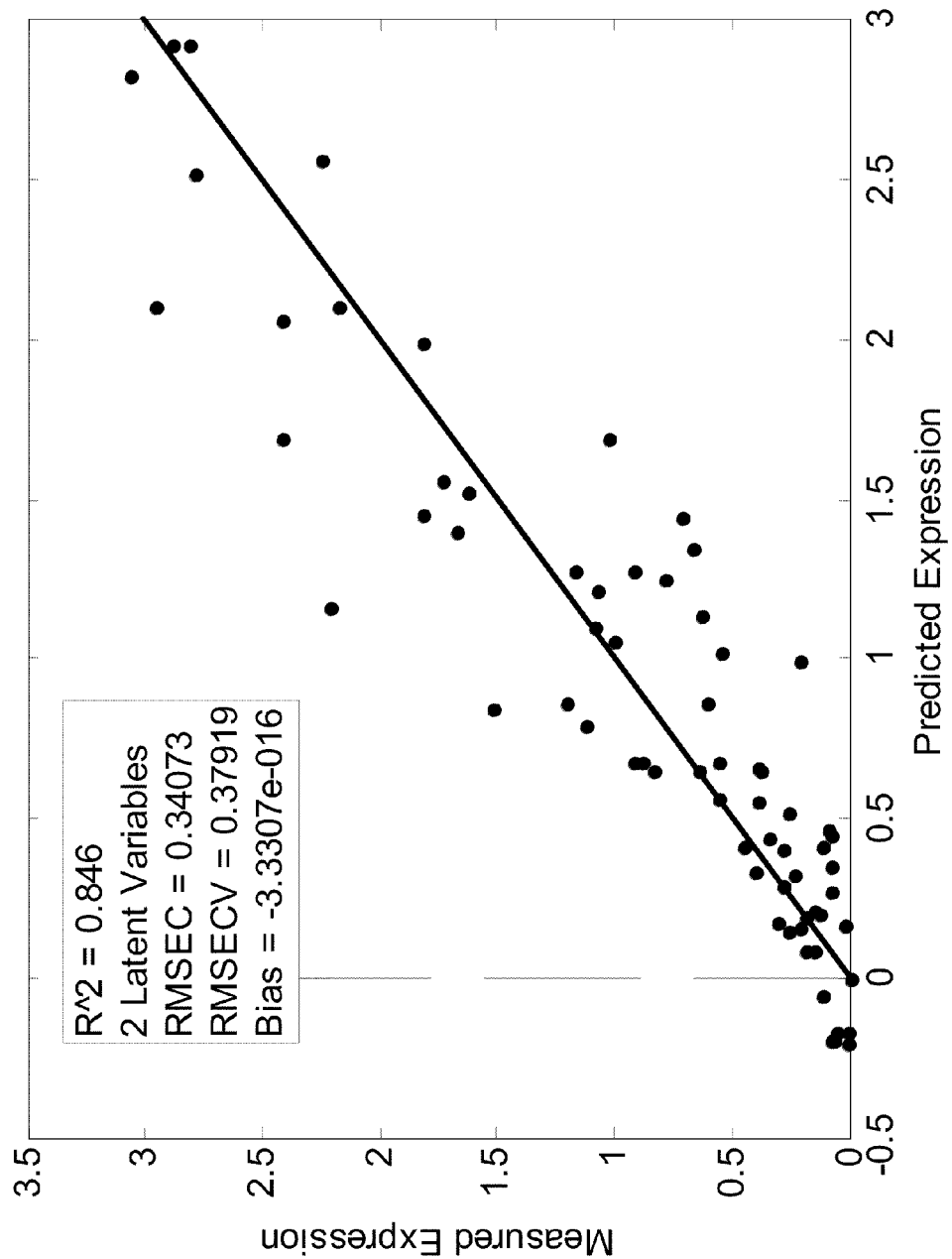
FIG. 15 shows a fit between measured and predicted expression levels in accordance with an embodiment of the present invention.

A new partial least squares (PLS) model was constructed for a dataset including both the ScFv and phi29 sequences using the Genetic Algorithm function in PLS Toolbox 4.0 software (Eigenvector, Inc.) within MATLAB (Mathworks, Inc). The genetic algorithm compared models using 100 different random subsets of 15-25 of the 61 sense codons, and evaluated their ability to explain the data in PLS modeling. The error of the PLS fit of the data in cross validation (RMSECV) was used to distinguish the subsets. Those that yielded lower than median RMSECV were retained. The codon sets used by random pairs of these selected samples were then recombined at two randomly selected crossover points to create new progeny samples. The resulting samples, the original selected and their progeny, were then analyzed for fit as before and the best half were used to create the next sample generation. At each generation, mutation (substituting one codon variable in a sample for another) was allowed to prevent the model from prematurely eliminating or fixing under- or overrepresented variables, respectively. The entire process was repeated until there was convergence in makeup and performance of the selected population. In this way we identified 16 codons that were most significant for expression. The fit between measured and predicted expression levels is shown in FIG. 15.

6.3.2 Design of a New Codon Bias Table

A new codon bias was calculated by calculating the average usage of each codon, in terms of codon frequency per codon position, in the top 10 expressed clones for the two gene variant sets. Thus a table was created to approximate the codon usage of highly expressed clones discovered through systematic gene variation and analysis.

6.4 APPLICATION OF CODON BIAS MODEL TO CENPA EXPRESSION IN E. COLI

Initial attempts to express the *Xenopus laevis* cenpA protein in *E. coli* using natural and re-designed synthetic genes had yielded no detectable product. In an attempt to increase yield, a new gene design was created based on our initial modeling results. A codon table, "ModA," was constructed in which the frequency usage of codons was weighted by the variable loadings in a model constructed from the combined scFv and phi29 DNA polymerase datasets as described above. For each amino acid, codons used at frequencies of less than 5% in *E. coli* genes were excluded from the table (set to zero frequency). The ModA table was then applied to cenpA gene design. Another design, where the codon frequencies were matched to those found in 27 highly expressed *E. coli* genes (Table "Coli-II") was also created. All design parameters other than codon frequency usage were similar for the two genes. The genes were expressed under identical conditions in identical *E. coli* host strains and expression level was analyzed by PAGE (FIG. 16). No significant expression relative to control strains (lacking cenpA) was observed from the Coli-II derived gene whereas significantly more product was seen from the ModA gene.

6.5 SEQUENCES

SEQAA (5' CONSTANT VECTOR SEQUENCE)

(SEQ ID NO: 1)

```
TGGCGAATGGGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTTCGCCC
TTTGACGTTGGAGTCCACGTTCTTTAATAGTGGACTCTTGTTCCAAACTGGAACAACACTCAACCCTATCTC
GGTCTATTCTTTTGATTTATAAGGGATTTTGCCGATTTCGGCCTATTGGTTAAAAAATGAGCTGATTTAACA
AAAATTTAACGCGAATTTTAACAAAATATTAACGTTTACAATTTCAGGTGGCACTTTTCGGGGAAATGTGCG
CGGAACCCCTATTTGTTTATTTTTCTAAATACATTCAAATATGTATCCGCTCATGAATTAATTCTTAGAAAA
ACTCATCGAGCATCAAATGAAACTGCAATTTATTCATATCAGGATTATCAATACCATATTTTTGAAAAAGCC
GTTTCTGTAATGAAGGAGAAAACTCACCGAGGCAGTTCCATAGGATGGCAAGATCCTGGTATCGGTCTGCGA
TTCCGACTCGTCCAACATCAATACAACCTATTAATTTCCCCTCGTCAAAAATAAGGTTATCAAGTGAGAAAT
CACCATGAGTGACGACTGAATCCGGTGAGAATGGCAAAAGTTTATGCATTTCTTTCCAGACTTGTTCAACAG
GCCAGCCATTACGCTCGTCATCAAAATCACTCGCATCAACCAAACCGTTATTCATTCGTGATTGCGCCTGAG
CGAGACGAAATACGCGATCGCTGTTAAAAGGACAATTACAAACAGGAATCGAATGCAACCGGCGCAGGAACA
CTGCCAGCGCATCAACAATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGATGGTCGGAAGAGGCATAA
ATTCCGTCAGCCAGTTTAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGATTGCCCGACATTATCGC
GAGCCCATTTATACCCATATAAATCAGCATCCATGTTGGAATTTAATCGCGGCCTAGAGCAAGACGTTTCCC
GTTGAATATGGCTCATAACACCCCTTGTATTACTGTTTATGTAAGCAGACAGTTTTATTGTTCATGACCAAA
ATCCCTTAACGTGAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATACCAAATACTGTCCTT
CTAGTGTAGCCGTAGTTAGGCCACCACTTCAAGAACTCTGTAGCACCGCCTACATACCTCGCTCTGCTAATC
CTGTTACCAGTGGCTGCTGCCAGTGGCGATAAGTCGTGTCTTACCGGGTTGGACTCAAGACGATAGTTACCG
GATAAGGCGCAGCGGTCGGGCTGAACGGGGGGTTCGTGCACACAGCCCAGCTTGGAGCGAACGACCTACACC
GAACTGAGATACCTACAGCGTGAGCTATGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGGGCGGAGCCTA
TGGAAAAACGCCAGCAACGCGGCCTTTTTACGGTTCCTGGCCTTTTGCTGGCCTTTTGCTCACATGTTCTTT
CCTGCGTTATCCCCTGATTCTGTGGATAACCGTATTACCGCCTTTGAGTGAGCTGATACCGCTCGCCGCAGC
CGAACGACCGAGCGCAGCGAGTCAGTGAGCGAGGAAGCGGAAGAGCGCCTGATGCGGTATTTTCTCCTTACG
CATCTGTGCGGTATTTCACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACACCCGCCAACACCCGCTGA
CGCGCCCTGACGGGCTTGTCTGCTCCCGGCATCCGCTTACAGACAAGCTGTGACCGTCTCCGGGAGCTGCAT
GTGTCAGAGGTTTTCACCGTCATCACCGAAACGCGCGAGGCAGCTGCGGTAAAGCTCATCAGCGTGGTCGTG
AAGCGATTCACAGATGTCTGCCTGTTCATCCGCGTCCAGCTCGTTGAGTTTCTCCAGAAGCGTTAATGTCTG
GCTTCTGATAAAGCGGGCCATGTTAAGGGCGGTTTTTTCCTGTTTGGTCACTGATGCCTCCGTGTAAGGGGG
```

-continued

```
ATTTCTGTTCATGGGGGTAATGATACCGATGAAACGAGAGAGGATGCTCACGATACGGGTTACTGATGATGA

ACATGCCCGGTTACTGGAACGTTGTGAGGGTAAACAACTGGCGGTATGGATGCGGCGGGACCAGAGAAAAT

CACTCAGGGTCAATGCCAGCGCTTCGTTAATACAGATGTAGGTGTTCCACAGGGTAGCCAGCAGCATCCTGC

GATGCAGATCCGGAACATAATGGTGCAGGGCGCTGACTTCCGCGTTTCCAGACTTTACGAAACACGGAAACC

GAAGACCATTCATGTTGTTGCTCAGGTCGCAGACGTTTTGCAGCAGCAGTCGCTTCACGTTCGCTCGCGTAT

CGGTGATTCATTCTGCTAACCAGTAAGGCAACCCCGCCAGCCTAGCCGGGTCCTCAACGACAGGAGCACGAT

CATGCGCACCCGTGGGGCCGCCATGCCGGCGATAATGGCCTGCTTCTCGCCGAAACGTTTGGTGGCGGGACC

AGTGACGAAGGCTTGAGCGAGGGCGTGCAAGATTCCGAATACCGCAAGCGACAGGCCGATCATCGTCGCGCT

CCAGCGAAAGCGGTCCTCGCCGAAAATGACCCAGAGCGCTGCCGGCACCTGTCCTACGAGTTGCATGATAAA

GAAGACAGTCATAAGTGCGGCGACGATAGTCATGCCCCGCGCCCACCGGAAGGAGCTGACTGGGTTGAAGGC

TCTCAAGGGCATCGGTCGAGATCCCGGTGCCTAATGAGTGAGCTAACTTACATTAATTGCGTTGCGCTCACT

GCCCGCTTTCCAGTCGGGAAACCTGTCGTGCCAGCTGCATTAATGAATCGGCCAACGCGCGGGGAGAGGCGG

TTTGCGTATTGGGCGCCAGGGTGGTTTTTCTTTTCACCAGTGAGACGGGCAACAGCTGATTGCCCTTCACCG

CCTGGCCCTGAGAGAGTTGCAGCAAGCGGTCCACGCTGGTTTGCCCCAGCAGGCGAAAATCCTGTTTGATGG

TGGTTAACGGCGGGATATAACATGAGCTGTCTTCGGTATCGTCGTATCCCACTACCGAGATATCCGCACCAA

CGCGCAGCCCGACTCGGTAATGGCGCGCATTGCGCCCAGCGCCATCTGATCGTTGGCAACCAGCATCGCAG

TGGGAACGATGCCCTCATTCAGCATTTGCATGGTTTGTTGAAAACCGGACATGGCACTCCAGTCGCCTTCCC

GTTCCGCTATCGGCTGAATTTGATTGCGAGTGAGATATTTATGCCAGCCAGCCAGACGCAGACGCGCCGAGA

CAGAACTTAATGGGCCCGCTAACAGCGCGATTTGCTGGTGACCCAATGCGACCAGATGCTCCACGCCCAGTC

GCGTACCGTCTTCATGGGAGAAAATAATACTGTTGATGGGTGTCTGGTCAGAGACATCAAGAAATAACGCCG

GAACATTAGTGCAGGCAGCTTCCACAGCAATGGCATCCTGGTCATCCAGCGGATAGTTAATGATCAGCCCAC

TGACGCGTTGCGCGAGAAGATTGTGCACCGCCGCTTTACAGGCTTCGACGCCGCTTCGTTCTACCATCGACA

CCACCACGCTGGCACCCAGTTGATCGGCGCGAGATTTAATCGCCGCGACAATTTGCGACGGCGCGTGCAGGG

CCAGACTGGAGGTGGCAACGCCAATCAGCAACGACTGTTTGCCCGCCAGTTGTTGTGCCACGCGGTTGGGAA

TGTAATTCAGCTCCGCCATCGCCGCTTCCACTTTTTCCCGCGTTTTCGCAGAAACGTGGCTGGCCTGGTTCA

CCACGCGGGAAACGGTCTGATAAGAGACACCGGCATACTCTGCGACATCGTATAACGTTACTGGTTTCACAT

TCACCACCCTGAATTGACTCTCTTCCGGGCGCTATCATGCCATACCGCGAAAGGTTTTGCGCCATTCGATGG

TGTCCGGGATCTCGACGCTCTCCCTTATGCGACTCCTGCATTAGGAAGCAGCCCAGTAGTAGGTTGAGGCCG

TTGAGCACCGCCGCCGCAAGGAATGGTGCATGCAAGGAGATGGCGCCCAACAGTCCCCGGCCACGGGGCCT

GCCACCATACCCACGCCGAAACAAGCGCTCATGAGCCCGAAGTGGCGAGCCCGATCTTCCCCATCGGTGATG

TCGGCGATATAGGCGCCAGCAACCGCACCTGTGGCGCCGGTGATGCCGGCCACGATGCGTCCGGCGTAGAGG

ATCGAGATCTCGATCCCGCGAAATTAATACGACTCACTATAGGGGAATTGTGAGCGGATAACAATTCCCCTC

TAGAAATAATTTTGTTTAACTTTAAGAAGGAGATATTACC
```

SEQAB (3' CONSTANT VECTOR SEQUENCE)

(SEQ ID NO: 2)
```
TGATAAAGTGGCTCCAACACTTCCTACTAGCATAACCCCTTGGGGCCTCTAAACGGGTCTTGAGGGGTTTTT

TGGAATTCGAGCTCCGTCGACAAGCTTGCGGCCGCACTCGAGCACCACCACCACCACCACTGAGATCCGGCT

GCTAACAAAGCCCGAAAGGAAGCTGAGTTGGCTGCTGCCACCGCTGAGCAATAACTAGCATAACCCCTTGGG

GCCTCTAAACGGGTCTTGAGGGGTTTTTTGCTGAAAGGAGGAACTATATCCGGAT
```

(SEQ ID NO: 3)
```
gtgggttctg aaagtgcagg cggatctgta ctttcacaac ctgaaattcg
```

-continued

```
                                                                    (SEQ ID NO: 4)
ggggaattgt gagcggataa caattcccct ctagaaataa ttttgtttaa ctttaagaag gagatattac catgaagcac atgccgcgga agatgtactc ctgcgacttc gagacgacca c
```

7 REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8 MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of designing a final polynucleotide that encodes an amino acid sequence of a predetermined polypeptide, the method comprising:
   (A) obtaining a frequency lookup table corresponding to an expression system, wherein the frequency lookup table is constructed by
      (i) constructing a plurality of test polynucleotides, wherein the plurality of test polynucleotides comprises five or more test polynucleotides, each respective test polynucleotide in the plurality of test polynucleotides encoding a respective test polypeptide sequence the entirety of which is at least ninety-five percent identical to the entirety of the respective test polypeptide sequence encoded by each other test polynucleotide in the plurality of test polynucleotides, wherein
         (a) a first amino acid is encoded a first plurality of times in each of a first test polynucleotide, a second test polynucleotide, and a third test polynucleotide in the plurality of test polynucleotides,
         (b) the first amino acid is encodable by a plurality of synonymous codons including a first codon;
         (c) the first codon is present in the first test polynucleotide with a first frequency relative to all other codons in the plurality of synonymous codons in the first test polynucleotide,
         (d) the first codon is present in the second test polynucleotide with a second frequency relative to all other codons in the plurality of synonymous codons in the second test polynucleotide,
         (e) the first codon is present in the third test polynucleotide with a third frequency relative to all other codons in the plurality of synonymous codons in the third test polynucleotide; and
         (f) the first frequency is different than the second frequency and the third frequency is between the first frequency and the second frequency;
      (ii) expressing each respective test polynucleotide in the plurality of test polynucleotides individually in said expression system using the same vector and the same promoter,
      (iii) measuring an expression property value of each respective test polynucleotide in the plurality of test polynucleotides in the expression system thereby constructing a dataset, wherein the dataset comprises, for each respective test polynucleotide in the plurality of test polynucleotides, (I) a representation of sequence element occurrence or a representation of sequence property occurrence in the respective test polynucleotide and (II) the measured expression property value of the respective test polynucleotide; and
      (iv) computing the frequency lookup table for said expression system based on the dataset;
   (B) defining a set of candidate polynucleotides, wherein each respective candidate polynucleotide in the set of candidate polynucleotides encodes the predetermined polypeptide;
   (C) determining, using a suitably programmed computer, a fit of each respective candidate polynucleotide in the set of candidate polynucleotides, wherein
      the fit of a respective candidate polynucleotide in the set of candidate polynucleotides is determined by a combination of a plurality of agreement scores, each respective agreement score in the plurality of agreement scores being a measure of agreement between (i) an actual sequence element frequency of a sequence element in the respective candidate polynucleotide sequence or an actual sequence property frequency of a sequence property in the respective candidate polynucleotide sequence and (ii) a frequency value or a frequency range specified for the sequence element or the sequence property in the frequency lookup table; and
   (D) identifying a candidate polynucleotide from the set of candidate polynucleotides as the final polynucleotide.

2. The method of claim 1, wherein the final polynucleotide is a candidate polynucleotide in the set of candidate polynucleotides that has a fit that is closer to an ideal fit than any other candidate polynucleotide in the set of candidate polynucleotides.

3. The method of claim 1, wherein the frequency lookup table further comprises a model that computes an estimated expression property value for an expression property of the predetermined polypeptide as a function of a nucleotide sequence of a candidate polynucleotide, and wherein the fit determined for a respective candidate polynucleotide in an instance of the determining (C) is further determined by the estimated expression property value for the predetermined polypeptide calculated by the model based on a nucleotide sequence of the respective candidate polynucleotide.

4. The method of claim 1, wherein the defining (B) further comprises:
  (i) exclusion of a restriction site sequence in a candidate polynucleotide in the set of polynucleotides;
  (ii) incorporation of a restriction site sequence in a candidate polynucleotide in the set of polynucleotides;
  (iii) a designation of a target G+C content in a candidate polynucleotide in the set of polynucleotides;
  (iv) exclusion of a sub-sequence, longer than an allowable length, that can be exactly repeated within either strand of a candidate polynucleotide in the set of candidate polynucleotides;
  (v) exclusion of a first sub-sequence that can anneal at a greater than an allowable annealing temperature to a second sub-sequence within either strand of a candidate polynucleotide in the set of polynucleotides;
  (vi) exclusion of a hairpin turn in a candidate polynucleotide in the set of polynucleotides;
  (vii) exclusion of a repeat element in a candidate polynucleotide in the set of polynucleotides;
  (viii) exclusion of a ribosome binding site in a candidate polynucleotide in the set of polynucleotides;
  (ix) exclusion of a polyadenylation signal in a candidate polynucleotide in the set of polynucleotides;
  (x) exclusion of a splice site in a candidate polynucleotide in the set of polynucleotides;
  (xi) exclusion of an open reading frame in each possible reading frame in a candidate polynucleotide in the set of polynucleotides other than a reading frame encoding the amino acid sequence;
  (xii) exclusion of a polynucleotide sequence that facilitates RNA degradation in a candidate polynucleotide in the set of polynucleotides;
  (xiii) exclusion of an RNA polymerase termination signal in a candidate polynucleotide in the set of polynucleotides;
  (xiv) exclusion of a transcriptional promoter in a candidate polynucleotide in the set of polynucleotides;
  (xv) exclusion of an immunostimulatory sequence in a candidate polynucleotide in the set of polynucleotides;
  (xvi) incorporation of an immunostimulatory sequence in a candidate polynucleotide in the set of polynucleotides;
  (xvii) exclusion of an RNA methylation signal in a candidate polynucleotide in the set of polynucleotides;
  (xviii) exclusion of a selenocysteine incorporation signal in a candidate polynucleotide in the set of polynucleotides;
  (xix) exclusion of an RNA editing sequence in a candidate polynucleotide in the set of polynucleotides;
  (xx) exclusion of an RNAi-targeted sequence in a candidate polynucleotide in the set of polynucleotides;
  (xxi) exclusion of an inverted repeat within the first x nucleotides encoding the amino acid sequence in a candidate polynucleotide in the set of polynucleotides, where x is any number between one nucleotide and one hundred nucleotides; or
  (xxii) exclusion of a DNA methylation signal in a candidate polynucleotide in the set of polynucleotides.

5. The method of claim 1, wherein the agreement score determined for a candidate polynucleotide in the set of candidate polynucleotides in an instance of the determining (C) is further determined by:
  (i) exclusion of a restriction site sequence in the candidate polynucleotide;
  (ii) incorporation of a restriction site sequence in the candidate polynucleotide;
  (iii) a designation of a target G+C content in the candidate polynucleotide;
  (iv) exclusion of a sub-sequence, longer than an allowable length, that can be exactly repeated within either strand of the candidate polynucleotide;
  (v) exclusion of a first sub-sequence that can anneal at a greater than an allowable annealing temperature to a second sub-sequence within either strand of the candidate polynucleotide;
  (vi) exclusion of a hairpin turn in the candidate polynucleotide;
  (vii) exclusion of a repeat element in the candidate polynucleotide;
  (viii) exclusion of a ribosome binding site in the candidate polynucleotide;
  (ix) exclusion of a polyadenylation signal in the candidate polynucleotide;
  (x) exclusion of a splice site in the candidate polynucleotide;
  (xi) exclusion of an open reading frame in each possible reading frame in the candidate polynucleotide other than a reading frame encoding the amino acid sequence;
  (xii) exclusion of a polynucleotide sequence that facilitates RNA degradation in the candidate polynucleotide;
  (xiii) exclusion of an RNA polymerase termination signal in the candidate polynucleotide;
  (xiv) exclusion of a transcriptional promoter in the candidate polynucleotide;
  (xv) exclusion of an immunostimulatory sequence in the candidate polynucleotide;
  (xvi) incorporation of an immunostimulatory sequence in the candidate polynucleotide;
  (xvii) exclusion of an RNA methylation signal in the candidate polynucleotide;
  (xviii) exclusion of a selenocysteine incorporation signal in the candidate polynucleotide;
  (xix) exclusion of an RNA editing sequence in the candidate polynucleotide;
  (xx) exclusion of an RNAi-targeted sequence in the candidate polynucleotide;
  (xxi) exclusion of an inverted repeat within the first x nucleotides encoding the amino acid sequence in the candidate polynucleotide, where x is any number between one nucleotide and one hundred nucleotides; or
  (xxii) exclusion of a DNA methylation signal in the candidate polynucleotide.

6. The method of claim 1, the method further comprising, prior to said identifying step (D):
  (1) determining whether an exit condition has been satisfied;
  (2) enriching, when the exit condition has not been satisfied, the set of candidate polynucleotides by removing a portion of the candidate polynucleotides from the set of candidate polynucleotides based on a respective fit determined for each candidate polynucleotide in the set of candidate polynucleotides; and
  (3) enriching, when the exit condition has not been satisfied, the set of candidate polynucleotides by adding a subset of candidate polynucleotides to the set of candidate polynucleotides, wherein each candidate polynucleotide in the subset of candidate polynucleotides is derived from one or more candidate polynucleotides already in the set of candidate polynucleotides and wherein each candidate polynucleotide in the subset of candidate polynucleotides encodes the amino acid sequence of the predetermined polypeptide; and (4) repeating (C), (1), (2), and (3) until an exit condition has been satisfied in an instance of the determining (1).

7. The method of claim 6, wherein the exit condition is the repetition of (C), (1), (2), and (3) a predetermined number of times.

8. The method of claim 6, wherein the exit condition is the repetition of (C), (1), (2), and (3) until a fit of a candidate polynucleotide computed in an instance of the determining (C) is within a predetermined threshold of an ideal score.

9. The method of claim 1, wherein a frequency range is specified for a respective sequence element in the frequency lookup table, wherein the respective sequence element is a codon, and wherein each frequency in the frequency range for the codon in the frequency lookup table is a frequency that the codon can be incorporated into a polynucleotide relative to all other naturally occurring codons that are synonymous to the codon.

10. The method of claim 1, wherein a frequency range is specified for a respective sequence element in the frequency lookup table, wherein the respective sequence element is a codon, and wherein each frequency in the frequency range for the codon in the frequency lookup table is a frequency that the codon can be incorporated into a polynucleotide relative to all other codons represented by the frequency lookup table.

11. The method of claim 1, wherein a frequency range is specified for a respective sequence element in the frequency lookup table, wherein the respective sequence element is a codon, and wherein each frequency in the frequency range for the codon in the frequency lookup table is a frequency that the respective codon can be incorporated into a polynucleotide relative to all other naturally occurring codons.

12. The method of claim 1, wherein each sequence element in the frequency lookup table is a corresponding naturally occurring codon in a plurality of codons, and wherein said computing said frequency lookup table (iv) comprises assigning, for each respective codon in the plurality of codons in the frequency lookup table, a target frequency or a target frequency range to the respective codon based on an absolute or relative frequency of the codon in a set of test polynucleotides in the plurality of test polynucleotides that has the most desirable expression property values.

13. The method of claim 12, wherein, for each respective codon in the plurality of codons in the frequency lookup table, a target frequency is assigned to the respective codon based on an arithmetic or geometric mean of the absolute or relative frequency of the codon in the set of test polynucleotides.

14. The method of claim 1, wherein said computing said frequency lookup table for said expression system based on the dataset comprises:

(1) regressing a model comprising (i) a plurality of variables, each variable in the plurality of variables describing a frequency of occurrence of one or more codons in the plurality of test polynucleotides, and (ii) a plurality of weights, each weight in the plurality of weights corresponding to one or more variables in the plurality of variables, and wherein the model describes a variation in the measured expression property values of the plurality of test polynucleotides from the measuring (iii) as a function of the plurality of variables and their corresponding weights; and (2) constructing said frequency lookup table for the expression system from the model, wherein the sequence element frequency for a codon in the frequency lookup table is determined by a corresponding regression vector in the model for the codon.

15. The method of claim 14, wherein the model is regressed by partial least squares regression.

16. The method of claim 1, wherein the expression property value of each respective test polynucleotide in the plurality of test polynucleotides in the expression system is a total amount of protein encoded by the respective test polynucleotide that is expressed in the expression system in a predetermined period of time.

17. The method of claim 1, wherein the expression property value of each respective test polynucleotide in the plurality of test polynucleotides in the expression system is a total amount of active protein encoded by the respective test polynucleotide that is expressed in the expression system in a predetermined period of time.

18. The method of claim 1, wherein the expression property value of each respective polynucleotide in the plurality of polynucleotides in the expression system is a total amount of soluble protein encoded by the respective polynucleotide that is expressed in the expression system in a predetermined period of time.

19. The method of claim 1 wherein, for each respective amino acid in a plurality of amino acids comprising five or more amino acids, a relative frequency of each of a plurality of synonymous codons for the respective amino acid is varied in a region of each of two or more of the test polynucleotides in the plurality of test polynucleotides.

20. The method of claim 1 wherein, for each respective amino acid in a plurality of amino acids comprising two or more amino acids, a relative frequency of each of a plurality of synonymous codons for the respective amino acid is varied in a region of each of five or more of the test polynucleotides in the plurality of test polynucleotides.

21. The method of claim 1, wherein the plurality of test polynucleotides comprises ten or more polynucleotides.

22. The method of claim 1, wherein the plurality of test polynucleotides comprises twenty or more polynucleotides.

23. The method of claim 1, the method further comprising outputting the frequency lookup table to a user interface device, a tangible computer readable storage medium; or displaying the frequency lookup table in user readable form.

24. The method of claim 1, wherein the dataset comprises the representation of sequence element occurrence and wherein the sequence element is a codon.

25. The method of claim 1, wherein the dataset comprises the representation of sequence element occurrence and wherein the sequence element is a codon pair.

26. The method of claim 1 wherein said computing said frequency lookup table (iv) comprises assigning, for a sequence element in the frequency lookup table, a target frequency or a target frequency range to the sequence element based on an absolute or relative frequency of the sequence element in a test polynucleotide in the plurality of test polynucleotides that has the most desirable expression property value.

27. The method of claim 26, wherein the sequence element is a codon.

28. The method of claim 26, wherein the sequence element is a codon pair.

29. The method of claim 1, wherein a sequence element in the frequency lookup table is a codon, and wherein said computing said frequency lookup table (iv) comprises assigning a target frequency or a target frequency range to the codon based on an absolute or relative frequency of the codon in a set of test polynucleotides in the plurality of test polynucleotides, wherein the set of test polynucleotides consists of between one and ten test polynucleotides in the plurality of test polynucleotides that have the most desirable expression property values.

30. The method of claim 29 wherein a target frequency is assigned to the codon based on an arithmetic or geometric mean of the absolute or relative frequency of the codon in the set of test polynucleotides.

31. The method of claim 1, wherein the predetermined polypeptide is unrelated in sequence to a test polypeptide encoded by any test polynucleotide in the plurality of test polynucleotides.

32. The method of claim 1, wherein the dataset comprises the representation of sequence element occurrence and wherein the sequence element is a defined sequence of nucleotides that optionally includes a reading frame designation relative to the reading frame of a polypeptide encoded by a polynucleotide.

33. The method of claim 1, wherein the dataset comprises the representation of sequence element occurrence and wherein the sequence element is a nucleotide triplet in the +3 reading frame that encodes the "wobble" or third base of one codon and the first two bases of the following codon in the reading frame of a polypeptide encoded by a polynucleotide.

34. The method of claim 1, wherein the dataset comprises the representation of sequence property occurrence and wherein the sequence property is polynucleotide GC content.

35. The method of claim 1, wherein the dataset comprises the representation of sequence property occurrence and wherein the sequence property is presence of an mRNA secondary structure in a predetermined region of an mRNA produced by a polynucleotide.

36. The method of claim 35, wherein the predetermined region encompasses a start codon.

37. The method of claim 1, wherein the dataset comprises the representation of sequence property occurrence and wherein the sequence property is a ribosome binding site, an mRNA destabilizing motif, an RNAse recognition sequence or a polyadenylation signal.

38. The method of claim 1, wherein the dataset comprises the representation of sequence property occurrence and the sequence property is an annealing temperature for a sub-sequence of predetermined length within a polynucleotide for any other sub-sequence within the polynucleotide.

39. The method of claim 1, wherein the dataset comprises the representation of sequence element occurrence and wherein the sequence element is a homopolymer stretch, a G/C island or an A/T island.

40. The method of claim 1, wherein the frequency lookup table is a sequence element frequency lookup table, a sequence property frequency lookup table, a codon frequency matrix, or a design polynucleotide sequence property lookup table.

41. The method of claim 1, wherein the dataset comprises the representation of sequence element occurrence and wherein the sequence element is a polynucleotide sequence that is repeated.

42. The method of claim 1, wherein the dataset comprises the representation of a sequence element occurrence and wherein the sequence element is a transcriptional termination motif.

43. The method of claim 1, wherein the dataset comprises the representation of sequence element occurrence and wherein the sequence element is a restriction site sequence.

44. The method of claim 1 wherein the dataset comprises, for each respective test polynucleotide in the plurality of test polynucleotides, (I) an independent representation of sequence element occurrence for each of two or more different sequence elements and (II) the measured expression property value of the respective test polynucleotide.

45. The method of claim 1 wherein the dataset comprises, for each respective test polynucleotide in the plurality of test polynucleotides, (I) an independent representation of sequence element occurrence for each of five or more different sequence elements and (II) the measured expression property value of the respective test polynucleotide.

46. A non-transitory computer-readable medium that stores one or more computer programs for designing a final polynucleotide that encodes an amino acid sequence of a predetermined polypeptide, the one or more computer programs executable by a computer, the one or more computer programs collectively comprising instructions for:
(A) obtaining a frequency lookup table corresponding to an expression system, wherein the frequency lookup table is constructed by
(i) constructing a plurality of test polynucleotides, wherein the plurality of test polynucleotides comprises five or more test polynucleotides, each respective test polynucleotide in the plurality of test polynucleotides encoding a respective test polypeptide sequence the entirety of which is at least ninety-five percent identical to the entirety of the respective test polypeptide sequence encoded by each other test polynucleotide in the plurality of test polynucleotides, wherein
(a) a first amino acid is encoded a first plurality of times in each of a first test polynucleotide, a second test polynucleotide, and a third test polynucleotide in the plurality of test polynucleotides,
(b) the first amino acid is encodable by a plurality of synonymous codons including a first codon;
(c) the first codon is present in the first test polynucleotide with a first frequency relative to all other codons in the plurality of synonymous codons in the first test polynucleotide,
(d) the first codon is present in the second test polynucleotide with a second frequency relative to all other codons in the plurality of synonymous codons in the second test polynucleotide,
(e) the first codon is present in the third test polynucleotide with a third frequency relative to all other codons in the plurality of synonymous codons in the third test polynucleotide; and
(f) the first frequency is different than the second frequency and the third frequency is between the first frequency and the second frequency;
(ii) expressing each respective test polynucleotide in the plurality of test polynucleotides individually in said expression system using the same vector and the same promoter,
(iii) measuring an expression property value of each respective test polynucleotide in the plurality of test polynucleotides in the expression system thereby constructing a dataset, wherein the dataset comprises, for each respective test polynucleotide in the plurality of test polynucleotides, (I) a representation of sequence element occurrence or a representation of sequence property occurrence in the respective test polynucleotide and (II) the measured expression property value of the respective test polynucleotide; and (iv) computing the frequency lookup table for said expression system based on the dataset;

(B) defining a set of candidate polynucleotides, wherein each respective candidate polynucleotide in the set of candidate polynucleotides encodes the predetermined polypeptide;

(C) determining, using a suitably programmed computer, a fit of each respective candidate polynucleotide in the set of candidate polynucleotides, wherein the fit of a respective candidate polynucleotide in the set of candidate test polynucleotides is determined by a combination of a plurality of agreement scores, each respective agreement score in the plurality of agreement scores being a measure of agreement between (i) an actual sequence element frequency of a sequence element in in the respective candidate polynucleotide sequence or an actual sequence property frequency of a sequence property in the respective candidate polynucleotide sequence and (ii) a frequency value or a frequency range specified for the sequence element or the sequence property in the frequency lookup table; and (D) identifying a candidate polynucleotide from the set of candidate polynucleotides as the final polynucleotide.

47. The non-transitory computer-readable medium of claim 46, wherein the final polynucleotide is a candidate polynucleotide in the set of candidate polynucleotides that has a fit that is closer to an ideal fit than any other candidate polynucleotide in the set of candidate polynucleotides.

48. The non-transitory computer-readable medium of claim 46, wherein the frequency lookup table further comprises a model that computes an estimated expression property value for an expression property of the predetermined polypeptide as a function of a nucleotide sequence of a candidate polynucleotide, and wherein the fit determined for a respective candidate polynucleotide in an instance of the determining (C) is further determined by the estimated expression property value for the predetermined polypeptide calculated by the model based on a nucleotide sequence of the respective candidate polynucleotide.

49. The non-transitory computer-readable medium of claim 46, wherein the defining (B) further comprises:

(i) exclusion of a restriction site sequence in a candidate polynucleotide in the set of polynucleotides;

(ii) incorporation of a restriction site sequence in a candidate polynucleotide in the set of polynucleotides;

(iii) a designation of a target G+C content in a candidate polynucleotide in the set of polynucleotides;

(iv) exclusion of a sub-sequence, longer than an allowable length, that can be exactly repeated within either strand of a candidate polynucleotide in the set of polynucleotides;

(v) exclusion of a first sub-sequence that can anneal at a greater than an allowable annealing temperature to a second sub-sequence within either strand of a candidate polynucleotide in the set of polynucleotides;

(vi) exclusion of a hairpin turn in a candidate polynucleotide in the set of polynucleotides;

(vii) exclusion of a repeat element in a candidate polynucleotide in the set of polynucleotides;

(viii) exclusion of a ribosome binding site in a candidate polynucleotide in the set of polynucleotides;

(ix) exclusion of a polyadenylation signal in a candidate polynucleotide in the set of polynucleotides;

(x) exclusion of a splice site in a candidate polynucleotide in the set of polynucleotides;

(xi) exclusion of an open reading frame in each possible reading frame in a candidate polynucleotide in the set of polynucleotides other than a reading frame encoding the amino acid sequence;

(xii) exclusion of a polynucleotide sequence that facilitates RNA degradation in a candidate polynucleotide in the set of polynucleotides;

(xiii) exclusion of an RNA polymerase termination signal in a candidate polynucleotide in the set of polynucleotides;

(xiv) exclusion of a transcriptional promoter in a candidate polynucleotide in the set of polynucleotides;

(xv) exclusion of an immunostimulatory sequence in a candidate polynucleotide in the set of polynucleotides;

(xvi) incorporation of an immunostimulatory sequence in a candidate polynucleotide in the set of polynucleotides;

(xvii) exclusion of an RNA methylation signal in a candidate polynucleotide in the set of polynucleotides;

(xviii) exclusion of a selenocysteine incorporation signal in a candidate polynucleotide in the set of polynucleotides;

(xix) exclusion of an RNA editing sequence in a candidate polynucleotide in the set of polynucleotides;

(xx) exclusion of an RNAi-targeted sequence in a candidate polynucleotide in the set of polynucleotides;

(xxi) exclusion of an inverted repeat within the first x nucleotides encoding the amino acid sequence in a candidate polynucleotide in the set of polynucleotides, where x is any number between one nucleotide and one hundred nucleotides; or (xxii) exclusion of a DNA methylation signal in a candidate polynucleotide in the set of polynucleotides.

50. The non-transitory computer readable medium of claim 46, wherein the agreement score determined for a candidate polynucleotide in the set of candidate polynucleotides in an instance of the determining (C) is further determined by:

(i) exclusion of a restriction site sequence in the candidate polynucleotide;

(ii) incorporation of a restriction site sequence in the candidate polynucleotide;

(iii) a designation of a target G+C content in the candidate polynucleotide;

(iv) exclusion of a sub-sequence, longer than an allowable length, that can be exactly repeated within either strand of the candidate polynucleotide;

(v) exclusion of a first sub-sequence that can anneal at a greater than an allowable annealing temperature to a second sub-sequence within either strand of the candidate polynucleotide;

(vi) exclusion of a hairpin turn in the candidate polynucleotide;

(vii) exclusion of a repeat element in the candidate polynucleotide;

(viii) exclusion of a ribosome binding site in the candidate polynucleotide;

(ix) exclusion of a polyadenylation signal in the candidate polynucleotide;

(x) exclusion of a splice site in the candidate polynucleotide;

(xi) exclusion of an open reading frame in each possible reading frame in the candidate polynucleotide other than a reading frame encoding the amino acid sequence;

(xii) exclusion of a polynucleotide sequence that facilitates RNA degradation in the candidate polynucleotide;

(xiii) exclusion of an RNA polymerase termination signal in the candidate polynucleotide;

(xiv) exclusion of a transcriptional promoter in the candidate polynucleotide;

(xv) exclusion of an immunostimulatory sequence in the candidate polynucleotide;

(xvi) incorporation of an immunostimulatory sequence in the candidate polynucleotide;

(xvii) exclusion of an RNA methylation signal in the candidate polynucleotide;

(xviii) exclusion of a selenocysteine incorporation signal in the candidate polynucleotide;

(xix) exclusion of an RNA editing sequence in the candidate polynucleotide;

(xx) exclusion of an RNAi-targeted sequence in the candidate polynucleotide;

(xxi) exclusion of an inverted repeat within the first x nucleotides encoding the amino acid sequence in the candidate polynucleotide, where x is any number between one nucleotide and one hundred nucleotides; or (xxii) exclusion of a DNA methylation signal in the candidate polynucleotide.

51. The non-transitory computer-readable medium of claim 46, wherein the one or more computer programs further collectively comprise instructions for execution, prior to (D), that (1) determine whether an exit condition has been satisfied;

(2) enrich, when the exit condition has not been satisfied, the set of candidate polynucleotides by removing a portion of the candidate polynucleotides from the set of candidate polynucleotides based on a respective fit determined for each candidate polynucleotide in the set of candidate polynucleotides; and (3) enrich, when the exit condition has not been satisfied, the set of candidate polynucleotides by adding a subset of candidate polynucleotides to the set of candidate polynucleotides, wherein each candidate polynucleotide in the subset of candidate polynucleotides is derived from one or more candidate polynucleotides already in the set of candidate polynucleotides and wherein each candidate polynucleotide in the subset of candidate polynucleotides encodes the amino acid sequence of the predetermined polypeptide; and (4) repeat (C), (1), (2), and (3) until an exit condition has been satisfied in an instance of (1).

52. The non-transitory computer-readable medium of claim 51, wherein the exit condition is the repetition of (C), (1), (2), and (3) a predetermined number of times.

53. The non-transitory computer-readable medium of claim 51, wherein the exit condition is the repetition of (C), (1), (2), and (3) until a fit of a candidate polynucleotide computed in an instance of the determining (C) is within a predetermined threshold of an ideal score.

54. The non-transitory computer readable medium of claim 46 wherein the frequency lookup table is a sequence element frequency lookup table, a codon frequency matrix, or a design polynucleotide sequence property lookup table.

55. An apparatus for designing a final polynucleotide that encodes an amino acid sequence of a predetermined polypeptide comprising:

one or more physical processors; and a physical memory, wherein the physical memory is electrically coupled to the one or more physical processors, the physical memory storing one or more computer programs that collectively comprise instructions for:

(A) obtaining a frequency lookup table corresponding to an expression system, wherein the frequency lookup table is constructed by (i) constructing a plurality of test polynucleotides, wherein the plurality of test polynucleotides comprises five or more test polynucleotides, each respective test polynucleotide in the plurality of test polynucleotides encoding a respective test polypeptide sequence the entirety of which is at least ninety-five percent identical to the entirety of the respective test polypeptide sequence encoded by each other test polynucleotide in the plurality of test polynucleotides, wherein (a) a first amino acid is encoded a first plurality of times in each of a first test polynucleotide, a second test polynucleotide, and a third test polynucleotide in the plurality of test polynucleotides, (b) the first amino acid is encodable by a plurality of synonymous codons including a first codon;

(c) the first codon is present in the first test polynucleotide with a first frequency relative to all other codons in the plurality of synonymous codons in the first test polynucleotide, (d) the first codon is present in the second test polynucleotide with a second frequency relative to all other codons in the plurality of synonymous codons in the second test polynucleotide, (e) the first codon is present in the third test polynucleotide with a third frequency relative to all other codons in the plurality of synonymous codons in the third test polynucleotide; and (f) the first frequency is different than the second frequency and the third frequency is between the first frequency and the second frequency;

(ii) expressing each respective test polynucleotide in the plurality of test polynucleotides individually in said expression system using the same vector and the same promoter, (iii) measuring an expression property value of each respective test polynucleotide in the plurality of test polynucleotides in the expression system thereby constructing a dataset, wherein the dataset comprises, for each respective test polynucleotide in the plurality of test polynucleotides, (I) a representation of sequence element occurrence or a representation of sequence property occurrence in the respective test polynucleotide and (II) the measured expression property value of the respective test polynucleotide; and (iv) computing the frequency lookup table for said expression system based on the dataset;

(B) defining a set of candidate polynucleotides, wherein each respective candidate polynucleotide in the set of candidate polynucleotides encodes the predetermined polypeptide;

(C) determining, using a suitably programmed computer, a fit of each respective candidate polynucleotide in the set of candidate polynucleotides, wherein the fit of a respective candidate polynucleotide in the set of candidate polynucleotides is determined by a combination of a plurality of agreement scores, each respective agreement score in the plurality of agreement scores being a measure of agreement between (i) an actual sequence element frequency of a sequence element in the respective candidate polynucleotide sequence or an actual sequence property frequency of a sequence property in the respective candidate polynucleotide sequence and (ii) a frequency value or a frequency range specified for the respective sequence element or the sequence property in the frequency lookup table; and (D) identifying a candidate polynucleotide from the set of candidate polynucleotides as the final polynucleotide.

56. The apparatus of claim 55, wherein the final polynucleotide is a candidate polynucleotide in the set of candidate polynucleotides that has a fit that is closer to an ideal fit than any other candidate polynucleotide in the set of candidate polynucleotides.

57. The apparatus of claim 55, wherein the frequency lookup table further comprises a model that computes an estimated expression property value for an expression property of the predetermined polypeptide as a function of a nucleotide sequence of a candidate polynucleotide, and wherein the fit determined for a respective candidate polynucleotide in an instance of the determining (C) is further determined by the estimated expression property value for the predetermined polypeptide calculated by the model based on a nucleotide sequence of the respective candidate polynucleotide.

58. The apparatus of claim 55, wherein the defining (B) further comprises:
   (i) exclusion of a restriction site sequence in a candidate polynucleotide in the set of polynucleotides;
   (ii) incorporation of a restriction site sequence in a candidate polynucleotide in the set of polynucleotides;
   (iii) a designation of a target G+C content in a candidate polynucleotide in the set of polynucleotides;
   (iv) exclusion of a sub-sequence, longer than an allowable length, that can be exactly repeated within either strand of a candidate polynucleotide in the set of polynucleotides;
   (v) exclusion of a first sub-sequence that can anneal at a greater than an allowable annealing temperature to a second sub-sequence within either strand of a candidate polynucleotide in the set of polynucleotides;
   (vi) exclusion of a hairpin turn in a candidate polynucleotide in the set of polynucleotides;
   (vii) exclusion of a repeat element in a candidate polynucleotide in the set of polynucleotides;
   (viii) exclusion of a ribosome binding site in a candidate polynucleotide in the set of polynucleotides;
   (ix) exclusion of a polyadenylation signal in a candidate polynucleotide in the set of polynucleotides;
   (x) exclusion of a splice site in a candidate polynucleotide in the set of polynucleotides;
   (xi) exclusion of an open reading frame in each possible reading frame in a candidate polynucleotide in the set of polynucleotides other than a reading frame encoding the amino acid sequence;
   (xii) exclusion of a polynucleotide sequence that facilitates RNA degradation in a candidate polynucleotide in the set of polynucleotides;
   (xiii) exclusion of an RNA polymerase termination signal in a candidate polynucleotide in the set of polynucleotides;
   (xiv) exclusion of a transcriptional promoter in a candidate polynucleotide in the set of polynucleotides;
   (xv) exclusion of an immunostimulatory sequence in a candidate polynucleotide in the set of polynucleotides;
   (xvi) incorporation of an immunostimulatory sequence in a candidate polynucleotide in the set of polynucleotides;
   (xvii) exclusion of an RNA methylation signal in a candidate polynucleotide in the set of polynucleotides;
   (xviii) exclusion of a selenocysteine incorporation signal in a candidate polynucleotide in the set of polynucleotides;
   (xix) exclusion of an RNA editing sequence in a candidate polynucleotide in the set of polynucleotides;
   (xx) exclusion of an RNAi-targeted sequence in a candidate polynucleotide in the set of polynucleotides;
   (xxi) exclusion of an inverted repeat within the first x nucleotides encoding the amino acid sequence in a candidate polynucleotide in the set of polynucleotides, where x is any number between one nucleotide and one hundred nucleotides; or
   (xxii) exclusion of a DNA methylation signal in a candidate polynucleotide in the set of polynucleotides.

59. The apparatus of claim 55, wherein the agreement score determined for a candidate polynucleotide in the set of candidate polynucleotides in an instance of the determining (C) is further determined by:
   (i) exclusion of a restriction site sequence in the candidate polynucleotide;
   (ii) incorporation of a restriction site sequence in the candidate polynucleotide;
   (iii) a designation of a target G+C content in the candidate polynucleotide;
   (iv) exclusion of a sub-sequence, longer than an allowable length, that can be exactly repeated within either strand of the candidate polynucleotide;
   (v) exclusion of a first sub-sequence that can anneal at a greater than an allowable annealing temperature to a second sub-sequence within either strand of the candidate polynucleotide;
   (vi) exclusion of a hairpin turn in the candidate polynucleotide;
   (vii) exclusion of a repeat element in the candidate polynucleotide;
   (viii) exclusion of a ribosome binding site in the candidate polynucleotide;
   (ix) exclusion of a polyadenylation signal in the candidate polynucleotide;
   (x) exclusion of a splice site in the candidate polynucleotide;
   (xi) exclusion of an open reading frame in each possible reading frame in the candidate polynucleotide other than a reading frame encoding the amino acid sequence;
   (xii) exclusion of a polynucleotide sequence that facilitates RNA degradation in the candidate polynucleotide;
   (xiii) exclusion of an RNA polymerase termination signal in the candidate polynucleotide;
   (xiv) exclusion of a transcriptional promoter in the candidate polynucleotide;
   (xv) exclusion of an immunostimulatory sequence in the candidate polynucleotide;
   (xvi) incorporation of an immunostimulatory sequence in the candidate polynucleotide;
   (xvii) exclusion of an RNA methylation signal in the candidate polynucleotide;
   (xviii) exclusion of a selenocysteine incorporation signal in the candidate polynucleotide;
   (xix) exclusion of an RNA editing sequence in the candidate polynucleotide;
   (xx) exclusion of an RNAi-targeted sequence in the candidate polynucleotide;
   (xxi) exclusion of an inverted repeat within the first x nucleotides encoding the amino acid sequence in the candidate polynucleotide, where x is any number between one nucleotide and one hundred nucleotides; or (xxii) exclusion of a DNA methylation signal in the candidate polynucleotide.

60. The apparatus of claim 55, wherein the one or more computer programs further collectively comprise instructions for execution, prior to (D), that
   (1) determine whether an exit condition has been satisfied;
   (2) enrich, when the exit condition has not been satisfied, the set of candidate polynucleotides by removing a portion of the candidate polynucleotides from the set of candidate polynucleotides based on a respective fit determined for each candidate polynucleotide in the set of candidate polynucleotides;
   (3) enrich, when the exit condition has not been satisfied, the set of candidate polynucleotides by adding a subset of candidate polynucleotides to the set of candidate polynucleotides, wherein each candidate polynucleotide in the subset of candidate polynucleotides is derived from one or more candidate polynucleotides already in the set of candidate polynucleotides and wherein each candidate polynucleotide in the subset of candidate polynucleotides encodes the amino acid sequence of the predetermined polypeptide; and
   (4) repeat (C), (1), (2), and (3) until an exit condition has been satisfied in an instance of the determining (1).

61. The apparatus of claim 55, wherein the exit condition is the repetition of (C), (1), (2), and (3) a predetermined number of times.

62. The apparatus of claim 55, wherein the exit condition is the repetition of (C), (1), (2), and (3) until a fit of a candidate polynucleotide computed in an instance of the determining (C) is within a predetermined threshold of an ideal score.

63. The apparatus of claim 55 wherein the frequency lookup table is a sequence element frequency lookup table, a codon frequency matrix, or a design polynucleotide sequence property lookup table.

* * * * *